US005846806A

United States Patent [19]

Jones et al.

[11] Patent Number: 5,846,806

[45] Date of Patent: Dec. 8, 1998

[54] IDENTIFICATION OF A HUMAN CYTOMEGALOVIRUS GENE REGION INVOLVED IN DOWN-REGULATION OF MHC CLASS I HEAVY CHAIN EXPRESSION

[75] Inventors: Thomas R. Jones, Nyack, N.Y.; Ann E. Campbell, Norfalk, Va.

[73] Assignees: American Cyanamid Company, Madison, N.J.; Eastern Virginia Medical School, Norfolk, Va.

[21] Appl. No.: 282,696

[22] Filed: Jul. 29, 1994

[51] Int. Cl.$^6$ .......... C12N 7/04

[52] U.S. Cl. .......... 435/236

[58] Field of Search .......... 435/172.3, 235.1, 435/236, 320.1; 424/230.1

[56] References Cited

FOREIGN PATENT DOCUMENTS 0521427 1/1993 European Pat. Off. .

WO89/10966 11/1989 WIPO .

OTHER PUBLICATIONS

Chee M.S. et al., Current Topics in Microbiology and Immunology, vol. 154, 1990, pp. 126–169.

Gilbert, M.J. et al., J. Virology, vol. 67, No. 6, 1993, pp. 3461–3469.

Beersma, M.F.C. et al., J. Immunology, vol. 151, No. 9, 1993, pp. 4455–4464.

Jones et al., T.R. et al., J. Virology, vol. 69, No. 8, 1995, pp. 4830–4841.

Colberg–Poley, A. M. et al., J. Virology, vol. 66, No. 1, 1992, pp. 95–105.

Jones et al., J. of Virology, Apr. 1992, vol. 66(4): pp. 2541–2546.

Kollert–Jöns et al., J. of Virology, Oct. 1991, vol. 65(10): pp. 5184–5189.

Jones et al., J. of Virology, Nov. 1991, vol. 65(11): pp. 5860–5872.

Jones et al., J. of Virology, Apr. 1991, vol. 65(4): pp. 2024–2036.

*Primary Examiner*—Mindy Fleisher
*Assistant Examiner*—Terry A. McKelvey
*Attorney, Agent, or Firm*—Elizabeth M. Barnhard

[57] ABSTRACT

Infection of human fibroblast cells with human cytomegalovirus (HCMV) causes down regulation of cell surface expression of MHC class I. The present invention is directed to a mutant with a 9-kb deletion in the S component of the HCMV genome (including open reading frames IRS1–US9 and US11) which failed to down regulate class I heavy chains. By examining the phenotypes of mutants with smaller deletions with this portion of the HCMV genome, a 7-kb region containing at least 9 open reading frames was shown to contain the genes required for reduction in heavy chain expression. Furthermore, it was determined that two subregions (A and B) of the 7-kb region each contained genes which were sufficient to cause heavy chain down regulation. In subregion B, the US11 gene product is involved. It encodes a endoglycosidase H-sensitive glycoprotein which is intracytoplasmic, similar to the adenovirus type 2 E3-19K glycoprotein which inhibits surface expression of class I heavy chains.

4 Claims, 17 Drawing Sheets

RV798 (US2-US11 DELETED)

PERMEABILIZED

AD169 (WT) 8h p.i.

NONPERMEABILIZED

AD169 (WT) 8h p.i.

RV699 8h p.i.

RV699 8h p.i.

IDENTIFICATION OF A HUMAN CYTOMEGALOVIRUS GENE REGION INVOLVED IN DOWN-REGULATION OF MHC CLASS I HEAVY CHAIN EXPRESSION

FIELD OF THE INVENTION

The present invention relates to recombinant mutant human cytomegalovirus (HCMV) which does not down regulate expression of cellular MHC class I heavy chains upon infection.

BACKGROUND OF THE INVENTION

Human cytomegalovirus (HCMV) is a betaherpesvirus which causes clinically serious disease in immunocompromised and immunosuppressed adults, as well as in some infants infected in in utero or perinatally (Alford and Britt, 1990). The 230-kb dsDNA genome of HCMV was sequenced (Chee et al., 1990) and has at least 200 open reading frames (ORFs). For purposes of this application, open reading frame is defined as the portion of a gene which encodes a string of amino acids and hence may encode a protein. The function of some HCMV proteins are known or predicted due to their homology with other viral (esp. herpes simplex virus) and cellular proteins. However, for the majority of the HCMV ORFs, the function(s) of the proteins they encode is unknown.

In order to study HCMV gene function HCMV deletion mutants can be constructed in order to assess their in vitro growth properties (Jones et al., 1991; Jones and Muzithras, 1992). For purposes of this application deletion mutants are defined as human cytomegalovirus mutants which lack regions of the wild-type viral genome. This strategy involves site-directed replacement mutagenesis of selected HCMV gene(s) by a prokaryotic reporter gene, usually β-glucuronidase, although guanosine phosphoribosyltransferase can also be used. In this fashion, the recombinant virus can be isolated only if the replaced viral gene(s) is nonessential.

Several investigators have shown that infection by HCMV results in the down regulation of cellular MHC class I heavy chains (Browne et al., 1990; Beersma et al., 1993; Yamashita et al., 1993). For purposes of this application, down regulation is defined as reduction in either synthesis, stability or surface expression of MHC class I heavy chains. Such a phenomenon has been reported for some other DNA viruses, including adenovirus, murine cytomegalovirus, and herpes simplex virus (Anderson et al., 1985; Burget and Kvist, 1985; del Val et al., 1989; Campbell et al., 1992; Campbell and Slater, 1994; York et al., 1994). In the adenovirus and herpes simplex virus systems, the product of a viral gene which is dispensable for replication in vitro is sufficient to cause down regulation of MHC class I heavy chains (Anderson et al., 1985; Burget and Kvist, 1985). The gene(s) involved in class I heavy chain down regulation by murine cytomegalovirus have not yet been identified.

SUMMARY OF THE INVENTION

The present invention is directed to a recombinant mutant human cytomegalovirus which does not down regulate expression of cellular MHC class I heavy chains upon infection. Mutants RV 798 and RV 799 both deleted of open reading frames US2–US11, lose the ability to down regulate MHC class I heavy chains.

The present invention is also directed to a method to produce the recombinant mutant human cytomegalovirus and a vaccine which utilizes the cytomegalovirus. One skilled in the art will use live attenuated HCMV vaccine lacking this gene region in order to elicit a better immune response, than one containing this gene region, based on the lack of class I down registration by the former. Therefore a virus lacking the region is a superior immunogen.

In addition, the HCMV gene involved in the MHC class I heavy chain down regulation can be incorporated into adenovirus vectors or similar virus based gene therapy vectors to minimize the immune response which will allow the use of the recombinant adenovirus or similar virus based gene therapy vectors to be used in gene therapy.

The invention may be more fully understood by reference to the following drawings.

BRIEF DESCRIPTION OF THE DRAWINGS

FIG. 2A is a Western blot analysis. HFF cells were uninfected (U) or infected at a multiplicity of infection of 5 PFU/cell. At 24, 48, and 72 h postinfection total cellular proteins were harvested, electrophoresed through a 15% SDS-polyacrylamide gel, electroblotted to nitrocellulose, and probed with TP25.99 murine monoclonal antibody (specific for a non-conformational epitope on MHC class I heavy chains) using an ECL chemiluminescent detection kit (Amersham). FIGS. 2B and C are immunoprecipitation analyses. HFF cells were uninfected or infected (as above), either in the absence or presence (+PFA) of phosphonoformate and radiolabeled either for 4 h at late times postinfection (69–73 h) FIG. 2B or for 2 h at the indicated time postinfection FIG. 2C. Proteins were harvested immediately after radiolabeling and class I heavy chains were immunoprecipitated using TP25.99 murine monoclonal antibody.

FIG. 3A, the; first line, is a schematic of the overall organization of the HCMV wild-type genome. Unique region sequences are shown by a line, while repeated region sequences are indicated by shaded boxes. Relevant HindIII fragments, within the L and S components, are indicated by letter designation (Oram et al., 1982). The second line is an expansion of the wild-type HindIII-Q, -X, and -V regions of the S component. The significant open reading frames, and their orientation, are shown as open boxes (Chee et al., 1990). The position of the IRs repeated sequences is indicated by the shaded rectangle. The locations of HindIII (H) and XhoI (X) restriction endonuclease sites are shown. FIGS. 3B–I show the genomic organization of the indicated HCMV mutant. In each case, the first line is the organization of the AD169 wild-type genome, the second line represents the organization of relevant sequences of the linearized plasmid used to make the recombinant virus. The slanted lines indicate the boundaries of the viral flanking sequences which may be involved in homologous recombination to create the desired mutation. The region deleted is indicated by a shaded box below the first line. FIG. 3J shows the derivation and organization of RV799. The first two lines are the same representations as FIGS. 3B–I, and the third line represents the organization of the relevant sequences of the linearized plasmid used to make RV799 from the RV134 parent (second line).

FIG. 4A is a radiograph of Class I heavy which chains were immunoprecipitated using TP25.99 murine monoclonal antibody. FIG. 4B is a radiograph of total radiolabeled proteins to verify approximately equivalent radiolabeling efficiency. FIG. 4C is a radiograph to verify equal progression through the viral replicative cycle. UL80 proteins were immunoprecipitated using anti-assembly protein rabbit polyclonal antiserum.

FIG. 5A is a radiograph of Class I heavy which chains were immunoprecipitated using TP25.99 murine monoclonal antibody. Equivalent radiolabeling efficiency (FIG. 5B) and progression through the viral replicative cycle (FIG. 5C) were verified as described for FIG. 4B and 4C.

FIG. 7A is a radiograph of Class I heavy which chains were immunoprecipitated using TP25.99 murine monoclonal antibody. Equivalent radiolabeling efficiency (FIG. 7B) and progression through the viral replicative cycle (FIG. 7C) were verified as described for FIG. 4B–C.

FIG. 9A is a radiograph of Class I heavy chains were immunoprecipitated using TP25.99 murine monoclonal antibody. FIG. 9B is a radiograph in which, to verify approximately equal infection, the 72-kDa IE1 immediate-early protein was immunoprecipitated using the murine monoclonal antibody 9221. FIG. 9C is a radiograph of the immunoprecipitation of the cellular transferrin receptor with murine monoclonal antibody Ber-T9 to verify approximately equal expression of this glycoprotein. FIG. 9D is a radiograph of total radiolabeled proteins to verify approximately equivalent radiolabeling efficiency.

In FIG. 10A, the first line is the overall organization of the HCMV wild-type genome, and the second line is an expansion of the wild-type HindIII-Q and -X regions of the S component. The ORFs are indicated by an unshaded rectangle; the unlabeled ORF overlapping US4 and US5 is US4.5 in FIG. 10(B), the deletions within the various HCMV mutants are indicated by the shaded rectangle. RV670 is deleted of IRS1–US9 and US11; RV35 is deleted of US6–US11; RV67 is deleted of US10–US11; RV80 is deleted of US8–US9; RV725 is deleted of US7; RV69 is deleted of US6; RV47 is deleted of US2–US3; RV5122 is deleted of US1; RV46 is deleted of IRS1; RV798 is deleted of US2–US11; RV7181 is deleted of IRS1–US9; RV7177 is deleted of IRS1–US6; and RV7186 is deleted of IRS1–US11. MHC class I heavy chain down regulation results are from immunoprecipitation experiments (using the heavy chain conformation-independent monoclonal antibody, TP25.99) in which HCMV-infected HFF cells were radiolabeled at late times postinfection. FIG. 10C shows location of the two subregions which contain gene(s) which are sufficient for MHC class I heavy chain down regulation. Subregion A contains ORFs US2–US5 (bases 193119–195607 Set forth in SEQ. ID NO:1) and subregion B contains ORFs US10 and US11 (bases 199083–200360 Set forth in SEQ. ID NO:2).

DESCRIPTION OF THE PREFERRED EMBODIMENTS

A recombinant HCMV mutant called RV670, has been constructed which expresses a marker gene (β-glucuronidase) in place of a group of viral genes. Upon infection of human fibroblast cells with this mutant, it is demonstrated that expression of the major histocompatibility complex (MHC) class I heavy chains are not reduced, as it is when wild-type HCMV infects these cells.

Unlike wild-type HCMV, the present invention's virus does not result in the down regulation of cellular MHC class I heavy chain protein expression. A 7kb region of the HCMV genome which contains genes which are required for down regulation of heavy chain expression is utilized in the invention.

One skilled in the art will appreciate that efficient antigen processing and presentation is required to activate and expand cytotoxic T-Lymphocyte precursors for an efficient cell mediated immune response. Efficient viral antigen presentation requires the continued expression of MHC class I proteins throughout infection. Infection of cells with RV670 results in continued expression of class I heavy chains.

One skilled in the art will appreciate that the claimed virus (RV670) or another human cytomegalovirus with a deletion of similar genes, can be utilized to produce an effective live vaccine since class I heavy chains are still expressed in RV670-infected cells, as they are in uninfected cells, and therefore viral antigen presentation, for the purpose of initiating a cytotoxic T cell response occurs.

Figure 1A:
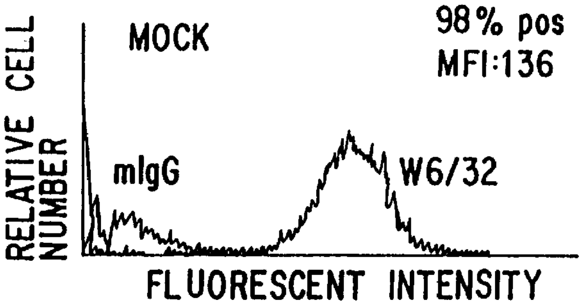
FIGS. 1A–1E Detection of cell surface MHC class I by inmuunofluorescence-flow cytometry in HCMV-infected cells. Human foreskin fibroblast (HFF) cells were infected with the indicated virus at a multiplicity of infection of 5 PFU/cell for 72 h. At that time, cells were fixed in 1% paraformaldehyde and stained with primary antibody specific for HLA-A, B, C (W6/32) or control mouse IgG (isotype matched) followed by secondary FITC-conjugated goat anti-mouse IgG. Percent positive cells ($5\times10^3$ total) and mean fluorescent intensity (MFI) were calculated on the basis of forward angle light scatter versus log-integrated 90° light scatter using the Immuno Program, Coulter MDADS I.
Figure 1B:
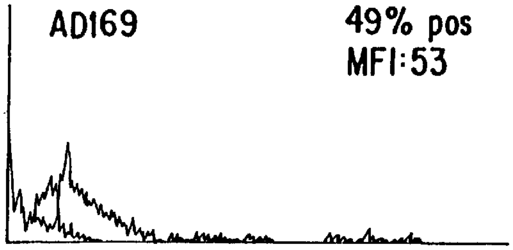
Figure 1C:
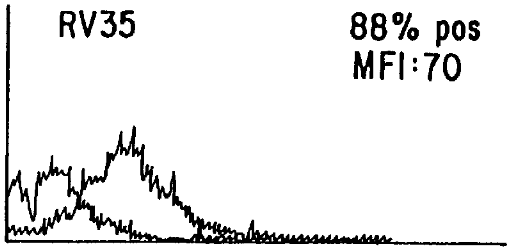
Figure 1D:
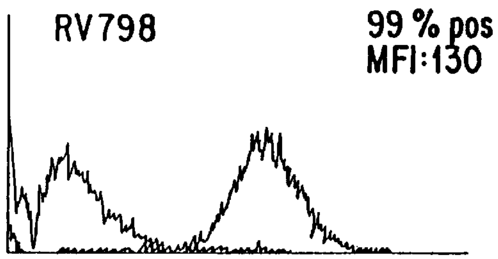
Figure 1E:
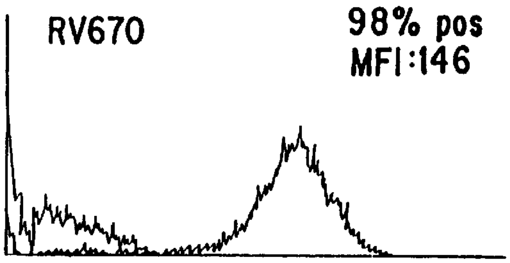
Figure 2A:
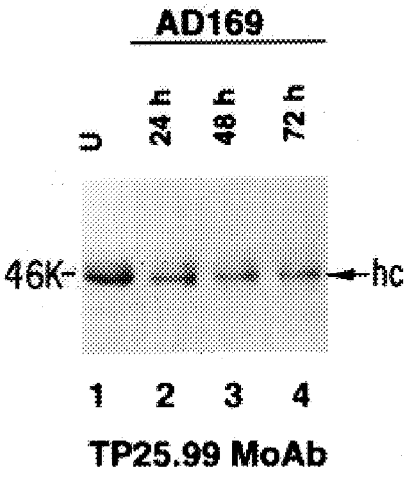
FIGS. 2A–2C Expression of MHC class I heavy chains in HCMV wild-type strain AD169-infected cells.
Figure 2B:
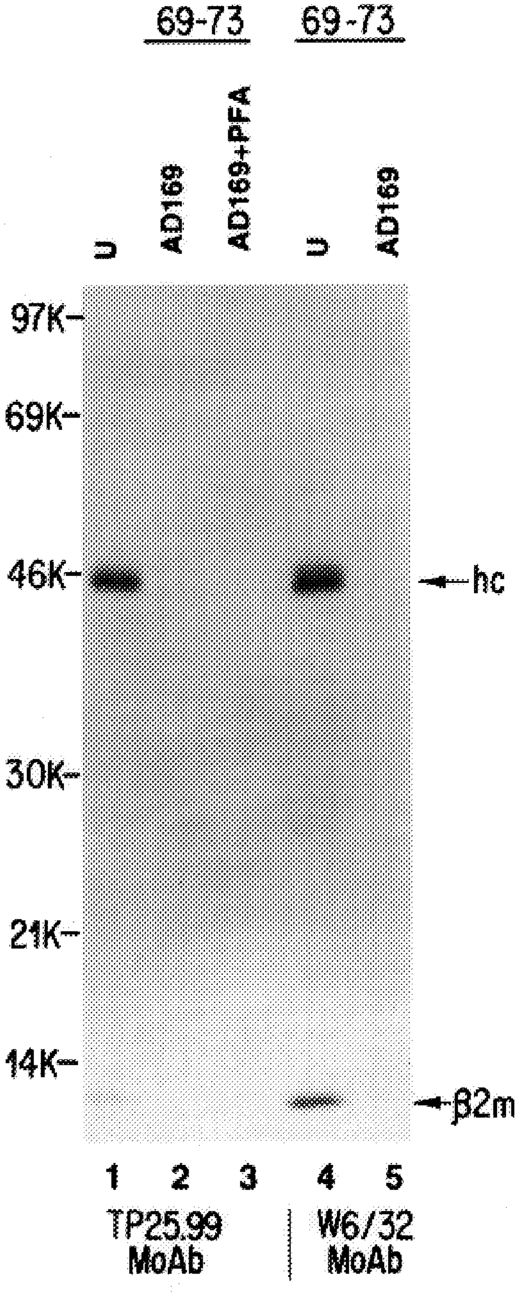
Figure 2C:
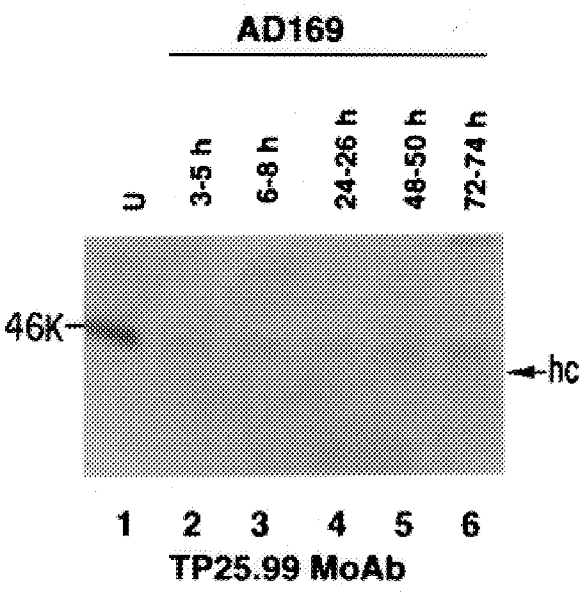
Figure 3A:
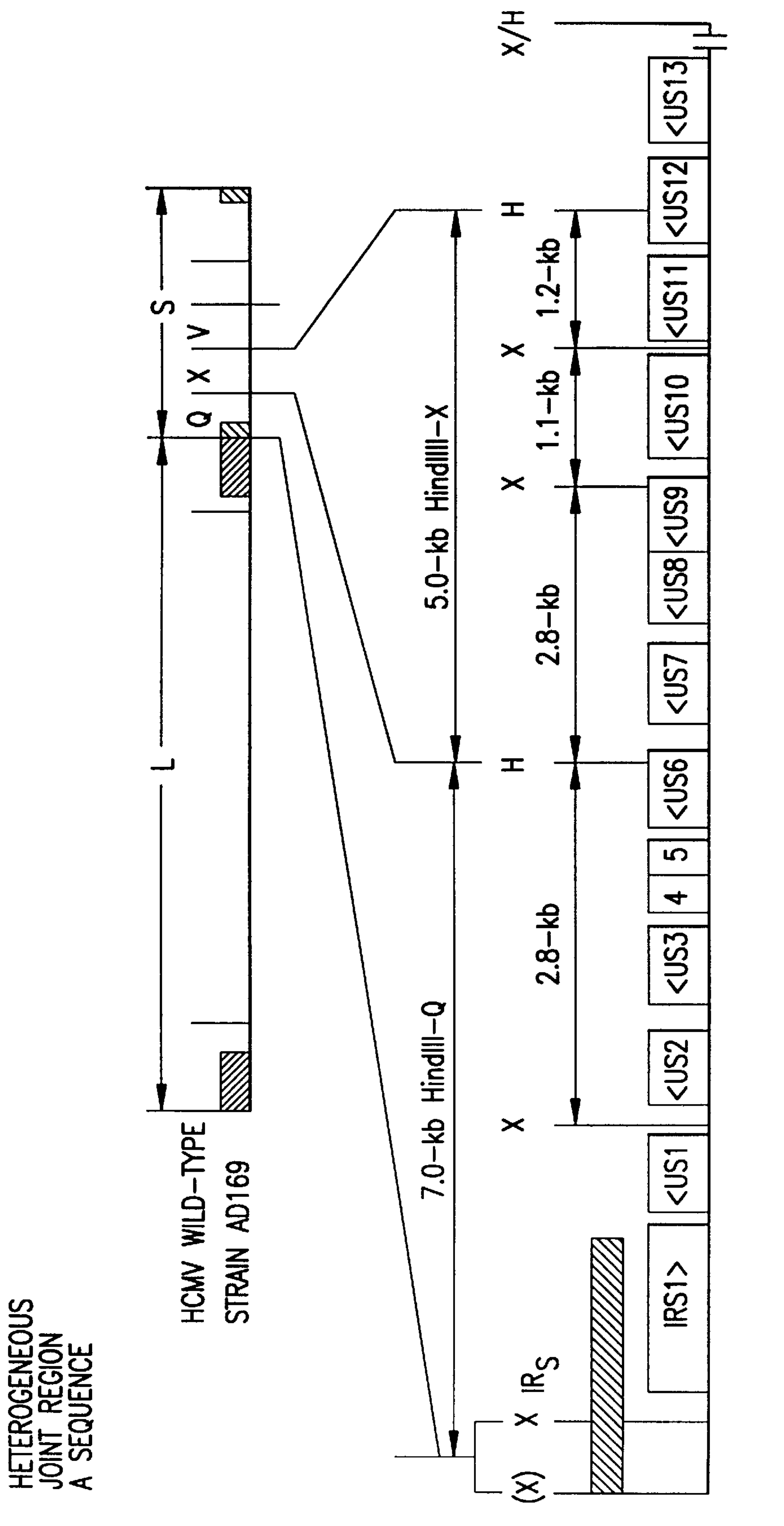
FIGS. 3A–3J Organization of recombinant virus genomes.
Figure 3B:
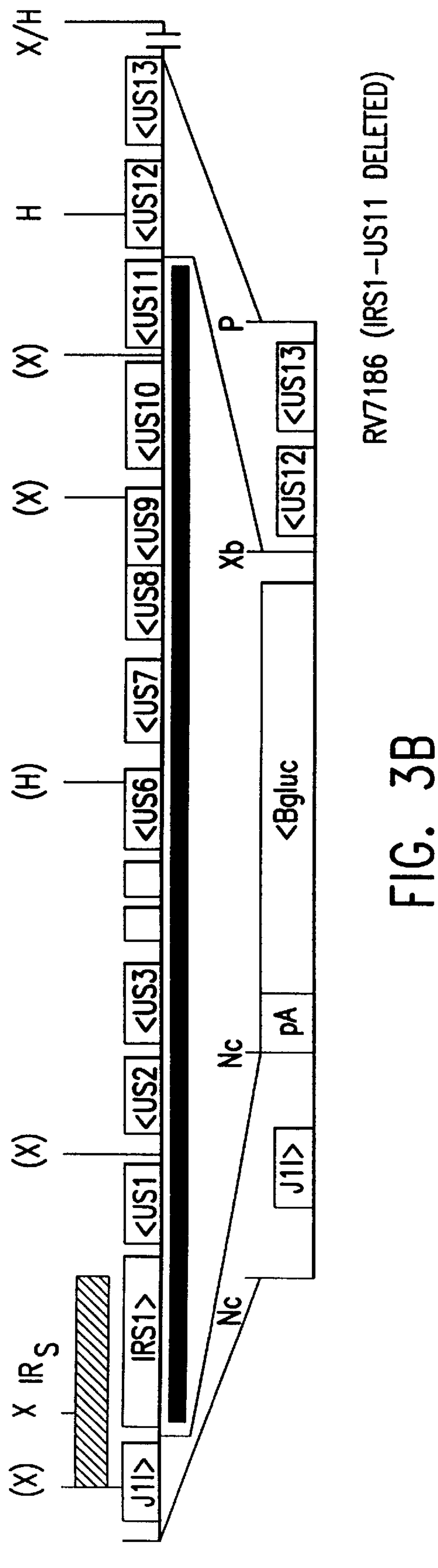
Figure 3C:
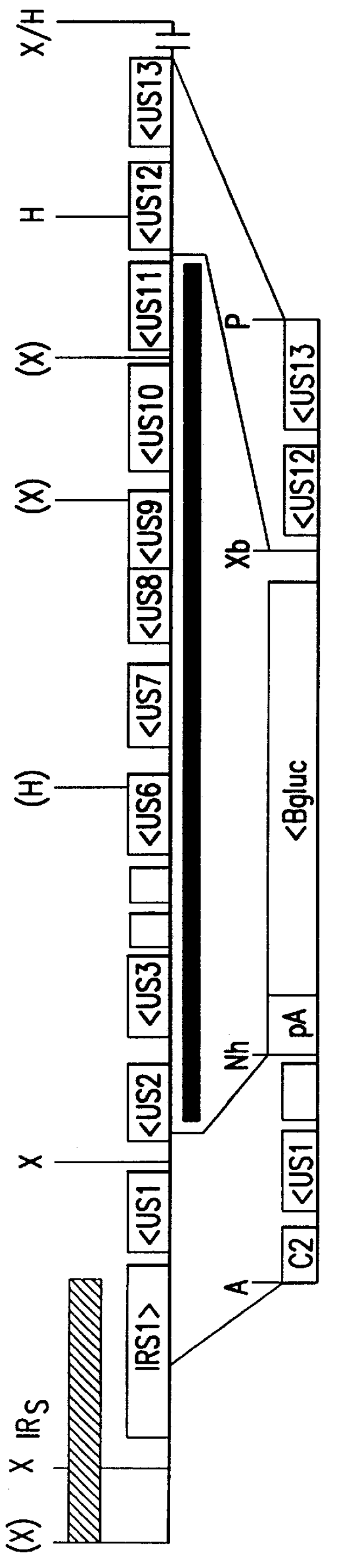
Figure 3D:
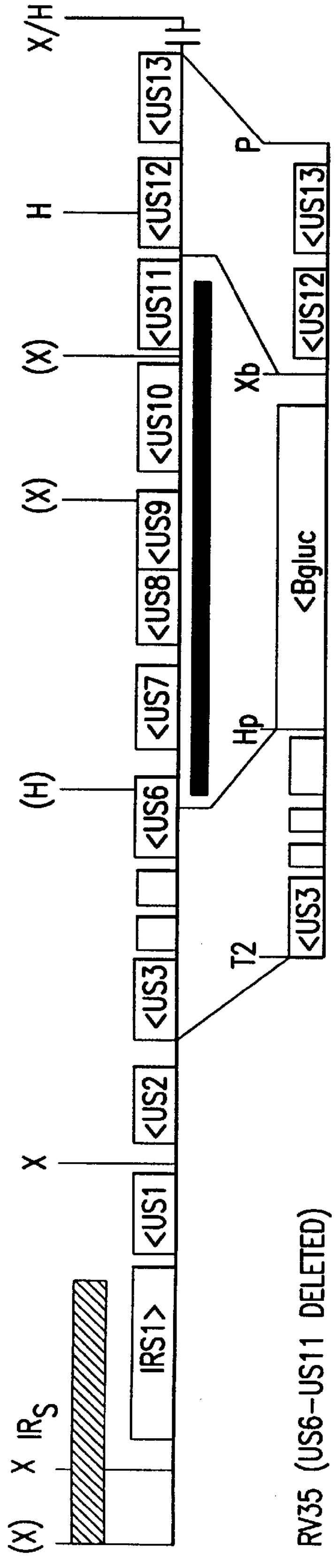
Figure 3E:
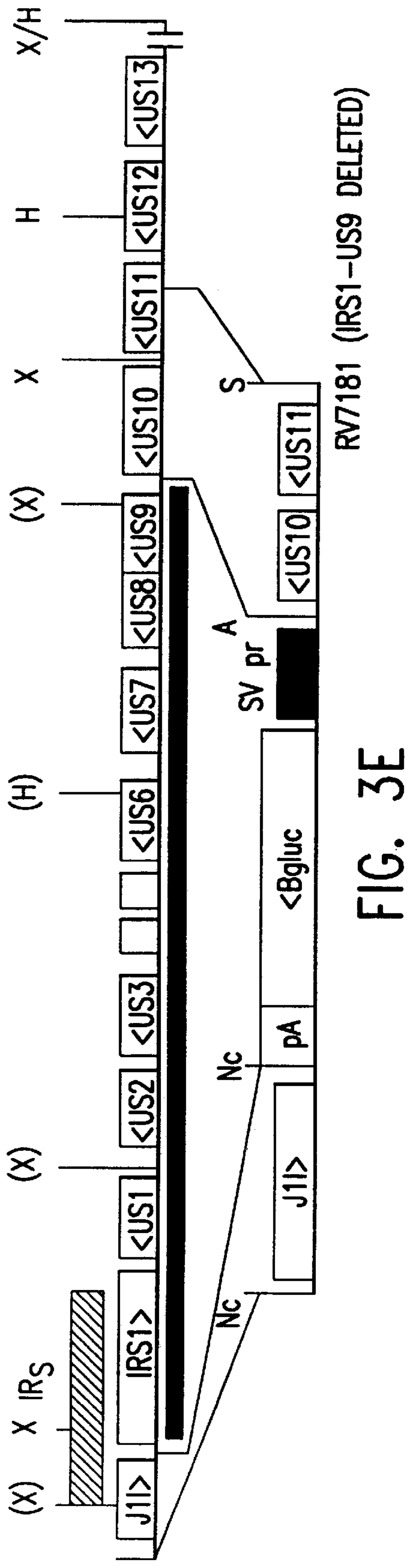
Figure 3F:
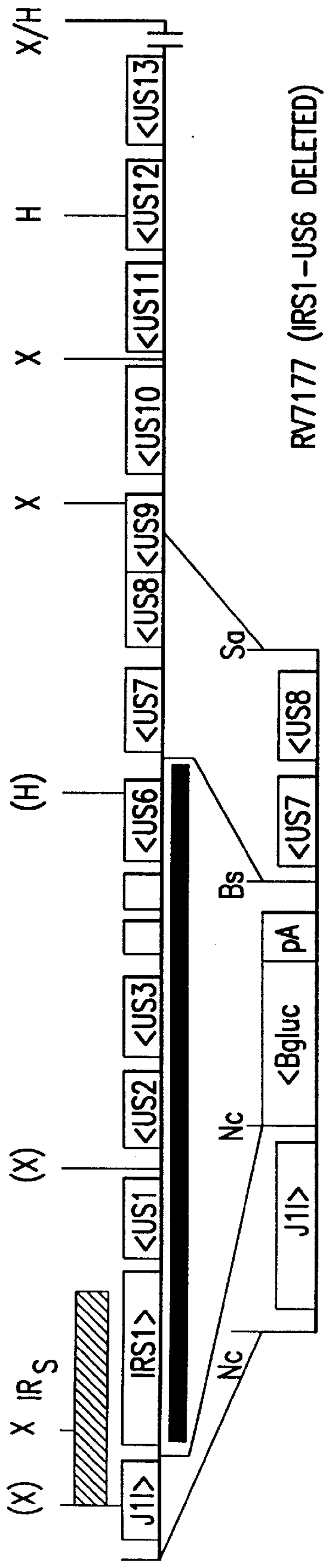
Figure 3G:
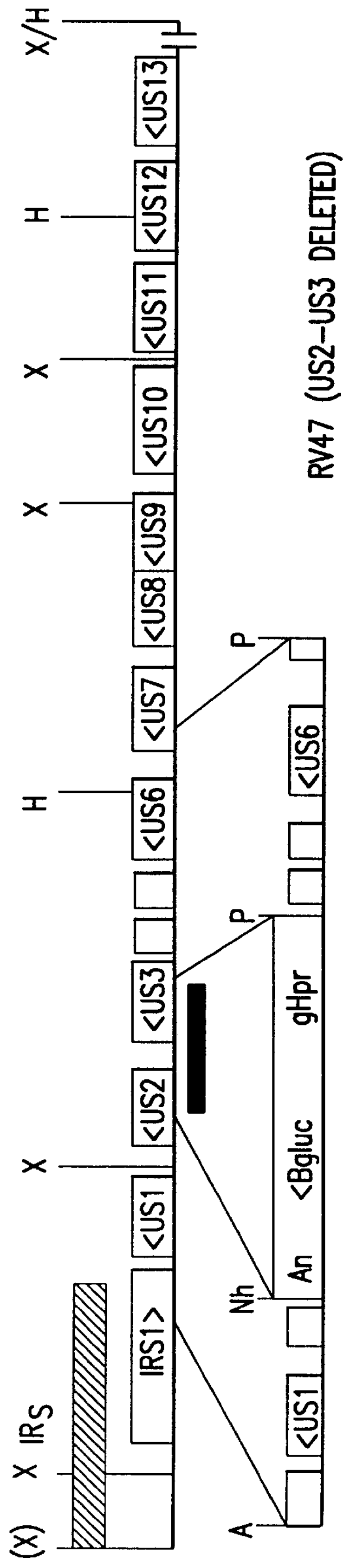
Figure 3H:
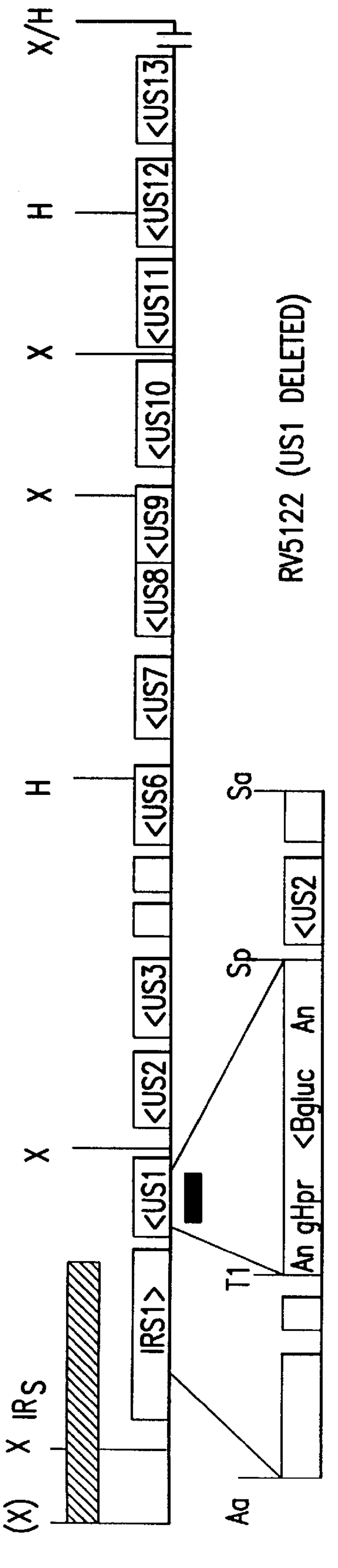
Figure 3I:
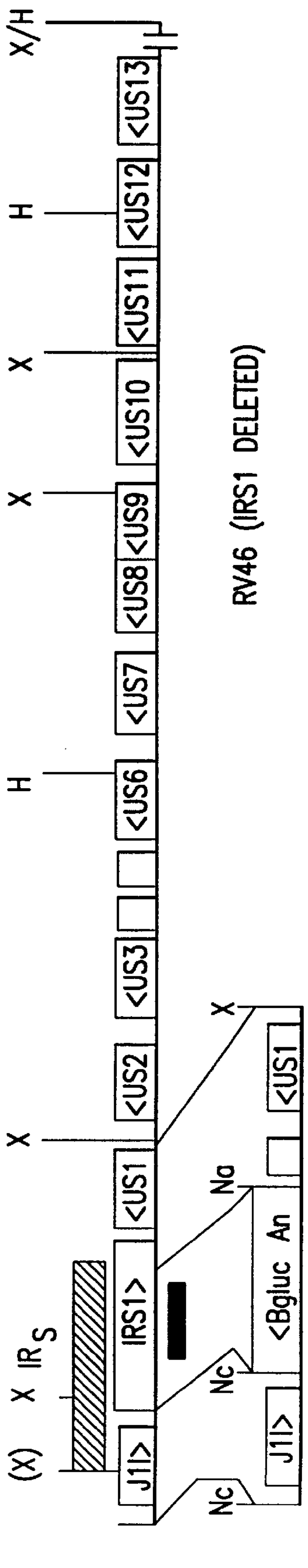
Figure 3J:
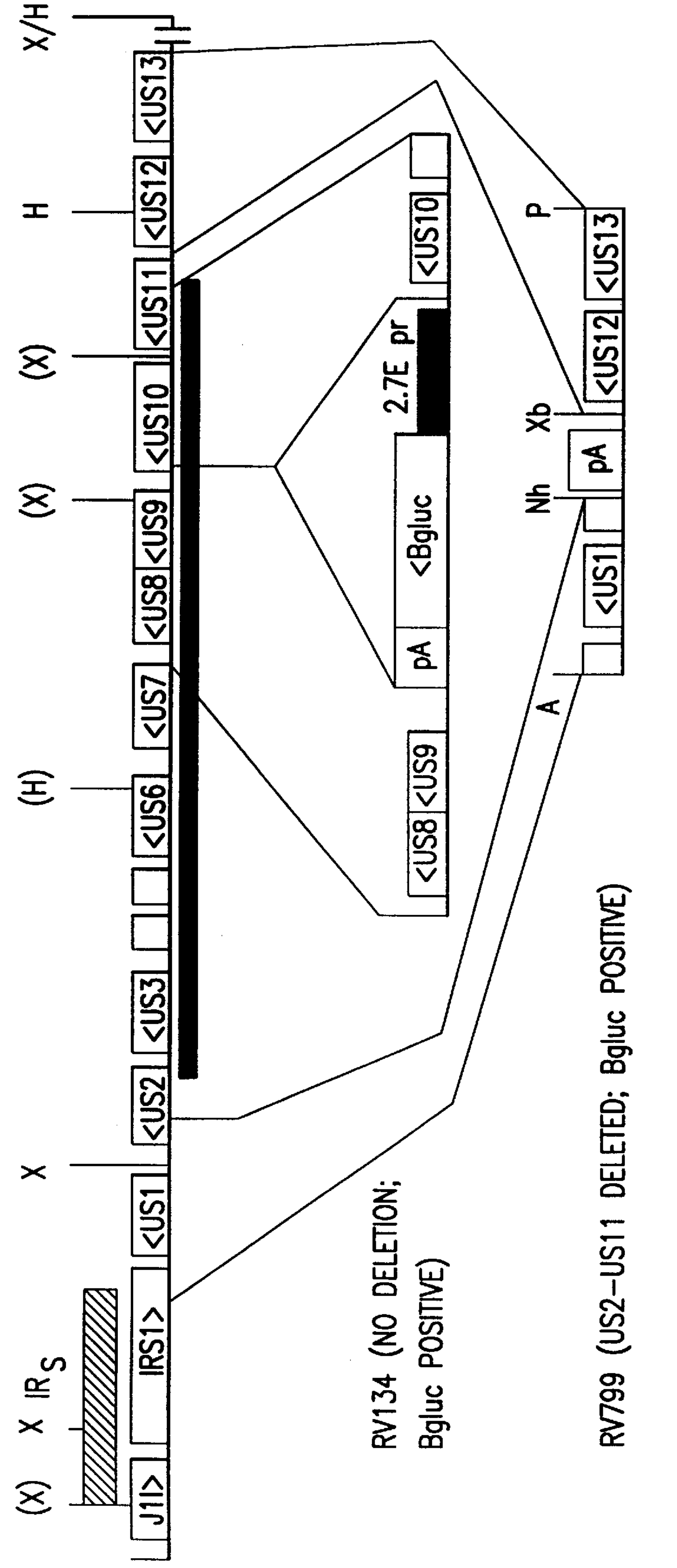

In the present invention, flow cytometry and immunofluorescence experiments confirmed that cell surface expression of class I heavy chains are greatly reduced at late times postinfection in HCMV wild-type strain 8169 infected HFF cells. Radiolabeling-immunoprecipitation experiments indicates that down regulation of newly synthesized MHC class I heavy chains occurs throughout the course of infection, beginning at very early times (3 h) postinfection (FIG. 2C). This reduction has been reported to be at the post-translational level: class I heavy chains have a higher turnover rate in HCMV-infected cells than in uninfected cells (Beersma et al., 1993). Such instability of class I heavy chains results in a reduced cell mediated immune response to HCMV infection since viral peptides will be inefficiently presented. Thus, the reduction in class I heavy chain expression is important in terms of evasion of host's immune system in the establishment of persistent or latent infections by HCMV (Gooding, 1992).

Figure 10:
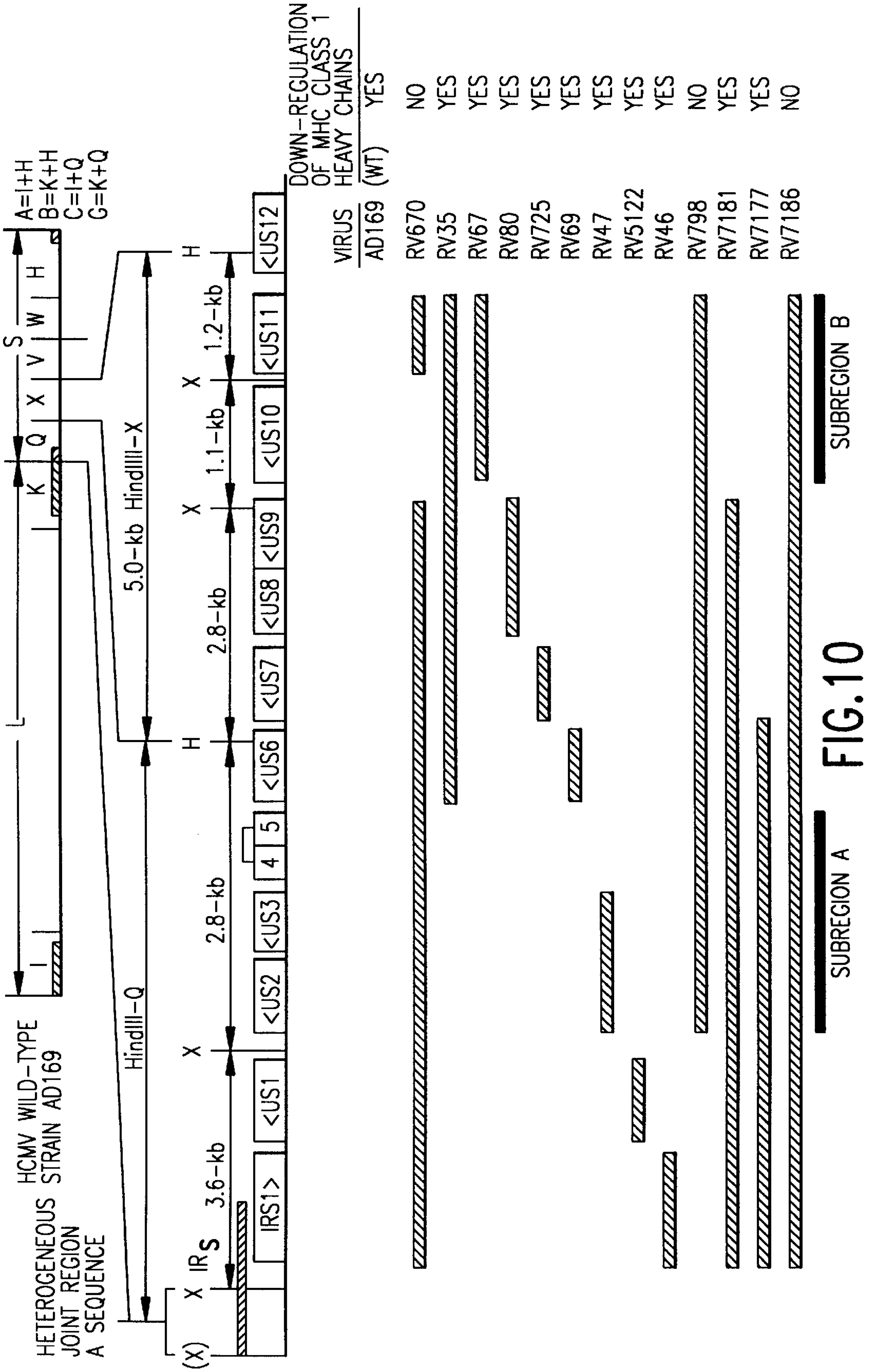
FIGS. 10 provides a summary of MHC class I heavy chain expression data from HFF cells infected with wild-type and mutant HCMV.

We screened our bank of HCMV mutants which represent 18 ORFs which are dispensable for viral replication in tissue culture for their ability to cause down regulation of MHC class I heavy chains. A 7-kb region of the S component of the HCMV genome, containing ORFs US2–US11 (bases 193119–200360 Set forth in SEQ. ID NO:3), is clearly shown to contain genes which are required for this phenotype (data summarized in FIG. 10). Within this region, there are two subregions, each of which contain genes sufficient for heavy chain down regulation. Subregion A contains ORFs US2-US5 (bases 193119–195607 Set forth in SEQ. ID NO:1). It is proposed that US2 and US3 encode membrane glycoproteins (Chee et al., 1990). US3 is a differentially spliced gene which is expressed throughout the viral replicative cycle and encodes a protein with transcriptional transactivating function (Tenney and Colberg-Poley, 1991; Colberg-Poley et al., 1992; Tenney et al., 1993; Weston, 1988). Several smaller ORFs are also present in this subregion (between the ORFs US3 and US5), but their expression characteristics or functions have not been reported. Gretch and Stinski (1990) reported that there is a 1.0-kb early mRNA transcribed from this region of the HCMV genome, but it was not fine-mapped. It is not yet known which of these genes are involved in heavy chain down regulation.

Figure 11A:
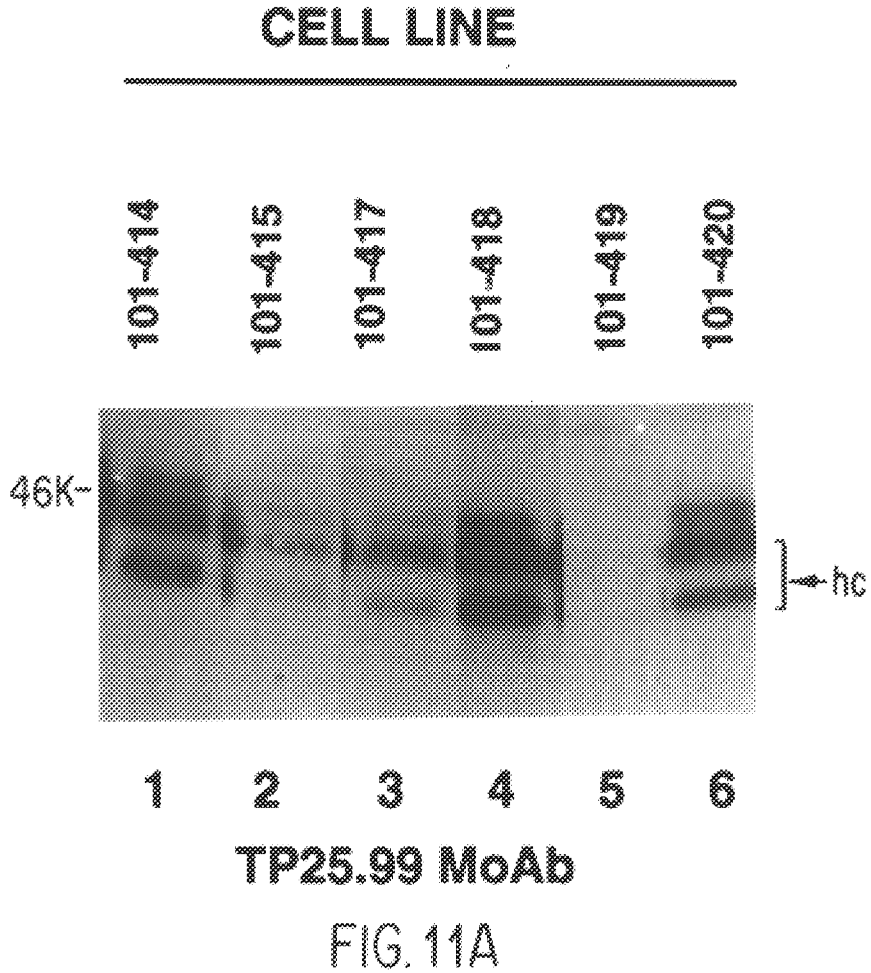
FIG. 11A–11B are western blots of cell lines expressing the HCMV US11 gene. Uninfected human U373-MG astrocytoma cells stably transformed with a US11 expression plasmid were analyzed by Western Blot analysis for MHC class I heavy chain expression (FIG. 11A) and for US11 expression (FIG. 11B) using the TP25.99 monoclonal antibody and the US11 polyclonal antisera, respectively.
Figure 11B:
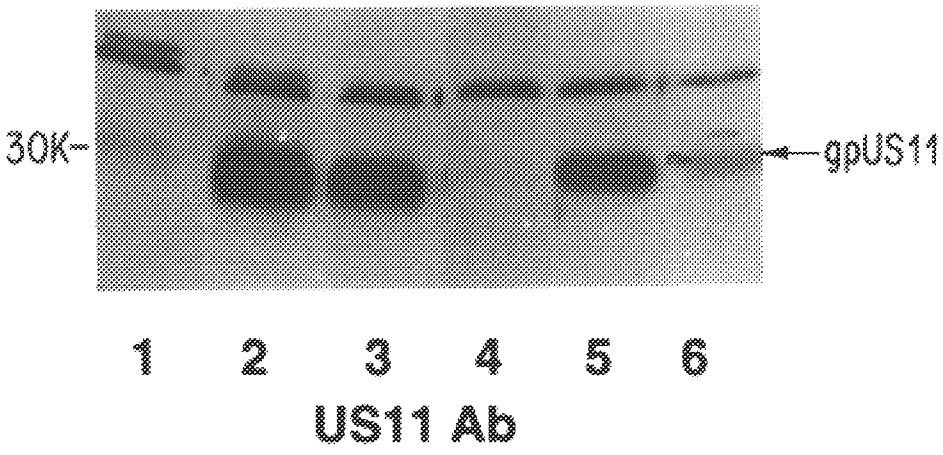

Subregion B is also sufficient for MHC class I heavy chain reduction contains the US10 and US11 genes (FIG. 10), bases 199083–200360 Set forth in SEQ. ID NO:2. However, based on data using HCMV mutant RV670, which expresses wild-type levels of the US10 gene product (Jones et al., manuscript in preparation), US10 expression is not sufficient for down regulation of heavy chain expression (FIG. 2B). Thus, the genetic data implicates the US11 gene product as being required. We have demonstrated that US11 expression is sufficient to cause MHC class I heavy chain down regulation in stably transformed uninfected cells in the absence of other MCNV proteins (FIG. 11). RNA and protein expression from both of these ORFs begins early and proceeds throughout the course of infection (Jones and Muzithras, 1991); US10 and US11 encode glycoproteins of 22-kDa (gpUS10) and 32-kDa, (gpUS11) respectively; both glycoproteins have N-linked sugar residues which are completely endoglycosidase H sensitive. These glycoproteins are retained in the endoplasmic reticulum or cis golgi. Consistent with this conclusion is the immunofluorescence data in which gpUS11 was not detected on the cell surface, but was detected in the cytoplasm of HCMV-infected cells (FIG. 8). The characteristics of HCMV gpUS11 (as well as gpUS10) are similar to the 25-kDa glycoprotein (E3–19K) encoded from the E3 region of adenovirus type 2. Ad E3–19K is nonessential for viral replication. It has been shown to contain endoglycosidase H-sensitive N-linked sugar residues, be retained in the endoplasmic reticulum, and bind MHC class I heavy chains; thereby preventing their transport to the cell surface 9 (Anderson et al., 1985; Burgert and Kvist, 1985). In contrast to Ad E3–19K, a direct association between gpUS11 (or gpUS10) and class I heavy chains (i.e. by coimmunoprecipitation) was not detected (data not shown).

The identification of US2–US11 gene region as the region of the HCMV genome required for down regulation of MHC class I heavy chains is significant in several respects. As mentioned above, expression from this region of the genome throughout the course of infection acts to interfere with an effective cell mediated immune response. Surface expression of MHC class I molecules is required for antigen presentation to activate and expand cytotoxic T lymphocyte (CTL) precursors populations (Schwartz, 1985). In addition, they are further required for target recognition by the activated CTLs (Zinkernagel and Doherty, 1980). In MCMV, CTLs against the major immediate-early protein are protective against lethal infection by this virus (Jonjic et al., 1988). However, in HCMV infected individuals, the frequency of CTLs against the analogous HCMV immediate-early protein, IE1, are reported to be extremely rare (Gilbert et al., 1993). Recent studies have shown that IE peptides are more efficiently presented by interferon-γ-treated HCMV-infected cells, than by untreated infected cells (Gilbert et al., 1993). Interferon $\mu$ causes increased surface expression of MHC class I proteins. Thus, increasing the expression of class I heavy chains in HCMV-infected cells may be important in the efficient generation of IE-specific CTLs, or CTLs against other important HCMV antigens. A HCMV mutant deleted of the US2–US11 gene region would have this effect since the class I heavy chains are not down regulated when cells are infected with this mutant. Therefore, a deletion of this region of the viral genome is important in the development of an live HCMV vaccine to induce an effective anti-HCMV immune response.

Several years ago it was reported that the HCMV UL18 ORF encoded a protein which resembled MHC class I heavy chains (Beck and Barrell, 1988). It was hypothesized that the down regulation of heavy chains in HCMV-infected cells was due to competition of the UL18 gene product for β2-microglobulin, which effectively prevented the normal association of class I heavy chains and β2-microglobulin (Browne et al., 1990). This hypothesis was essentially dispelled when a HCMV mutant deleted of UL18 retained its ability to down regulate heavy chain expression (Browne et al., 1992). It remained possible that the UL18 gene product was only one of several HCMV genes whose expression is sufficient for this phenotype. However, the present invention data indicates that only genes within the US2–US11 region are sufficient for class I heavy chain down regulation.

The existence of two independent mechanisms which result in down regulation of MHC class I expression emphasizes the importance of this phenotype for successful infection and persistence in the host. One mechanism may serve as a backup system for the other, but also plausible is that there is cell type specificity for each system. In the case of the HFF cell system, both mechanisms are functional. However, in U373-MG cells, down regulation of heavy chain expression is more dependent on the presence of the subregion A. In that case, there may be qualitative or quantitative differences in cellular proteins which interact with subregion B gene products. A similar situation exists in the herpes simplex virus system. It was recently reported that the 88 amino acid US12 gene product (ICP47) is sufficient for class I heavy chain sequestering in the endoplasmic reticulum (York et al., 1994). However, expression of heavy chains is not affected in herpes simplex virus-infected mouse cells, although ICP47 is expressed in those cells and murine heavy chains are down regulated when expressed in an HSV-infected human fibroblast system (York et al., 1994).

A pharmaceutical composition may be prepared containing the recombinant HCMV mutant of the present invention in which the genome is devoid of a gene sequence capable of down regulating MHC Class I expression in infected cells. A stabilizer or other appropriate vehicle may be utilized in the pharmaceutical composition.

As discussed earlier, the recombinant HCMV mutant of the present invention which is devoid of the gene sequence capable of down regulating MHC Class I expression may be used in a vaccine for the prevention of cytomegalovirus infections. The vaccine comprises an effective amount of the recombinant HCMV mutant in a pharmaceutically acceptable vehicle. An adjuvant may be optionally added to the vaccine.

A method of immunizing an individual against cytomegalovirus may be carried out by administering to the individual an immunogenic amount of the recombinant HCMV mutant of the present invention which is devoid of the gene sequence capable of down regulating MHC Class I expression.

A method of preventing or reducing susceptibility in an individual to acute cytomegalovirus may be carried out by administering to the individual an immunogenic amount of the recombinant HCMV mutant of the present invention which is devoid of the gene sequence capable of down regulating MHC Class I expression.

Down regulation of MHC Class I expression in a cytomegalovirus infected cell may be controlled by a method having the steps of identifying a gene sequence capable of down regulating the major histocompatibility complex and deleting the identified gene sequence from the cytomegalovirus genome.

As discussed earlier, the gene sequence involved in the MHC Class I heavy chain down regulation can be incorporated into adenovirus vectors or similar virus based gene therapy vectors to minimize the immune response and allow the use of the vectors in gene therapy. One virus based gene therapy vector comprises the gene sequence of the open reading frame of US11. Another virus based gene therapy vector comprises the gene sequences of subregions A and B (open reading frames US2–US5 and US10–US11 , respectively).

EXAMPLE 1

Virus and Cells. HCNV strain AD169 is obtained from the American Type Culture Collection and propagated according to standard protocols known by those skilled in the art. Human foreskin fibroblast (HFF) cells were isolated in this laboratory and used below passage twenty (Jones and Muzithras, 1991). They were grown in Dulbeccos modified Eagle medium (DMEM) containing 10% fetal bovine serum and 25 mM HEPES.

DNA sequence. The numbering system of Chee et al. (1990) of the HCMV strain AD169 DNA sequence (Genbank accession number X17403) is used in the present invention.

Plasmids. Plasmids used for creation of HCMV mutants are constructed using the method described previously (Jones et al., 1991; Jones and Muzithras; 1992). Generally, the β-glucuronidase reporter gene is surrounded on each side by 1.5-kb of HCMV sequences which flank the gene(s) to be deleted from the virus. In each case, the plasmid DNA is linearized with a restriction enzyme which cuts within the prokaryotic backbone prior to transfection. The HCMV strain AD169 genomic DNA fragments are derived from either pHind-G, pHind-X, or pXba-P which contain the HindIII-G (bases 176844 to 195837 Set forth in SEQ. ID NO:4), -X (bases 195837 to 200856 Set forth in SEQ. ID NO:5), and XbaI-P (bases 200391 to 206314 Set forth in SEQ. ID NO:6) DNA fragments, respectively (Oram et al., 1982; Jones et al., 1991). pUS7/US3 contains the 1.7-kb PstI-PstI HCMV fragment (bases 194741 to 196447 Set forth in SEQ. ID NO:7; in pIBI30 vector [International Biotechnologies, Inc.]) derived from pHind-G and pHind-X.

To replace HCMV ORFs US11 through IRS1 by β-glucuronidase (i.e. RV7186; FIG. 3), pBgdUS11/IRS1 are constructed. Sequentially, this plasmid contains the 1.8-kb fragment PstI-XbaI fragment (bases 200391 to 202207 Set forth in SEQ. ID NO:8; containing US13, US12, and US11 promoter sequences; from pXba-P), β- glucuronidase, a 288-b SV40 fragment containing the early and late polyadenylation signals (from pRcCMV [Invitrogen]), and the 1.7-kb NcoI-NcoI fragment (bases 188062 to 189763 Set forth in SEQ. ID NO:9; containing J1I to IRL1 sequences; from pHind-G).

To replace HCMV ORFs US11 through US2 by β-glucuronidase (i.e. RV798; FIG. 3), pBgdUS11/US2 are constructed. Sequentially, this plasmid contains the 1.8-kb fragment PstI-XbaI fragment (bases 200391 to 202207 Set forth in SEQ. ID NO:8; containing US13, US12, and US11 promoter sequences; from pXba-P), β-glucuronidase, a 255-b fragment containing the US10 polyadenylation signal (bases 199021 to 199276 Set forth in SEQ. ID NO:10; from pHind-X), and the 1.3-kb NheI-ApaI fragment (bases 192033 to 193360 Set forth in SEQ. ID NO:11; containing C-terminal US2 to IRS1 sequences; from pHind-G).

To replace HCMV ORFs US11 through US6 by β-glucuronidase (i.e. RV35; FIG. 3), pBgdUS11/US6 was constructed. Sequentially, this plasmid contains the 1.8-kb PstI-XbaI fragment (bases 200391 to 202207 Set forth in SEQ. ID NO:8; containing US13, US12, and US11 promoter sequences; from pXba-P), β-glucuronidase, and the 1.5-kb HpaI-SstII fragment (bases 194062 to 195589 Set forth in SEQ. ID NO:12; containing C-terminal US6 to US3 sequences; from pHind-G). Replacement of HCMV ORFs US11–US10, or ORF US11 (singly), by β-glucuronidase (i.e. RV67 and RV699, respectively) were described previously (Jones et al., 1991).

To replace HCMV ORFs US9 through IRS1 by β-glucuronidase (i.e. RV7181; FIG. 3), pBgdUS9/IRS1 was constructed. Sequentially, this plasmid contains the 1.1-kb SalI-ApaI fragment (bases 199021 to 200171 Set forth in SEQ. ID NO:13), the 351-b SV40 early promoter (from pRcCMV), β-glucuronidase, the 288-b SV40 polyadenylation signal fragment, and the 1.7-kb NcoI-NcoI fragment (bases 188062 to 189763 Set forth in SEQ. ID NO:9; containing J1I to IRL1 sequences; from pHind-G).

To replace HCMV ORFs US6 through IRS1 by β-glucuronidase (i.e. RV7177; FIG. 3), pBgdUS6/IRS1 was constructed. Sequentially, this plasmid contains the 1.7-kb NcoI-NcoI fragment (bases 188062 to 189763 Set forth in SEQ. ID NO:9; containing IRL1, J1I, and IRS1 promoter sequences; from pHind-G), β-glucuronidase, the 255-b fragment containing the US10 polyadenylation signal (bases 199021 to 199276 Set forth in SEQ. ID NO:10; from pHind-X), and the 1.8-kb BsmI-SauI fragment (bases 196222 to 198030 Set forth in SEQ. ID NO:14; containing US7 to C-terminal US9 sequences; from pHind-X).

To replace HCMV ORFs US3 and US2 by β-glucuronidase (i.e. RV47; FIG. 3), pBgdUS3/US2 was constructed. Sequentially, this plasmid contains the 1.7-kb PstI-PstI fragment (bases 194741 to 196447 Set forth in SEQ. ID NO:7), a 180-b SmaI-HaeIII fragment containing the HSV-1 gH promoter (McKnight, 1980), β-glucuronidase, the 255-b US10 polyadenylation signal fragment, and the 1.3-kb NheI-ApaI fragment (bases 192033 to 193360 Set forth in SEQ. ID NO:11; containing C-terminal US2 to IRS1 sequences; from pHind-G).

To replace HCMV ORF US1 by β-glucuronidase (i.e. RV5122; FIG. 3), pBgdUS1 was constructed. Sequentially, this plasmid contains the 1.8-kb AatII-SstI fragment (bases 190884 to 192648 Set forth in SEQ. ID NO:15;containing IRS1 and US1 C-terminal sequences; from pHind-G), a 180-b SmaI-HaeIII fragment containing the HSV-1 gH promoter (McKnight, 1980), β-glucuronidase, the 255-b US10 polyadenylation signal fragment, and the 1.6-kb SphI-SphI fragment (bases 192934 to 194544 Set forth in SEQ. ID NO:16; containing US2 and C-terminal US3 sequences; from pHind-G).

To replace HCMV ORF IRS1 by β-glucuronidase (i.e. RV46; FIG. 3), pBgdIRS1 was constructed. Sequentially, this plasmid contains the 1.7-kb NcoI-NcoI fragment (bases 188062 to 189763 Set forth in SEQ. ID NO:9; containing IRL1, J1l, and IRS1 promoter sequences; from pHind-G), β-glucuronidase, the 255-b fragment containing the US10 polyadenylation signal (bases 199021 to 199276 Set forth in SEQ. ID NO:10; from pHind-X), and the 1.2-kb NarI-XhoI fragment (bases 191830 to 193003 Set forth in SEQ. ID NO:17; containing C-terminal IRS1 and US1 sequences; from pHind-G). To delete HCMV ORFs US11 through US2 without insertion of a reporter gene (i.e. RV799; FIG. 3), pdUS11/US2 was constructed. Sequentially, this plasmid contains the 1.8-kb fragment PstI-XbaI fragment (bases 200391 to 202207 Set forth in SEQ. ID NO:8; containing US13, US12, and US11 promoter sequences; from pXba-P), β-glucuronidase, 65-b NruI-ApaI fragment containing the US10 polyadenylation signal (bases 199021 to 199086 Set forth in SEQ. ID NO:18; from pHind-X), and the 1.3-kb NheI-ApaI fragment (bases 192033 to 193360 Set forth in SEQ. ID NO:11; containing C-terminal US2 to IRS1 sequences; from pHind-G).

Isolation of recombinant mutant HCMV

Creation and isolation of recombinant mutant HCMV is done as described previously (Jones et al., 1991; Jones and Muzithras, 1992). HFF cells are split so that they are 70–80% confluent on the day of transfection. The cells are trypsinized and suspended to $5.6 \times 10^6$ cells per ml in DMEM/10% FCS/25 mM HEPES. The DNA is transfected using a modified calcium phosphate co-precipitation technique. 1.5 μg of infectious HCMV DNA and 2.5 μg of linearized plasmid DNA are mixed in the calcium chloride solution (300 μl containing 10 mM Tris pH 7.0/250 mM calcium chloride) and chilled on ice. To initiate the co-precipitation, the DNA is removed from the ice and 300 μl 2× HeBS pH 6.95 (at room temperature; 1× HeBS is 19.2 mM HEPES, 137 mM NaCl, 5 mM KCl, 0.8 mM sodium phosphate, 0.1% dextrose) is added dropwise with gentle mixing. After 1.5 min, the precipitate is placed on ice (to prevent further precipitate from forming). The precipitate is mixed with $3 \times 10^6$ cells (in suspension) and placed in a 82mm tissue culture plate. After 6 h at 37° C., the media is removed and the cells are shocked with 20% DMSO in 1× HeBS for 2 min. The cells are washed twice with PBS and growth media is added. The media is changed every 4–7 days. After 14 days, viral plaques are observed and the cells are overlaid with 0.5% agarose in DMEM containing 150 μg/ml X-gluc (5-bromo 4-chloro 3-indol 1-glucuronide; Biosynth). Blue plaques (i.e. β-glucuronidase-positive mutant virus plaques) are picked several days after adding the overlay. Recombinant viruses were plaque purified three times. HCMV mutant RV799 is β-glucuronidase-negative and is isolated using a modification of the above procedure. In this case, β-glucuronidase-positive HCMV mutant RV134 is the parent virus (Jones et al., 1991). Thus, RV134 genomic DNA is used instead of wild-type strain AD169 DNA in the transfections. Primary plaques appearing on the primary transfection plates are picked at random and replated on HFF cells. After 10 days, the media is removed and the infected cells are overlaid with X-gluc-containing agarose as described above. In this case, white plaques (β-glucuronidase-negative mutant virus plaques) are picked 4 days later and plaque purified. The proper genomic organization of each of HCMV mutants is verified by DNA blot hybridization analysis as described previously (Jones et al., 1991).

Antibodies

Rabbit polyclonal antisera reactive with HCMV US11 proteins and HCMV UL80 proteins are described previously (Jones et al., 1991; 1994). Murine monoclonal antibodies W6/32, specific for a conformation-dependent epitope on the heavy chain of human MHC class I proteins, and Ber-T9, specific for the human transferrin receptor, are purchased. Murine monoclonal antibody TP25.99 (D'Urso et al., 1991), specific for a conformation-independent epitope on the heavy chain of human MHC class I proteins, is obtained from Dr. S. Ferrone (Department of Microbiology, New York Medical College, Valhalla, N.Y.). Murine monoclonal antibody 9221, specific for the HCMV IE1 protein, is purchased from Dupont.

Radiolabeling and immunoprecipitation of infected cell proteins

Pulse-chase radiolabeling is done according to standard protocol (Sambrook et al., 1989). HCMV-infected HFF cells (multiplicity of infection equals five) is pulse-labeled with 200 μCi of [$^{35}$S] methionine and [35S] cysteine (NEN-DuPont) per ml in methionine/cysteine-free Dulbecco's modified Eagle medium (DMEM) at the indicated time period postinfection. The radioactive media is removed, the cells washed twice in complete DMEM, and chases are done for the indicated time in complete DMEM. Proteins are extracted using triple detergent lysis buffer (Sambrook et al., 1989). The cleared protein extracts (supernatant after centrifugation for 5 min at 15000×g and 4° C.) are retained for immunoprecipitation according to standard protocol (Sambrook et al., 1989). Proteins binding to antibodies are pelleted using protein A sepharose (Pharmacia). For immunoprecipitations of the human transferrin receptor, rabbit anti-mouse IgG (Pierce) are added prior to protein A sepharose. The washed immunoprecipitates were boiled in the presence of 2-mercaptoethanol and electrophoresed in denaturing polyacrylamide gels. The gels are fixed and soaked in 1M sodium salicylate fluor (Sambrook et al.,1989) prior to drying and autoradiography.

Immunofluorescence. Immunofluorescence assays are done according to standard protocol (Harlow, 1989). All procedures are done in 60mm tissue culture plates. Briefly, infected or uninfected HFF cells were fixed with 4% paraformaldehyde and permeabilized with 0.2% TRITON X-100™ (where indicated). After adding 3% bovine serum albumin in phosphate-buffered saline, the cells are held overnight at 4° C. The cells are treated sequentially with the following antisera, each for 30 min at room temperature: 10% HCMV-negative human serum (to block any Fc receptors); the indicated primary antibody; and FITC-conjugated anti-mouse or anti-rabbit IgG, as appropriate.

EXAMPLE 2

Class I down regulation in HCMV wild-type-infected human fibroblasts. We sought to ascertain the timing and nature of MHC class I heavy chain down regulation in the present invention's human foreskin fibroblast (HFF) cell culture system. By flow cytometry, HCMV strain AD169 wild-type-infected HFF cells are significantly reduced in the expression of class I heavy chains on their cell surface at late times postinfection (i.e. 72 h) using the conformation-dependent class I monoclonal antibody W6/32 (FIG. 1). In western analyses using the conformation-independent class I monoclonal antibody (TP25.99), it is demonstrated that the steady state level of class I protein is also reduced at late times postinfection (FIG. 2A). Because viral peptides are presented at the cell surface by class I complexes assembled after infection, we sought to assess the status of class I proteins synthesized at various times postinfection by immunoprecipitation of metabolically radiolabeled proteins. As shown in FIG. 2B, reduction in expression of class I heavy chains is detected both in the presence and absence of the viral DNA synthesis inhibitor, phosphonoformate. This indicates that viral immediate-early or early gene functions are sufficient for heavy chain reduction. In addition, it is demonstrated that heavy chain down regulation was detected at very early times postinfection: 3 h (FIG. 2C). Since this effect is observed using the conformation-independent antibody, the reduction reflects overall levels of newly synthesized heavy chains.

Screening of HCMV mutants for the loss of MHC class I down regulation

Figure 4A:
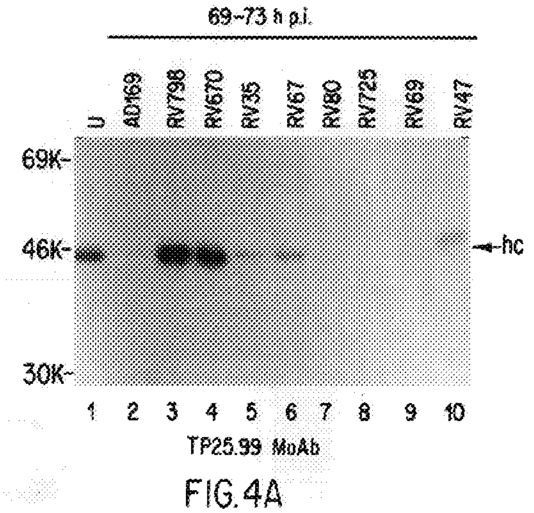
FIGS. 4A–4C show the analysis of heavy chain expression in cells infected with HCMV mutants. HFF cells were uninfected (U) or infected with the indicated virus (multiplicity of infection of 5 PFU/cell) and radiolabeled for 4 h at late times postinfection (69–73 h). Proteins were harvested immediately after radiolabeling.
Figure 4C:
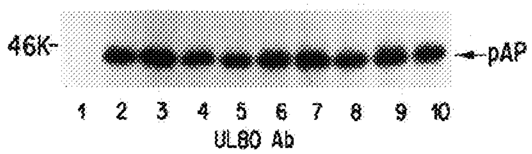
Figure 4B:
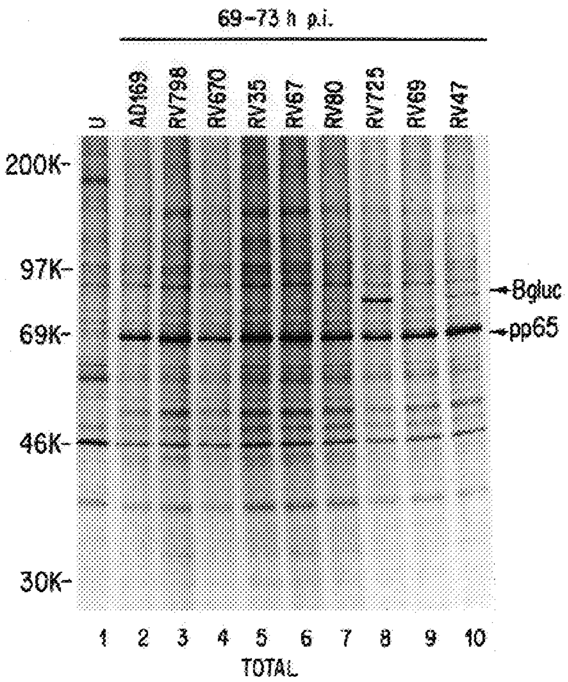

Several previously constructed HCMV deletion mutants, representing 18 nonessential ORFs (UL33, UL81, IRS1, US1–US13, US27–US28, and TRS1), are screened for heavy chain expression by flow cytometry and immunoprecipitation analyses. Only RV670, a mutant deleted of a 9-kb region within the S component of the HCMV genome (Jones and Muzithras, 1992), does not retain the wild-type down regulation phenotype (FIG. 4A). This mutant is deleted of at least 11 ORFs, IRS1 through US11 (except for US10), which includes the US6 family of genes (US6–US11) which putatively encode glycoproteins (Chee et al., 1990). To confirm this observation, two additional independently derived mutants which have the same deletion as RV670 and a new mutant, RV7186, deleted of the entire IRS1–US11 region (FIG. 3) are tested. Each is phenotypically identical to RV670 and stably expressed class I heavy chains. Previously, we constructed HCMV mutants deleted of US6 family ORFs, either individually or in groups (Jones and Muzithras, 1992), and similar deletion mutants within the adjacent IRS1-US3 region. By immunoprecipitation using the conformation-independent antibody, all of these mutants are shown to retain the ability to down regulate class I heavy chains (FIG. 4A) at late times postinfection in HFF cells. Control experiments indicate that radiolabeling is equivalent between the different infected cell cultures (FIG. 4B) and that infection proceeded to late times equally, as judged by pp65 (FIG. 4B) and UL80 protein (FIG. 4C) expression. These data indicate: (i) that more than one viral gene is sufficient for the reduction in class I heavy chains; or (ii) gene(s) between US3 and US6, deleted in RV670 and RV7186 but not the other mutants, is required for the phenotype.

Figure 5A:
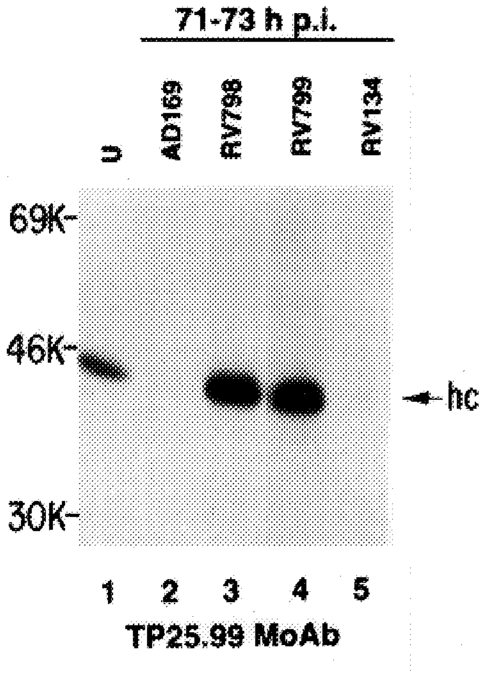
FIG. 5A–5C shows immunoprecipitation of class I heavy chains from RV798-, RV799-, RV134-, or AD169 wild-type-infected cells. HFF cells were uninfected (U) or infected with the indicated virus (multiplicity of infection of 5 PFU/cell) and radiolabeled for 2 h at late times postinfection (71–73 h). Proteins were harvested immediately after radiolabeling.
Figure 5B:
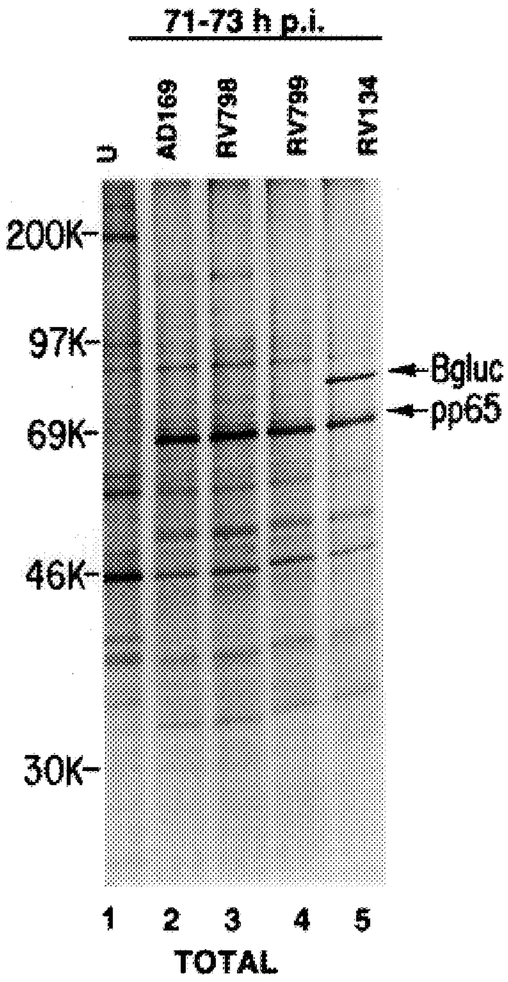
Figure 5C:
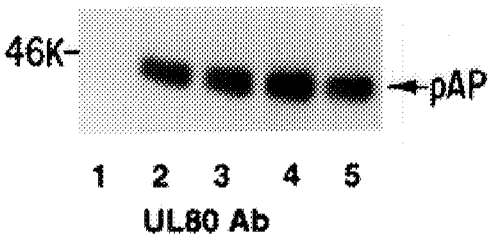

Identification of a 7-kb region of the HCMV genome required for MHC class I down regulation To further localize the region containing gene(s) involved in MHC class I heavy chain down regulation, additional HCMV replacement mutants containing deletions of multiple genes within the IRS1–US11 gene region are created (FIG. 3). One of these mutants, RV798, is deleted of genes from US2–US11. In HFF cells infected by RV798 and analyzed at late times postinfection, MHC class I heavy chains are not down regulated as they are in wild-type strain AD169-infected cells (FIG. 4A); in fact, a slight stimulation is observed. Several independently-derived deletion mutants identical to RV798 were examined similarly: all lacked the ability to down regulate class I heavy chains. To further confirm that the 7-kb HCMV US2–US11 region contains the gene(s) required for heavy chain down regulation, mutant RV799 is constructed which has the identical US2–US11 deletion as RV798, but is created by a different strategy. RV798 is derived from wild-type strain AD169 by inserting a β-glucuronidase marker gene in the place of US2–US11. In contrast, the parent of RV799 is RV134, a mutant which is β-glucuronidase-positive since it has a β-glucuronidase expression cassette inserted within the US9–US10 intergenic region (Jones et al., 1991). To create RV799, a plasmid is designed which upon recombination with the RV134 genome would simultaneously delete US2–US11 and the β-glucuronidase expression cassette (FIG. 3). The proper RV799 HCMV mutant is isolated as a white plaque in the presence of the β-glucuronidase substrate, since it β-glucuronidase-negative. RV799, but not the RV134 parent, is phenotypically identical to RV798 (FIG. 5) Thus, since RV798 and RV799 are created by different strategies using parents which retained the ability to down regulate MHC class I heavy chains, this confirms that the gene(s) required for the phenotype are located within the 7-kb US2–US11 region (bases 193119–200360 Set forth in SEQ. ID NO:3).

Figure 6:
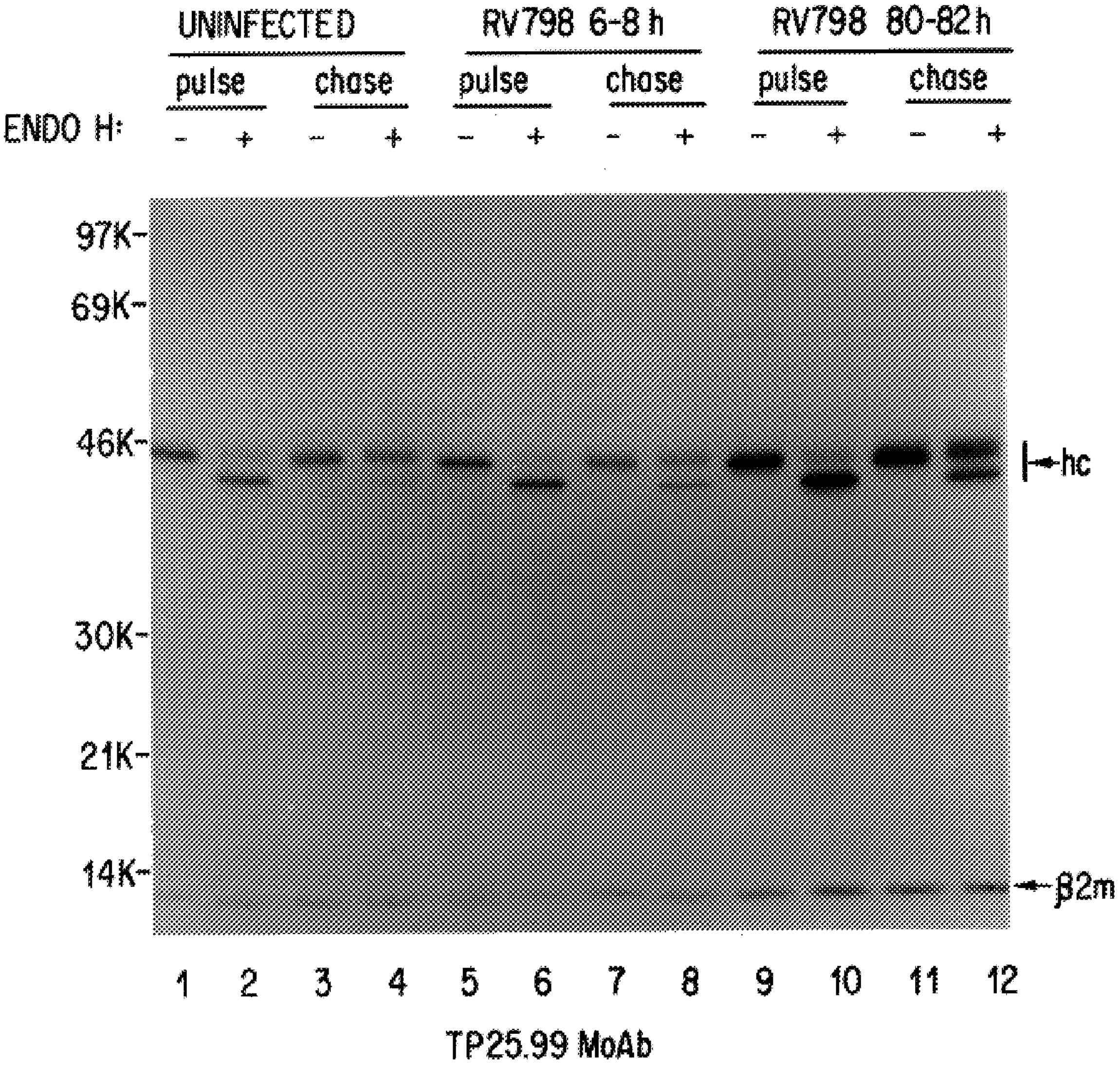
FIG. 6 is a radiograph showing the endoglycosidase H sensitivity of class I heavy chains synthesized in RV798-infected cells. HFF cells were infected with RV798 (multiplicity of infection of 5 PFU/cell) and radiolabeled for 2 h at early times (6–8 h) or late times (80–82 h) postinfection. For comparison purposes, uninfected cells were radiolabeled for 2 h. Proteins were harvested either immediately after radiolabeling (pulse) or after a 2 h chase (chase) in complete unlabeled media. Class I heavy chains were immunoprecipitated using TP25.99 murine monoclonal antibody. Immunoprecipitated protein were incubated for 6 h either in the presence (+) or absence (−) of 1.5 mU of endoglycosidase H, prior to SDS-polyacrylamide gel electrophoresis and fluorography.

To determine whether the proper surface expression of class I heavy chains occurred at late times postinfection with either RV798 or RV799, immunofluorescence assays are done. Using either the conformation-dependent (W6/32) or conformation-independent (TP25.99) monoclonal antibodies, surface expression of MHC class I heavy chains is detected in uninfected and RV798- and RV799-infected HFF cells, but not wild-type AD169-infected HFF cells. Proper maturation of class I heavy chains in uninfected cells yields endoglycosidase H resistant molecules. In contrast, class I heavy chains synthesized in AD169-infected cells are reported to be entirely endoglycosidase H sensitive (Beersma et al., 1993). As shown in FIG. 6, class I heavy chains synthesized in RV798-infected HFF cells, either at early or late times postinfection, are converted to the mature endoglycosidase H-resistant form at a rate similar to those synthesized in uninfected cells. Taken together, these data indicate that MHC class I synthesis, processing, and surface expression are not impaired in cells infected with these HCMV mutants. Furthermore, the results indicate that the 7-kb region containing US2–US11 genes contain one or more genes required for heavy chain down regulation by HCMV.

Figure 7A:
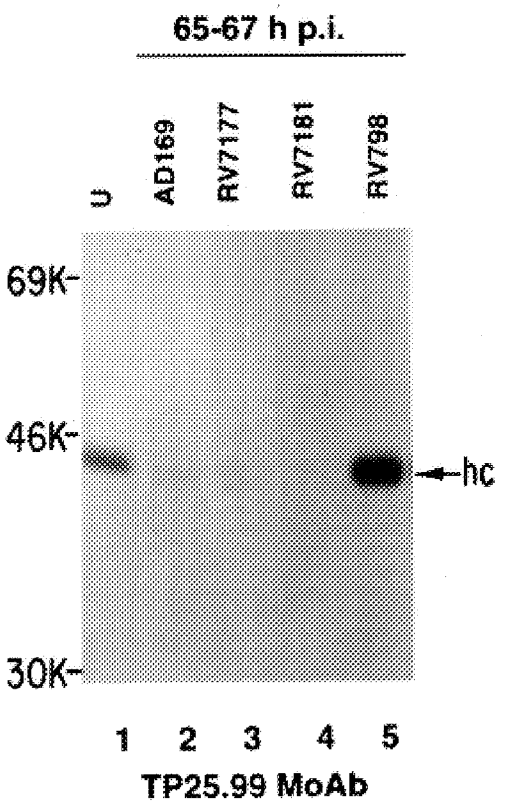
FIGS. 7A–7C show the immunoprecipitation of class I heavy chains from RV798-, RV7181-, RV7177-, or AD169 wild-type-infected cells. HFF cells were uninfected (U) or infected with the indicated virus (multiplicity of infection of 5 PFU/cell) and radiolabeled for 2 h at late times postinfection (65–67 h). Proteins were harvested immediately after radiolabeling.
Figure 7C:
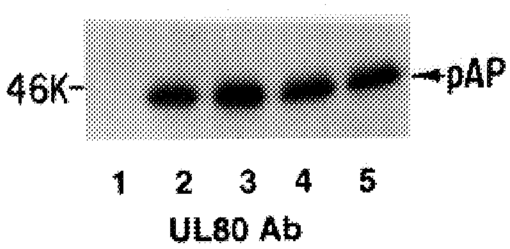
Figure 7B:
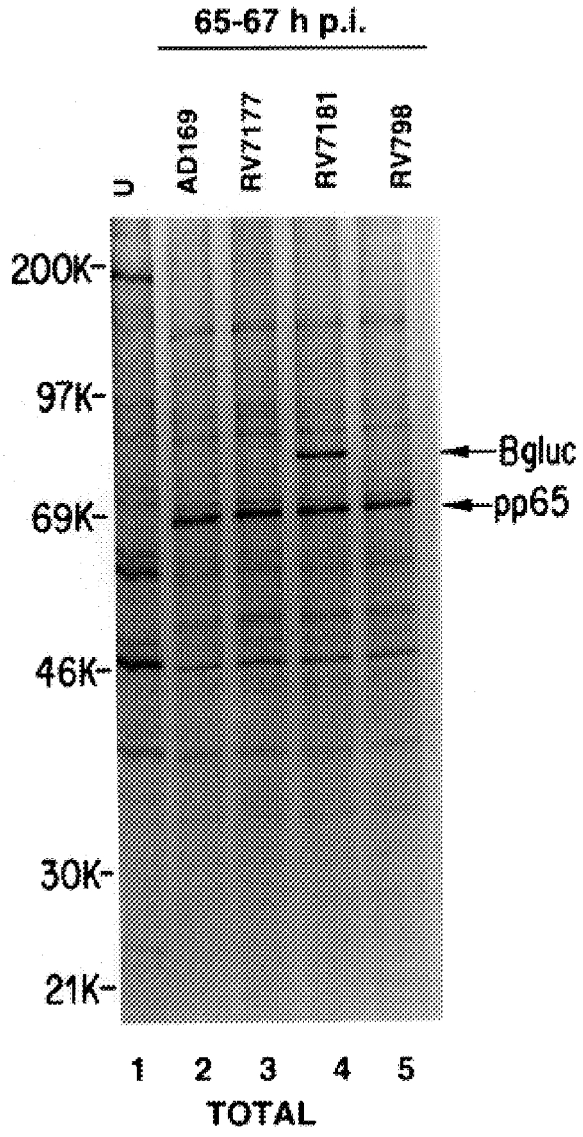
Figure 8A:
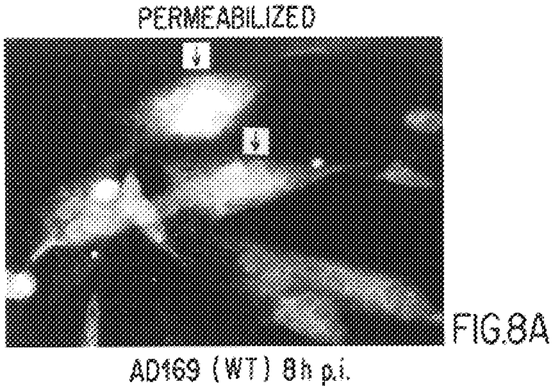
FIGS. 8A–8D are photographs which show localization of US11 gene product (gpUS11) in infected cells by immunofluorescence. HFF cells were uninfected or infected with either AD169 wild-type or RV699 (deleted of the US11 gene) at a multiplicity of infection of 5 PFU/cell. After 8 h, uninfected and infected cells were fixed with 4% paraformaldehyde. Some cells were then permeabilized with 0.2% TRITON X-100™(alkylanyl polyether alcohol). The primary antibody was rabbit polyclonal antisera raised against a US11 fusion protein (Jones and Muzithras, 1991). Fluorescence was visualized through a Zeiss microscope.
Figure 8B:
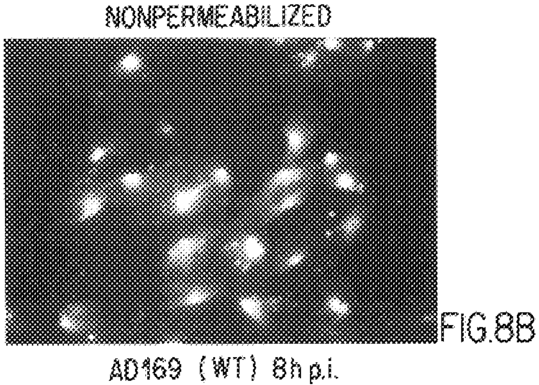
Figure 8C:
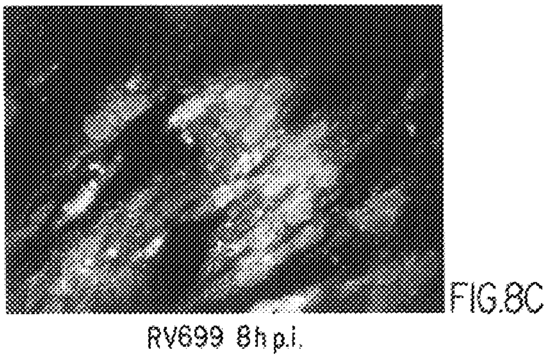
Figure 8D:
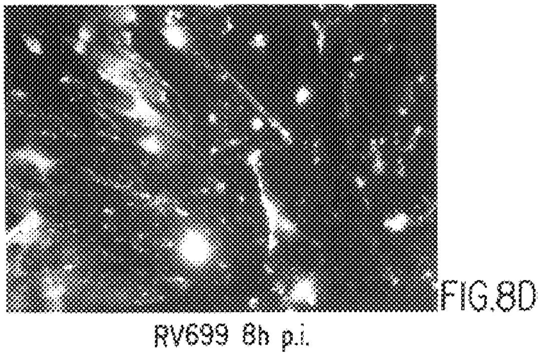

Two subregions within the US2–US11 gene region contain genes which are involved in class I heavy chain down regulation The region of the HCMV genome deleted in RV35 is from US6–US11, and US2–US11 in RV798 (FIG. 3). In RV35-infected HFF cells, MHC class I heavy chains are down regulated, but in RV798-infected cells they are not (FIG. 4A). This data indicates that one or more genes involved in heavy chain down regulation maps within the 2-kb subregion from ORF US2 through US5 (subregion A; bases 193119–195607 Set forth n SEQ. ID NO:7). To determine if this 2-kb subregion is required for class I heavy chain down regulation, HCMV replacement mutants RV7181 and RV7177 are examined. HCMV ORFs IRS1–US9 and IRS1–US6 are deleted, respectively, in these mutants; hence, subregion A is absent from both mutants. Experiments in infected HFF cells at late times postinfection indicates that both mutants retained the ability to efficiently down regulate class I heavy gene expression (FIG. 7). Therefore, when present in the HCMV genome, gene(s) within subregion A are sufficient for reduction of MHC expression (e.g. RV35), although their presence is not required for the phenotype. Furthermore, the cumulative data indicate that there are no HCMV genes within the identified 7-kb US2–US11 region (i.e. the region deleted in RV798) which are absolutely required for efficient heavy chain down regulation in infected HFF cells, suggesting that gene(s) from another portion of the US2–US11 gene region are also sufficient for the phenotype at late times postinfection.

Evidence indicating that the US11 gene product is involved in MHC class I heavy chain down regulation In HFF cells infected with mutant RV7181, deleted from IRS1–US9 (FIG. 3), MHC class I heavy chain expression is down regulated, in contrast to RV798-infected HFF cells (FIG. 7). This data suggests that a second subregion (subregion B), comprised of the US10 and US11 genes (bases 199083–200360 Set forth in SEQ. ID NO:2), is involved in reduction of heavy chain expression. However, the expression of US10 from the context of the HCMV genome is not sufficient for heavy chain down regulation. HCMV mutant RV670 expresses US10 at steady-state levels similar to wild-type and is deleted of all of the other ORFs in the 7-kb US2–US11 gene region, but it does not cause down regulation of MHC class I heavy chains in infected HFF cells (FIGS. 2B and 4A).

US11 encodes a 32-kDa glycoprotein (gpUS11) containing N-linked, but not O-linked, carbohydrates which are completely sensitive to endoglycosidase H, indicating that the sugars are in the high mannose form. gpUS11 is detected throughout infection, beginning at very early times (i.e. 3 h) and continuing through late times postinfection. However, levels of gpUS11 in the infected cell are most abundant at approximately 8 h postinfection. To determine its location in the infected cell, rabbit polyclonal antisera (Jones and Muzithras, 1991) is used in immunofluorescence assays of wild-type strain AD169-infected cells. Uninfected and RV699-infected HFF cells are used as negative controls. RV699 is an HCMV mutant which is isogeneic with AD169, except for a deletion of the US11 ORF (Jones et al., 1991). In cells fixed and permeabilized at 8 h postinfection, cytoplasmic fluorescence which obscured definition of the nucleus is observed in AD169-infected HFF cells, but not in either negative control cells (FIG. 8). In general, the specific fluorescence is more intense in the perinuclear area. There is no specific fluorescence detected in non-permeabilized cells (FIG. 8). The fluorescence and endoglycosidase-H sensitivity data indicate that gpUS11 is not a cell surface glycoprotein. From the translated DNA sequence, gpUS11 is predicted to have hydrophobic domain near its N- and C-termini (Weston and Barrell, 1986) which are putative signal sequence and transmembrane domain, respectively. Thus, gpUS11 is associated with intracytoplasmic membranes, possibly the endoplasmic reticulum.

Figure 9A:
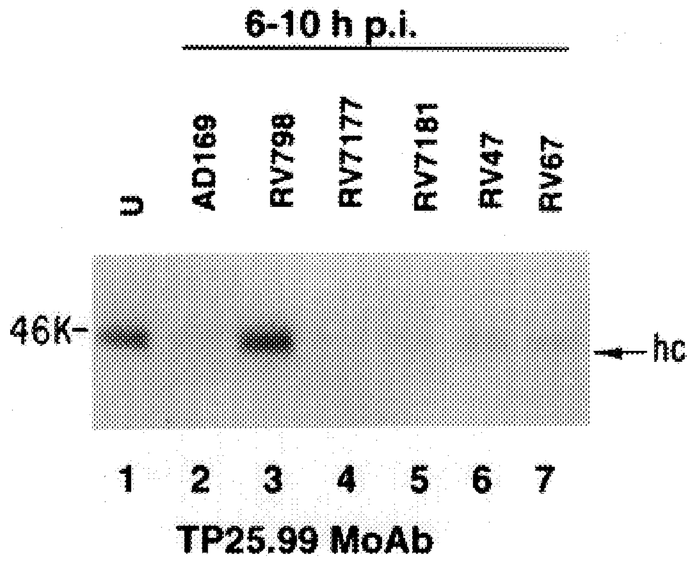
FIGS. 9A–9D show analysis of heavy chain expression in cells infected with HCMV mutants at early times postinfection. HFF cells were uninfected (U) or infected with the indicated virus (multiplicity of infection of 5 PFU/cell) and radiolabeled for 4 h from 6–10 h postinfection. Proteins were harvested immediately after radiolabeling.
Figure 9B:
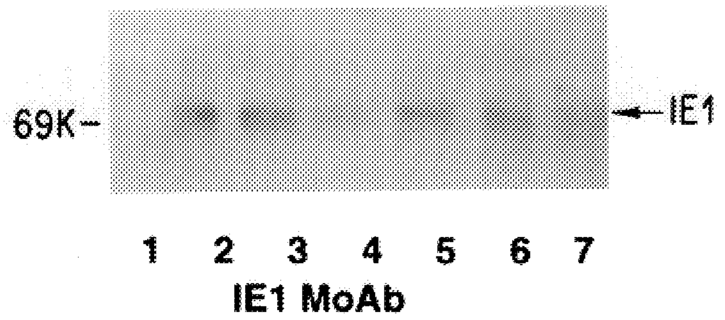
Figure 9C:
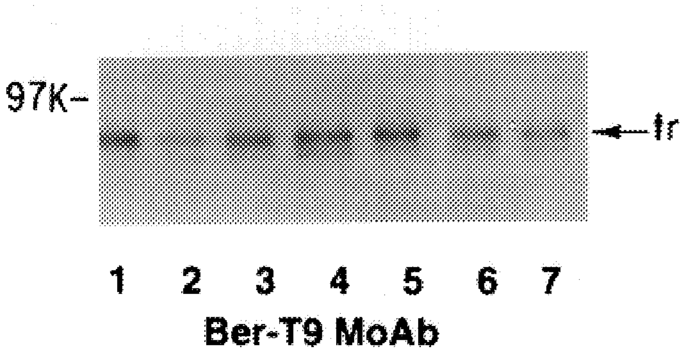
Figure 9D:
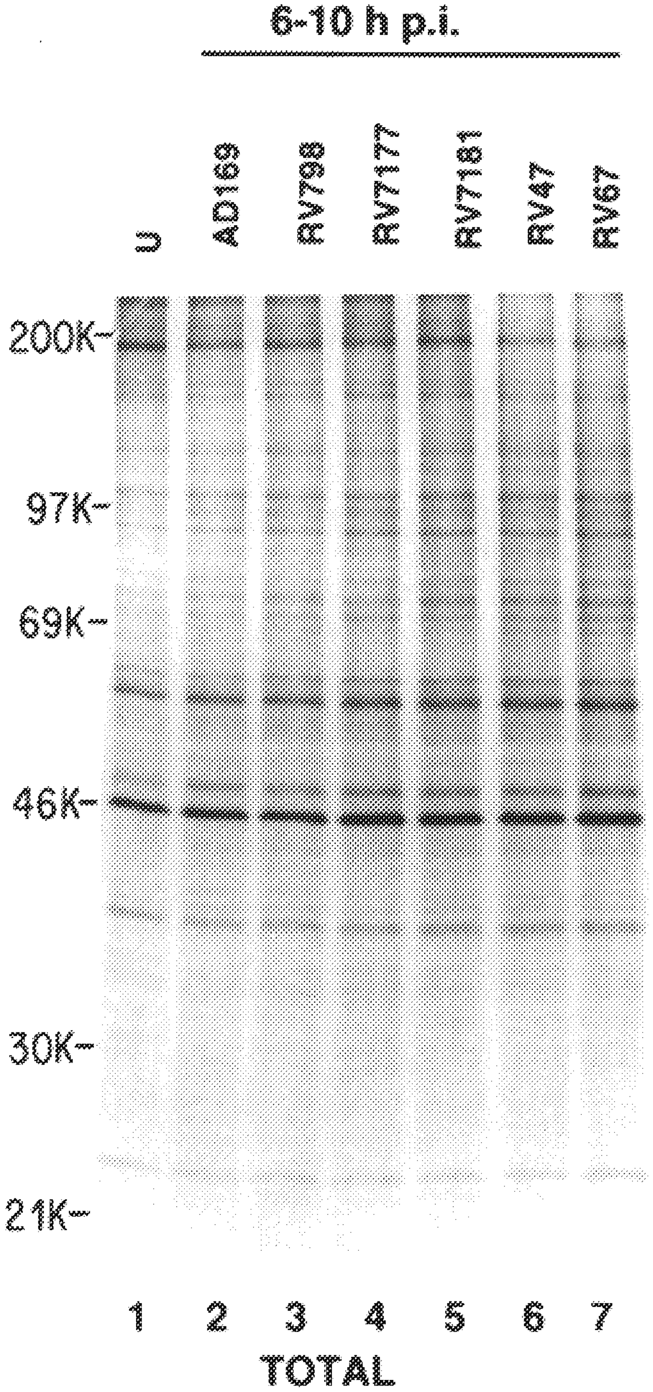

Down regulation of MHC class I expression at early times postinfection by HCMV mutants MHC class I expression in wild-type strain AD169-infected cells are shown to begin at very early times postinfection (FIG. 2C). To determine if any of the mutants are deficient for this early down regulation, immunoprecipitation experiments are performed using extracts from infected HFF cells radiolabeled from 6–10 h postinfection. The level of class I heavy chains are reduced during this early period postinfection in HFF cells with each of the mutants, except for RV798, the mutant deleted of the entire 7-kb US2–US11 region (FIG. 9A). Control experiments demonstrated that the different mutant-infected cells are equally infected and radiolabeled (FIG. 9B and D). Expression of another cellular glycoprotein, the transferrin receptor, is not differentially affected by the various mutants (FIG. 9C). Thus, genes required for heavy chain down regulation at early times postinfection are the same as those necessary for reduction at late times postinfection. Moreover, expression of gene(s) from either subregion identified to be involved in down regulation of heavy chain expression at late times postinfection are sufficient for reduction at very early times postinfection.

EXAMPLE 3

Recombinant HCMV (RV798) Vaccine Preparation

HCMV vaccines are prepared in using a method described previously (Elek and Stern, 1974). HCMV mutant RV798 is grown on MRC-5 human diploid lung fibroblasts (CCL171 [American Type Culture Collection]) or human foreskin fibroblasts (MRHF [BioWhittaker]). Cells are infected at a multiplicity of infection equal to one in Dulbecco's modified Eagle medium (DMEM) containing 5% calf serum and 5% fetal calf serum. After 24 h, the medium is removed and the cells washed three times with either Hank's balanced salt solution or Dulbecco's phosphate-buffered saline. Fresh DMEM medium without serum is added; the infected cells are incubated 4 days after the appearance of late viral cytopathic effect (usually 7 days postinfection). After a preclearing centrifugation step (6,000×gravity for 20 min at 18° C.), cell-free virus is pelleted by centrifugation at 15,500×gravity for 1 h at 18° C. The pelleted virus is resuspended in Dulbecco's phosphate-buffered saline containing 25% sorbitol and stored in aliquots at −70° C. The titer of RV798 vaccine stock is determined using standard procedures on human foreskin fibroblasts (Wentwork and French, 1970). The vaccine is administered by subcutaneous inoculation of approximately $10^3$–$10^7$ plaque forming units into the deltoid region of the upper arm, as described previously (Elek and Stern, 1974; Gehrz et al., 1980; Starr et al., 1981).

EXAMPLE 4 gpUS11 is sufficient for down regulation of MHC class I heavy chains

To determine if the US11 gene product, in the absence of any other viral gene products, is capable of causing heavy chain down regulation, the US11 coding region (bases 199716 to 200360 Set forth in SEQ. ID NO:19 [Chee et al., 1990]) and some non-coding flanking sequences, encompassing bases 199683 to 200391 Set forth in SEQ. ID NO:20, are cloned into a eukaryotic expression plasmid under the transcriptional control of the constitutive HCMV major immediate-early promoter-enhancer. Human U373-MG astrocytoma cells (HTB 17 [American Type Culture Collection]) are transfected with this plasmid (Sambrook et al, 1989) and stably transformed cells are selected in the presence of 0.375 μg/ml of puromycin, since the plasmid also encodes for the prokaryotic puromycin resistance gene. Clones are picked and expanded into cell lines. Those expressing gpUS11 are identified by western blot analysis; different cell lines expressed varying amounts of US11. MHC class I heavy chain expression in these cell lines is analyzed in a similar fashion. As shown in FIG. 11, expression of US11 is inversely correlated with the expression of class I heavy chains. These data prove that expression of HCMV US11 is sufficient for the down regulation of MHC class I heavy chain expression, in the absence of any other viral gene products.

REFERENCES

Alford, C. A., and W. J. Britt. 1990. Cytomegalovirus, p. 1981–2010. In D. M. Knipe and B. N. Fields (ed.), Virology, 2nd ed. Raven press, New York.

Anderson, M., S. Paabo, T. Nilsson, and P. A. Peterson. 1985. Impaired intracellular transport of class I MHC antigens as a possible means for adenoviruses to evade immune surveillance. Cell 43:215–222.

Beck, S., and B. G. Barrell. 1988. Human cytomegalovirus encodes a glycoprotein homologous to MHC class I antigens. Nature 331:269–272.

Beersma, M. F. C., M. J. E. Bijlmakers, and H. L. Ploegh. 1993. Human cytomegalovirus down regulates HLA class I expression by reducing the stability of class I H chains. J. Immunol. 151:4455–4464.

Browne, H., M. Churcher, and T. Minson. 1992. Construction and characterization of a human cytomegalovirus mutant with the UL18 (class I homolog) gene deleted. J. Virol. 66:6784–6787.

Browne, H., G. Smith, S. Beck, and T. Minson. 1990. A complex between the MHC class I homolog encoded by human cytomegalovirus and β2 microglobulin. Nature 347:770–772.

Burgert, H. G., and S. Kvist. 1985. An adenovirus type 2 glycoprotein blocks cell surface expression of human histocompatibility class I antigens. Cell 41:987–997.

Campbell, A. E., J. S. Slater. 1994. Down-regulation of major histocompatibility complex class I synthesis by murine cytomegalovirus early gene expression. J. Virol. 68:1805–1811.

Campbell, A. E., J. S. Slater, V. J. Cavanaugh, and R. M. Stenberg. 1992. An early event in murine cytomegalovirus replication inhibits presentation of cellular antigens to cytotoxic T lymphocytes. J. Virol. 66:3011–3017.

Chee, M. S., A. T. Bankier, S. Beck, R. Bohni, C. M. Brown, R. Cerny, T. Horsnell, C. A. Hutchinson, T. Kouzarides, J. A. Martignetti, E. Preddie, S. C. Satchwell, P. Tomlinson, K. Weston, and B. G. Barrell. 1990. Analysis of the protein-coding content of the sequence of human cytomegalovirus strain AD169. Curr. Top. Microbiol. Immunol. 154:125–169.

Colberg-Poley, A. M., L. D. Santomenna, P. P. Harlow, P. A. Benfield, and D. J. Tenney. 1992. Human cytomegalovirus US3 and UL36–38 immediate-early proteins regulate gene expression. J. Virol. 66:95–105.

del Val, M., K. Munch, M. Reddehasse, and U. Koszinowski. 1989. Presentation of CMV immediate-early antigen to cytotoxic T lymphocytes is selectively prevented by viral genes expressed in the early phase. Cell 58:305–315.

D'Urso, C. M., Z. Wang, Y. Cao, R. Tatake, R. A. Zeff, and S, Ferrone. 1991. Lack of HLA class I antigen expression by cultured melanoma cells FO-1 due to a defect in β2m gene expression. J. Clin. Invest. 87:284–292.

Elek, S. D., and H. Stern. 1974. Development of a vaccine against mental retardation caused by cytomegalovirus infection in utero. Lancet 1:1–5.

Gehrz, R. C., W. R. Christianson, K. M. Linner, K. E. Groth, and H. H. Balfour, Jr. 1980. Cytomegalovirus vaccine: specific humoral and cellular responses in human volunteers. Arch. intern. Med. 140:936–939.

Gilbert, M. J., S. R. Riddell, C-R. Li, and P. D. Greenberg. 1993. Selective interference with class I major histocompatibility complex presentation of the major immediate-early protein following infection with human cytomegalovirus. J. Virol. 67:3461–3469.

Gooding, L. R. 1992. Virus proteins that counteract host immune defenses. Cell 71:5–7.

Gretch, D. R., and M. F. Stinski. 1990. Transcription of the human cytomegalovirus glycoprotein gene family in the short unique component of the viral genome. Virology 174:522–532.

Jones, T. R., and Muzithras, V. P. 1991. Fine mapping of transcripts expressed from the US6 gene family of human cytomegalovirus strain AD169. J. Virol. 65:2024–2036.

Jones, T. R., and V. P. Muzithras. 1992. A cluster of dispensable genes within the human cytomegalovirus genome short component: IRS1, US1 through US5, and the US6 family. J. Virol. 66:2541–2546.

Jones, T. R., V. P. Muzithras, and Y. Gluzman. 1991. Replacement mutagenesis of the human cytomegalovirus genome: US10 and US11 gene products are nonessential. J. Virol. 65:5860–5872.

Jones, T. R., L. Sun, G. A. Bebernitz, V. P. Muzithras, H-J. Kim, S. H. Johnston, and E. Z. Baum. 1994. Proteolytic activity of human cytomegalovirus UL80 protease cleavage site mutants. J. Virol. 68: 3742–3752.

Jonjic, S., M. de Val, G. M. Keil, M. J. Reddehasse, and U. Koszinowski. 1988. A nonstructural viral protein expressed by a recombinant vaccinia virus protects against lethal cytomegalovirus infection. J. Virol. 62:1653–1658.

Mavromara-Nazos, P., M. Ackerman, and B. Roizman. 1986. Construction and properties of a viable herpes simplex virus 1 lacking coding sequences of the alpha 47 gene. J. Virol 60:807–812.

McKnight, S. L. 1980. The nucleotide sequence and transcript map of the herpes simplex virus thymidine kinase gene. Nucl. Acids Res. 8:5949–5964.

Oram, J. D., R. G. Downing, A. Akrigg, A. A. Dollery, C. J. Duggleby, G. W. G. Wilkinson, and P. J. Greenaway. 1982. Use of recombinant plasmids to investigate the structure of the human cytomegalovirus genome. J. Gen. Virol. 59:111–129.

Sambrook, J., E. F. Fritsch, and T. Maniatis. 1989. Molecular cloning: a laboratory manual, 2nd ed. Cold Spring Harbor Laboratory Press, Cold Spring Harbor, N.Y.

Schwartz, R. H. 1985. T lymphocyte recognition of antigen in association with gene products of the major histocompatibility complex. Ann. Rev. Immunol. 3:237–261.

Starr, S. E., J. P. Glazer, H. M. Friedman, J. D. Farquhar, and S. A. Plotkin. 1981. Specific cellular and humoral immunity after immunization with live Towne strain cytomegalovirus vaccine. J. Infect. Dis. 143:585–589.

Tenney, D. J., and A. M. Colberg-Poley. 1991. Human cytomegalovirus UL36–38 and US3 immediate-early genes: temporally regulated expression of nuclear, cytoplasmic, and polysome-associated transcripts during infection. J. Virol. 65:6724–6734.

Tenney, D. J., L. D. Santomenna, K. B. Goudie, and A. M. Colberg-Poley. 1993. The human cytomegalovirus US3 immediate-early protein lacking the putative transmembrane domain regulates gene expression. Nucl. Acids Res. 21:2931–2937.

Wentworth, B. B., and French, L. 1979. Plaque assay of cytomegalovirus strains of human origin. Proc. Soc. Exp. Biol., Med. 135:253–258.

Weston, K. 1988. An enhancer element in the short unique region of human cytomegalovirus regulates the production of a group of abundant immediate early transcripts. Virology 162:406–416.

Weston, K., and B. G. Barrell. 1986. Sequence of the short unique region, short repeats, and parts of the long repeats of human cytomegalovirus. J. Mol. Biol. 192:177–208.

Yamashita, Y., K. Shimokata, S. Mizuno, H. Yamaguchi, and Y. Nishiyama. 1993. Down-regulation of the surface expression of class I MHC antigens by human cytomegalovirus. Virology 193:727–736.

York, I. A., C. Roop, D. W. Andrews, S. R. Riddell, F. L. Graham, and D. C. Johnson. 1994. A cytosolic herpes simplex virus protein inhibits antigen presentation to CD8+ T lymphocytes. Cell 77:525–535.

Zinkernagel, R. M., and P. C. Doherty. 1980. MHC restricted cytotoxic T cells: studies on the biological role of polymorphic major transplantation antigens determining T cell restriction specificity. Adv. Immunol. 27:51–177.

What is claimed is:

1. A recombinant human cytomegalovirus comprising a genome from which the gene sequence encoding open reading frames IRS-1 to US11 has been deleted.

2. A recombinant human cytomegalovirus comprising a genome having a deletion of the gene sequence encoding open reading frames US2 to US11.

3. A recombinant human cytomegalovirus comprising a genome having a deletion of the gene sequences encoding open reading frames US2 to US5 and US10 to US11.

4. A recombinant human cytomegalovirus comprising a genome having a deletion of the gene sequences encoding open reading frames US2 to US5 and US11.

* * * * *

UNITED STATES PATENT AND TRADEMARK OFFICE

CERTIFICATE OF CORRECTION

PATENT NO. : 5,846,806
DATED : December 8, 1998
INVENTOR(S) : Jones et al.

It is certified that error appears in the above-identified patent and that said Letters Patent is hereby corrected as shown below:

Column 1,
Line 4, after the title, insert

-- STATEMENT AS TO RIGHTS TO INVENTIONS MADE UNDER FEDERALLY SPONSORED RESEARCH AND DEVELOPMENT

The present invention was made with Government support under Grant No. CA41451 awarded by the National Institutes of Health. The Government has certain rights in the invention. --.

Signed and Sealed this

Twenty-ninth Day of July, 2003

JAMES E. ROGAN
*Director of the United States Patent and Trademark Office*

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 2489 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GCACACGAAA AACCGCATCC ACATCATAGA CAAGTTACAG TCCACAGTCA CATACACGAT     60
AAACAATACC AACAGGGTAA TGTTTATGGA GTAAAACACT ATTGTCCAGG CCACATGCGT    120
GTATGACTTC CGCACCATCC CGTACTGCAT GTTCCACATG TACGCGCTAG ACGTGTAATC    180
CACTCGCAGT TCGGGGACGC AACGCAGCCA GATCACATCC CCTTGCAGTA CCAGACGCAG    240
GGCTAGCGTC TCGAAGATCG GCATCACATC TAAGTTCCGC ACGTTCCACT TTAACGACTC    300
CCCGGGAACG AACTCCACGT CGTCGGCGTG TACGTACAGG TTCTCTCCCA CGCCGCCATA    360
ATCGGCCTTC GGATCGAAGA CGAACCGACT CATGTTGCCC ACGATGCTCC CCCGAGCAAA    420
CAACTTGCCG TTGTCAATGT AGCACCGGTT GTCCTCGATT TGAAACCAGG GATGCTTGGC    480
CGTGGACTTC CAGGGCCGGA GCGCGTCTTC CCCGGCTTTA GTGATTCCAT CGGGCAGGCG    540
GATCAAGGGA CCCATGGAGG TCCAAAGACC CACCCAGGCT TTCCAGAGAT TGTTCATGGT    600
GAAACAGCGT GTGGACTGTA CGCTCTTTCC CAATTTATAT CCCAGAGTAG TGACGTGAGC    660
CCAGCCACCT CCCAGATTCC TGACGTTTTG GTTGTCTTTC CTGCCAATTC CTCCCGTAAA    720
CTTATGATTA TCCTAGCCCA TTCCCGATAA AAATACACGG AGACAGTAGA TAGAGTTACG    780
AATAAACCGG TTTATTTATT CAAGTGTCTC AGGAGATTAT TGAACGAGCG TGGATACCAC    840
GCCGTCGTCA GTTCATGGTG GCATTGAGCA GCCATAGCAC CAGAGTCCCG GCGCCCGGTA    900
TCAGACACGC TGACCTACCG GGCGCCTTCG AGTCCGTACC CCGCGGCCTG GGTGTTAGAG    960
TCCGTACCTT GCAGCCCAGG TAGGTTTCAG GTACCAGCTG GTTCGTACCT GTTAAATAAA   1020
TCGCAGACGG GCGCTCACCC CTACGGTCAG GAGCACAAGA ACAACCAGAG AGAACAGATA   1080
```

TACGAGCAGG GTTCTGAACA GCAGACCCCA ATTGTCGTCT CTCATGCTTC GCTGAAGGTA 1140
CCAGTTGATG GTCTGAGAGC TATAGTCCAT CCTCACCTGA GGAACACACG CGGCATATTT 1200
CTTGGGGTCT CCCCACCTCG TAGACAACGT GATGTCCACC ATATCCACGG TGTGCGTCAC 1260
CGGGTGCCCA CCGATGTTCC ACTCGAAATA GGCTCCGCGC TCATCATGGT GGTACTGCTC 1320
ACCGGACACC TGCAGTCTGT CCATGTAAGA TTGAGAGACG ATACCCACGT TCACAAAGTG 1380
TTTCTCGGTG AAGTTGCCCG ACATCCTCCC CTTGAAGTAC AGCATGCCCA TATGGAACCA 1440
GCATTGGTTC TCCTCCACTC GAAAGTGGGC CGATCTGATC TCCGATACCA CCACATCCAG 1500
GGGCCGGGGC ACCGAGTCCG CGAGTCTCAG GAACAAGACG GCCAGGATCG CGAGCACCAA 1560
CACCGGCTTC ATGGCTCCGA AGGTCCGCTG CTCGGCTCCG CTCACCGCTC CGGTCTGGCT 1620
GCAGCAGTGC TTCGCTGAGA AGTAGCGTGT GGACTGAACG GTGTTTTTGA ATATATAGCG 1680
TTTCTTGGTG ACGTTGTTTC CCCTACGTAG TAGGCAACTA CGTGCCAAAA GAGGCGTTAC 1740
GGTACTTTCC GTACTGGGAT TTCCAAACCG GGACTTTCCA CACGGCGGTT TCAACACCGG 1800
GACTTTTCAC ACGGTGATTT CGGCACCGGG ACTTTCCGCA CGGCGGTTTC GCCACCGCTG 1860
ACGTTCTCAT CGCCGCCCAC GTCAACGGTG GCGACACCGT ACTTTCCCAT GCGGTTTATA 1920
AACGTCAAGA GTCACGTCAG TCGCCCACCC CCATTACACG GCGATATCCC GATAGGGCAT 1980
GAGGGGACCC GGGTGTCGCG ACATGTCGAC GACAGGTGCG GATTAGTGGT CGTGTCGCGA 2040
CATGGACGTG CAGGGGGATG TCTGTCGCGA TAGAGTTGAT GTGACAGCCC GCTACACCTC 2100
TCTGTCGCGA CATGCATACA CAACGGGCCG GCTTGTCGGC GATTGTCGCG ACATATCGTT 2160
ATCAGTTAGC GACCGGAGTT GTCTATCGCG ACATATCGTC GACTATCGCG ACAGAAAAAA 2220
TACCGTTCGT AGAGAATGCC GTGTTGAAGG AACGCGCTTT TATTGAGACG ATAAAACAGC 2280
ATCAGGAGCC ACAACGTCGA ATCCCACGTC CAGTCGATTC GTATGTTATG CTGCACAGCA 2340
ATGCTAGAAT AACAACCAGC AGGGTAATCC CGCAACATAA ATACAAAGTC ACAGCGAAGA 2400
ATCCGTGTCG TTCTATCAAG CGAAACGCGT TCCAAACGGC CCCGTCACAG ACGCAGTTAT 2460
TCATAAGCGT TAACAACCGG TGGCTAGGA 2489

( 2 ) INFORMATION FOR SEQ ID NO:2:

( i ) SEQUENCE CHARACTERISTICS:
( A ) LENGTH: 1278 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TTCGCGAGGT GGATAATAAC CGCATATCAG GAGGAGGGAT CGGGTGATGA CGCAGGCCCC 60
GCAGAACAGT CCGAAATAAA TTTTTAGTAT TGCCCCATAG TCGCCTAGAT ACCAGAGGTA 120
CGTTAAGTTC ATCAAAACGC CCATCGGCGT CCCGGAATCG TATACCGGGC ACACGAAGCG 180
TTCATAACAA TCCCGGGAGG CGAGTGTTAG GGTAGCAGAG TAGTTTCGGG GTCGGTTTCC 240
TTCCGGCGAC GACAGTTCCG TGGGCAGCAG AATGTACAGC GCCTCGGTAG CTGTCGCGGT 300
GCCTTCCACG AGGATGGGCT GCCGGTGCCT TTCGTGATTT TCCCCGTCGT GTAGCCAAGC 360
CGAGGCCCGC AAAGTCTTAG GCGAGGGGAA TTGTCCATAG AGTTTCACCG CACCCTTCAG 420
TACATGGTTC TGAATAACAC AGCCGCACGT GAAGTAGGTA GGTTCTCTCG TCTCCTCCGT 480
GGCTGCCGCC ACCACTCCCA GCCACCACAA CAGGCAGATC GCCAGAGGGT TCCGGAGGCT 540

-continued

TCCCCGGCGT AGCATGGTTT TGGGTTAAAG CAAAAAGTCT GGTGAGTCGT TTCCGAGCGA 600

CTCGAGATGC ACTCCGCTTC AGTCTATATA TCACCACTGG TCCGAAAACA TCCAGGGAAA 660

ATGTCGGTGC AGCCAACCTT TCACATACAG CCCCCAAAAC ACTTGAATCA CTGCCACCAT 720

CATCAGCGTA TACTGCGCCG ACTTAATCGT GAGCGCGTAG TACGCCATTA GACGGCGATC 780

TTCGAACAAT AGTCGTTCGA TGTCCTCTAA CGAGCTCCAC AGGGGAACCC AAGGCACGAG 840

GCACCGGGGT TCGCACTCTA CATAATAAGT TTGGCATTGG TGGCAGGGGG AAAAGTAGAA 900

CAACACGAGT TTTGTGCGTT GGGGAACACG ATAGTCCCGG AGCCAGTAGC GTTTTGCGAC 960

GAGGCTTTCG GAGACGTCCT CCACCGGCGT CGGCACTCGA TCCGCGTAGC CCTCCAGCGT 1020

CTGGTAGTAC ACCCGGGGTG TCGGCGTGGG CACGGACAGG TTCCCGCGCA GGGTCCACAG 1080

AGCCTCCAGT CGACCGCCCG ATCGGAGCAC GCAGCGCGCC TCGGAATACT CTACTCGGTA 1140

CTCCGAAACA TCGGACAGAG GCGGTAACGG CTCCGTCTCC ACCAAGGGCG GAGGTTCATC 1200

GAAAAGAGTC AAGGATAATT CAGGCATACT ACCCGCGACC GGGGCCCAGA GGGCTAGAAT 1260

AAGCATTACA AGGTTCAT 1278

( 2 ) INFORMATION FOR SEQ ID NO:3:

( i ) SEQUENCE CHARACTERISTICS:
( A ) LENGTH: 7242 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GCACACGAAA AACCGCATCC ACATCATAGA CAAGTTACAG TCCACAGTCA CATACACGAT 60

AAACAATACC AACAGGGTAA TGTTTATGGA GTAAAACACT ATTGTCCAGG CCACATGCGT 120

GTATGACTTC CGCACCATCC CGTACTGCAT GTTCCACATG TACGCGCTAG ACGTGTAATC 180

CACTCGCAGT TCGGGGACGC AACGCAGCCA GATCACATCC CCTTGCAGTA CCAGACGCAG 240

GGCTAGCGTC TCGAAGATCG GCATCACATC TAAGTTCCGC ACGTTCCACT TTAACGACTC 300

CCCGGGAACG AACTCCACGT CGTCGGCGTG TACGTACAGG TTCTCTCCCA CGCCGCCATA 360

ATCGGCCTTC GGATCGAAGA CGAACCGACT CATGTTGCCC ACGATGCTCC CCCGAGCAAA 420

CAACTTGCCG TTGTCAATGT AGCACCGGTT GTCCTCGATT TGAAACCAGG GATGCTTGGC 480

CGTGGACTTC CAGGGCCGGA GCGCGTCTTC CCCGGCTTTA GTGATTCCAT CGGGCAGGCG 540

GATCAAGGGA CCCATGGAGG TCCAAAGACC CACCCAGGCT TTCCAGAGAT TGTTCATGGT 600

GAAACAGCGT GTGGACTGTA CGCTCTTTCC CAATTTATAT CCCAGAGTAG TGACGTGAGC 660

CCAGCCACCT CCCAGATTCC TGACGTTTTG GTTGTCTTTC CTGCCAATTC CTCCCGTAAA 720

CTTATGATTA TCCTAGCCCA TTCCCGATAA AAATACACGG AGACAGTAGA TAGAGTTACG 780

AATAAACCGG TTTATTTATT CAAGTGTCTC AGGAGATTAT TGAACGAGCG TGGATACCAC 840

GCCGTCGTCA GTTCATGGTG GCATTGAGCA GCCATAGCAC CAGAGTCCCG GCGCCCGGTA 900

TCAGACACGC TGACCTACCG GGCGCCTTCG AGTCCGTACC CCGCGGCCTG GGTGTTAGAG 960

TCCGTACCTT GCAGCCCAGG TAGGTTTCAG GTACCAGCTG GTTCGTACCT GTTAAATAAA 1020

TCGCAGACGG GCGCTCACCC CTACGGTCAG GAGCACAAGA ACAACCAGAG AGAACAGATA 1080

TACGAGCAGG GTTCTGAACA GCAGACCCCA ATTGTCGTCT CTCATGCTTC GCTGAAGGTA 1140

CCAGTTGATG GTCTGAGAGC TATAGTCCAT CCTCACCTGA GGAACACACG CGGCATATTT 1200

CTTGGGGTCT CCCCACCTCG TAGACAACGT GATGTCCACC ATATCCACGG TGTGCGTCAC 1260

-continued

```
CGGGTGCCCA CCGATGTTCC ACTCGAAATA GGCTCCGCGC TCATCATGGT GGTACTGCTC 1320
ACCGGACACC TGCAGTCTGT CCATGTAAGA TTGAGAGACG ATACCCACGT TCACAAAGTG 1380
TTTCTCGGTG AAGTTGCCCG ACATCCTCCC CTTGAAGTAC AGCATGCCCA TATGGAACCA 1440
GCATTGGTTC TCCTCCACTC GAAAGTGGGC CGATCTGATC TCCGATACCA CCACATCCAG 1500
GGGCCGGGGC ACCGAGTCCG CGAGTCTCAG GAACAAGACG GCCAGGATCG CGAGCACCAA 1560
CACCGGCTTC ATGGCTCCGA AGGTCCGCTG CTCGGCTCCG CTCACCGCTC CGGTCTGGCT 1620
GCAGCAGTGC TTCGCTGAGA AGTAGCGTGT GGACTGAACG GTGTTTTTGA ATATATAGCG 1680
TTTCTTGGTG ACGTTGTTTC CCCTACGTAG TAGGCAACTA CGTGCCAAAA GAGGCGTTAC 1740
GGTACTTTCC GTACTGGGAT TTCCAAACCG GGACTTTCCA CACGGCGGTT TCAACACCGG 1800
GACTTTTCAC ACGGTGATTT CGGCACCGGG ACTTTCCGCA CGGCGGTTTC GCCACCGCTG 1860
ACGTTCTCAT CGCCGCCCAC GTCAACGGTG GCGACACCGT ACTTTCCCAT GCGGTTTATA 1920
AACGTCAAGA GTCACGTCAG TCGCCCACCC CCATTACACG GCGATATCCC GATAGGGCAT 1980
GAGGGGACCC GGGTGTCGCG ACATGTCGAC GACAGGTGCG GATTAGTGGT CGTGTCGCGA 2040
CATGGACGTG CAGGGGGATG TCTGTCGCGA TAGAGTTGAT GTGACAGCCC GCTACACCTC 2100
TCTGTCGCGA CATGCATACA CAACGGGCCG GCTTGTCGGC GATTGTCGCG ACATATCGTT 2160
ATCAGTTAGC GACCGGAGTT GTCTATCGCG ACATATCGTC GACTATCGCG ACAGAAAAAA 2220
TACCGTTCGT AGAGAATGCC GTGTTGAAGG AACGCGCTTT TATTGAGACG ATAAAACAGC 2280
ATCAGGAGCC ACAACGTCGA ATCCCACGTC CAGTCGATTC GTATGTTATG CTGCACAGCA 2340
ATGCTAGAAT AACAACCAGC AGGGTAATCC CGCAACATAA ATACAAAGTC ACAGCGAAGA 2400
ATCCGTGTCG TTCTATCAAG CGAAACGCGT TCCAAACGGC CCCGTCACAG ACGCAGTTAT 2460
TCATAAGCGT TAACAACCGG TGGCTAGGAT GAATATCCAA ATCACAGGGC AGTAGCCGAC 2520
GGACTCGTTG ACAGGTCAGC CTACCCTCAA GGTTCCTATC GTTCGGACGG GATTTGTGCG 2580
TTTTAGGCCT CTTTTTCGCC GCCTGCAAGC ATTGGTGCGC AAAGTCCTCA CCCAGCTGTT 2640
TCCAGCTATC ATCTGCATCT GTGCAGTCCC CTGTATCGTT GTAACAAACG GGTCTGTGCG 2700
ACTTCGTTCT CGGAACACAA GCTTGTTGTC GCGGAGACAG AGAGAGAAGG GTTTTCGGGT 2760
CACGCGAAGA CCGCTCACCG GGGGTCGGCA ACGCACACAT CAACAGAAAA CCGAGACGAA 2820
TCAAGAGATC CATAGTGAAG GAGTGATATC GACGTGCTTA CGAAACGGCG ATTATATATG 2880
TTCTCAACAA TACCGCCCTA CGTTGTATGA TGTAACGTGT GACGTGAGTC TGATCCAACA 2940
CTGAACGCTT TCGTCGTGTT TTTCATGCAG CTTTTACAGA CCATGACAAG CCTGACGAGA 3000
GCGTTCATCG GGGCATGAAG TACGCATTAC ACAAACTCCA TATATTTGTT ACGATAGAAT 3060
ACGGAACGGA GGAGGCTTTC GCCACACCTA TCCTGAAAGC GTTGCATTCT TTATGATAGG 3120
TGTGACGATG TCTTTACCAT TCCCACGGCT GCTTTGCGTG ATGATGACAT TCATCATGTA 3180
TTTCCATTCA CACATACCTT TTGTGCATAC GGTTTATATA TGACCATCCA CGCTTATAAC 3240
GAACCTAACA GTTTATTAGC CCTTGACAGG ATAGGTCAAA AGATTATATG TAGGTTTTCC 3300
GGTAAACCGA ATTGTGATAT TTCTCTGCAG GAAATAGAAC AGCCTGGTAC CTATAAAACG 3360
GACAATGCAG TACTGTAGCA GCGTAACCAA GTAGGTCCAC ATGAACACGT ACAAAATTAT 3420
GGTAAGCCAT CGTTTTTCAT ACCACAGCCT GTAGCTGTCG TACATGAATG AGGACGGTCG 3480
AGGAACCCAG GGTAGTTGTA ATTGGGGGCG ACATTCGTAC TGTCCAGAAG ACAATTGCAC 3540
GGGTTTCAGT GAGATGAGTA CTTTAGCGAT GTCGGCGGGG GCGCTACGTT TCACCGTGAC 3600
GGTGAGAACT TGACCGTCGT TTTGTATTTC ATGAGGCACG TTATACAAGC CACTGGTATC 3660
```

-continued

| | | | | | | |
|---|---|---|---|---|---|---|
| ATGAAGGATG | ACCTCTGATG | CGATGTGAGG | ATTAAATTGT | CCCTCAAACC | GCCAAACGCT | 3720 |
| GGTCATGTTT | CCACCGTCAA | TTACGCAGCT | GACGGTGTGA | GATACCACGA | TGTTGGACTT | 3780 |
| AGGTTTGGGG | GCTAATTGCC | TTTTTACAAA | TTCCCTTCTG | TATTGCAGGT | CCTGCTGCCA | 3840 |
| CTGCTTTTCC | GTGCGGAAAG | TCGCCATGTC | TTCCACACGT | GTGGCGACGA | TAGACGCCAC | 3900 |
| CAAGGTAGCT | ACCAGAAGCA | GCTGGATCCG | CATGGCATTA | CCGTATGTCA | ATTAGAAAGT | 3960 |
| TGAGCGGACA | CGGTTATCGT | TCCTGGCGGA | TATAAGTATA | TAAACGCGAG | TTAGCCTTTC | 4020 |
| CCGTCCGTTT | TGTACACCCG | TTCCCCACAC | AAATGACGAA | TACGACCTTT | TTTTTATAA | 4080 |
| AAATAAACCA | CGTGTATTAT | ATAAAAACAT | TTACATAGAA | AAGAGACACA | CGGATCAACA | 4140 |
| TAAGGACTTT | TCACACTTTT | GGGGTACACA | GGCGTGCCAC | CGCAGATAGT | AAGCGCTGGA | 4200 |
| TACACGGTAC | ACAGTCCTGG | CCAGCACGTA | TCCCAACAGC | AGCACCATCG | CCATACAGAT | 4260 |
| GGCGATCACG | ACCCCGAGCT | CTAAGTGTCT | GTATTCATAG | TGTAGTCGCC | GCAGGTTATC | 4320 |
| CACTGAATTC | CCGTAACTGA | AATAACGTAT | ATGGTACCGA | GGCTGGCACC | ACATGGGTTT | 4380 |
| GCATTTGGTG | CACGGCACCA | AATGCAGAGT | GAGATGGTCC | AAGTCCGTGG | GCACCCACTG | 4440 |
| GCGCAAACGG | AATACGGCTT | CGGTGGTCTC | CACGAGGCAC | TCCGGGGCGT | GCAGACGGCC | 4500 |
| CCACTTTCGT | CCGCGACGGC | CCGACCAGCC | GACCCGAGCC | ACTATCCCTT | TCTCGGGATA | 4560 |
| GAACGTACCC | TGTACACGCC | ACACAGCGTC | CAACACGCCG | TCCTTGACGA | CGCAGCTGGC | 4620 |
| CTGATAGCTG | GACACGTTGT | TAAGCGGCGG | AAAGCGAAAC | TGACGTGCCG | GCGGAGCCAC | 4680 |
| ATAGTTCGGT | TCACCGTGTT | GTCGCGGTTC | GTCCTCCCTA | TAGTAATAGT | AGTCGTCGTC | 4740 |
| CTCATAGGGG | TTGCCGGCGT | GAGCCAGCGT | TACCCAACAG | CAGCCCAGGC | CGACGAGGAG | 4800 |
| GCGCAGCCAC | CGCCTCATGG | CGGCTTCGCC | AGTCAATCGT | CTTTAGCCTC | TTCTTCCCGT | 4860 |
| GAGGTCCTTC | CGGTGGCGCG | GTGCCGACCT | CGGACCCAGG | GACGTATCCA | CCTCAGGTAC | 4920 |
| ACACAGCAGG | CTACCTGGAC | ACCGAAGCTG | AACAAGGCTA | CGTGTTTCAC | AAACTGCACC | 4980 |
| AGTACCACAT | AGAGGAATGT | CAGGTAGCGT | CTCTCCGCAA | ACAGCCGTTC | CAAGTCTGAG | 5040 |
| GGCGTTACCC | GCAGCGGCAA | CCAGGGCAGC | CTGGACGCCG | GCCGGCAATG | GAGCACGCTC | 5100 |
| CGGTTACAGG | CACTGCAGGG | GTAAACGGTT | AACATCACGT | AAGAGAGTCG | TGCGTCCACC | 5160 |
| TGTGGGAGCT | CAGTTTCGTA | ACGTAGAGCC | CCGTCATTTT | CCAGCTGGGG | TGCGCCGACC | 5220 |
| TTGAAATGGG | TCGCGCTCCG | CTCGTTACCC | CAGGTGCCGT | AGGCTCTCGG | GGCCGTATCG | 5280 |
| GAGAAGTTGC | CACGCACAAG | CCAGGCGGCC | ACGAGTACCC | CGTGCTGGAC | GTAACATTCG | 5340 |
| GACACGGAAC | TGGAGACACG | GTAGCCGGAC | ACGTCCCCAA | ACCCGCGAGG | GTACTGGGGC | 5400 |
| AGACGGACGG | ACTTGCTATT | TGACAACGGA | CAGATACGAG | ACGACGAGGA | CGCAGACGAC | 5460 |
| TCGTCGCTGG | ACCACGACAA | CCGGAGCGAC | TCCTTGGAGC | GGCTCGAGAG | TACACTTACT | 5520 |
| GCGATCAGAC | ACCAGTGCCA | GAAGAAGGAA | CAGGTGGACG | GGGACCACAG | GATCATAGCC | 5580 |
| GCCGGCACCG | CGGCCGGCCG | CAGGAAGCCG | CCCGGCGCGT | CGTCTGTGTG | CGGGAGCCGA | 5640 |
| AACACCGTGC | CTCTTTATAT | CGTCCCGACG | TGACGCGAGT | ATTACGTGTC | AGGGGAAACC | 5700 |
| CCCGTCACGA | CGAACGTGAT | TTGTAAGTGA | CGCGGGGTGC | TGACGGGGTT | CGGCCCGAGA | 5760 |
| GGTGACGGAG | CGCCTCACGT | CAGTATGATG | TCCGATCCGC | GTCAGCCCCG | ACGTGGTTGT | 5820 |
| GGTCACCGAA | ACCCACGTTT | ATATGGACGT | TGAGAGCAGC | GCCTGACCAC | ATGATTCATC | 5880 |
| ATACCATTTC | TCGGAATCGG | GCCCATGCCG | GGAAAGCACA | TTCCTTTTCA | GTAAACAACA | 5940 |
| ATGACATCAT | AACAAATCAT | TTTATTCGCG | AGGTGGATAA | TAACCGCATA | TCAGGAGGAG | 6000 |
| GGATCGGGTG | ATGACGCAGG | CCCCGCAGAA | CAGTCCGAAA | TAAATTTTTA | GTATTGCCCC | 6060 |

-continued

ATAGTCGCCT AGATACCAGA GGTACGTTAA GTTCATCAAA ACGCCCATCG GCGTCCCGGA 6120

ATCGTATACC GGGCACACGA AGCGTTCATA ACAATCCCGG GAGGCGAGTG TTAGGGTAGC 6180

AGAGTAGTTT CGGGGTCGGT TTCCTTCCGG CGACGACAGT TCCGTGGGCA GCAGAATGTA 6240

CAGCGCCTCG GTAGCTGTCG CGGTGCCTTC CACGAGGATG GGCTGCCGGT GCCTTTCGTG 6300

ATTTTCCCCG TCGTGTAGCC AAGCCGAGGC CCGCAAAGTC TTAGGCGAGG GGAATTGTCC 6360

ATAGAGTTTC ACCGCACCCT TCAGTACATG GTTCTGAATA ACACAGCCGC ACGTGAAGTA 6420

GGTAGGTTCT CTCGTCTCCT CCGTGGCTGC CGCCACCACT CCCAGCCACC ACAACAGGCA 6480

GATCGCCAGA GGGTTCCGGA GGCTTCCCCG GCGTAGCATG GTTTTGGGTT AAAGCAAAAA 6540

GTCTGGTGAG TCGTTTCCGA GCGACTCGAG ATGCACTCCG CTTCAGTCTA TATATCACCA 6600

CTGGTCCGAA AACATCCAGG GAAAATGTCG GTGCAGCCAA CCTTTCACAT ACAGCCCCCA 6660

AAACACTTGA ATCACTGCCA CCATCATCAG CGTATACTGC GCCGACTTAA TCGTGAGCGC 6720

GTAGTACGCC ATTAGACGGC GATCTTCGAA CAATAGTCGT TCGATGTCCT CTAACGAGCT 6780

CCACAGGGGA ACCCAAGGCA CGAGGCACCG GGGTTCGCAC TCTACATAAT AAGTTTGGCA 6840

TTGGTGGCAG GGGGAAAAGT AGAACAACAC GAGTTTTGTG CGTTGGGGAA CACGATAGTC 6900

CCGGAGCCAG TAGCGTTTTG CGACGAGGCT TTCGGAGACG TCCTCCACCG GCGTCGGCAC 6960

TCGATCCGCG TAGCCCTCCA GCGTCTGGTA GTACACCCGG GGTGTCGGCG TGGGCACGGA 7020

CAGGTTCCCG CGCAGGGTCC ACAGAGCCTC CAGTCGACCG CCCGATCGGA GCACGCAGCG 7080

CGCCTCGGAA TACTCTACTC GGTACTCCGA AACATCGGAC AGAGGCGGTA ACGGCTCCGT 7140

CTCCACCAAG GGCGGAGGTT CATCGAAAAG AGTCAAGGAT AATTCAGGCA TACTACCCGC 7200

GACCGGGGCC CAGAGGGCTA GAATAAGCAT TACAAGGTTC AT 7242

( 2 ) INFORMATION FOR SEQ ID NO:4:

( i ) SEQUENCE CHARACTERISTICS:
( A ) LENGTH: 18994 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

AAGCTTTATT ATGAGACATC ATACACATAG TATAGGCGAG GTGATGGGGC GGGGAAAGAG 60

TTGGAACCGA AAGACAAAAA AAAAAGCCTA GTCGTACTCG GGATCTCTGA GCGAGACGGG 120

TTGCATGGCA ACTTTCATTA GTTTGGGAAT CTGCCAGCTG GTGCTGTTCG AAGGTTCTTC 180

CATTTCCGAG GCGGTCAGTT CATCGTACAC CGAAACGTAG TACCTGATGG GGTCCTCCTC 240

ATTGTCCGAG AGGTGAGATT CGATGGTCAA AGGCGAGCCT CTCCCATAAT TGGGATTCAC 300

GAACGACGTG TCCAAGTTGC CATCCTTTCT GAAATAGATG ACGTTCTCAG GATCATGTTT 360

CATGCGCTCG CGGGCCGCGG ACGCCTCCTC CTCCTCGTCC CAGTCCCGAG TTTCCAACCG 420

CTGATAAGGG CTCGAGGAAC AAAATCCGGC GGGGATCTGA GAACCTCGTC GGGAACCGCT 480

GCCAAACGGG CTGCTGCCGC CACTGTCGTC CGTGTCGTCC AACAGGTTGA CGGCCTCTTC 540

GTCGGCGAAA CGAAAGCGGC CCGGGTGCTT GCAACACGAG GAGTAAACTA CCGCGATCAG 600

TACCGCTATG AAGCTGAAAA TGGAGGTGCC TGTCACGATG TAGAAGAGGA TAGCCAGCAC 660

TTTCATGATT TCGTCATTGC GCGCGTCGTG AACGGAAGAT TCGCGGGCAG TGGTCATGTT 720

GGTTTCGGTT GTAGGTTCGC TACTCGTGGT GCTCTCGACG GTATTTCTGC TGCTGGTGCT 780

-continued

AGTAGGGACG TTTGTGCTGC TGGTCATATT TGTAGCGTCG CTGAAGTCGA TGTGAAGCAG 840

CAACCCGAAC GCGACCAGGA CCAGGAATGT TGCGCGAAGG AGACCCCGCG GGGCCGGCAT 900

TCTTGAGACG TGGCGACGTG GATTTCTTGT TATGTCCGCG AACGACGTGT AACGAGGACG 960

TGGTTTCCGC AAGCCTCTAC CGACGCCGCG ACACCAGGTA GGTTATCAAA ACGCGAGCCC 1020

ATATCGCCGC CATCATTGTA ATCAGCAATG TGTTGAGGTA CTGCACGATG AATCTGTCTA 1080

GTGACACCAG CCAACCCTCT GCTTTTGCGG GCAAGCGCGC TTTCGGTGAC AGGGTGTATC 1140

GTACGTAGCC GCGGGTCAGG CGCGCGTTGT AGCGGTACAC GCAGAAATCT ATCCACAGGC 1200

CAACGCCCGG CTGTAGCTTC GGATGGTGGA TAATAGCGCG GTGACGTACG CCGCGTGGCT 1260

TTAGAATCTC CACCTGTAAG GCCATCTCCT CCAGGTAGTG GGTCTGACTG CGACGCAGCG 1320

TCCAGTTCAT GTAAAAGTCG GTCTCGCCGT GTCCGGCCAC GAAGAGGCTG CTTACTAATC 1380

CAGTCTACAT TGTGCCATTT CTCAGTCTGA TTGCATTTTT TAGAGTTATG TTGCCACCAA 1440

CGTATCCTGT TACGTTGATT ACCTCGTAAC TGCGGTCGCA TCTTTTATGG ACTGTATAAT 1500

TGAAACCATC ACAAGTAACG GTCGTGGTGG TGTTGGTACA TGTGGTAGTC TCAACGTTTG 1560

TATTTGTCGT TGTGGATATC TGTGTGGTTG TTTTCGACGG TTTTGTAGAA ACGGTGGTTG 1620

CTGGTGCAGT TGCAGTAGAG CAATTTATAG ATTCTGAAGT GCTTTTATTG CTGATAACTG 1680

TTGTACTGTA TGTTGATGTG GCTGTCTCAG TACTAGTGGA ATAGTTAACG GTAGTACTAC 1740

AGGGACATTG ACAGGAACAG GTTTGATTGC AGCTTTCTGA TAACGCGGAT ATTAGTATCG 1800

TCCACATAAC CGTAAATCGC CAGTCCATTG CAATATTAGT TCTCGCTCAA TGGGCATTAA 1860

TATTCCTTTG AACGCTGAGC CTTACAGAAT GTTTTAGTTT ATTGTTCAGC TTCATAAGAT 1920

GTCTGCCCGG AAACGTAGCT CAATCTTCAT GTTCTGTGTG ATATCGAACA ATGAATTCTG 1980

ATTCACTGAC GGTGTCTTGC AACATATGGT ACTTTTTGTT AAAGGCTCGT CGTGCAAAAA 2040

ACAGAACTAT GCAGGCCATA CAAACCAACA CGATGGTCCA TACGGTGCGG CTTCTTTGCG 2100

AGCTATGATA GAGATTACGT TTGTGGTGAT GTGTATTGTT AGTATGTTGA CTTCCTTTCT 2160

CTCTATCTTC ATTTTCGATA TCGGTGTTGT ATCTAGGGCA AACGAAAGTA GCATTAATAG 2220

CTTCAGTATG ATTTTTTGGT GTTACTAATA GGTAGAAATT TTCATCTTCG TGATGTCCTG 2280

TGAAGTAATT TTCTTTAAAA CAACGTCTGC TGTACCTGCC GGAATTGGTG ATATTTAGAT 2340

CGTACAGATG TAGTTCTGTG TTGTTGCACG AACGACATAA GTCATGGTAC AGTGAAGGTC 2400

TTTCATGTTG AGAATGACAT ACAGTATGAG AGGTAAGGAT GCGTAACCAA TACCAAGATT 2460

GGGTATGTGC GTTCTTACGA TGACCTAGAT GATGTCCGTG TGTGGATCGA TTGTAATGTC 2520

GTATCCAGGC GACTGAAAGA CAATCCCACG TAGAATTACC TTTTATGGTG ACATTACTCC 2580

CTTCTATTCC TGTTGTATTA GTTTCTTTGA AACGTATGAT TGTTGTCTCT GTGTGACAAG 2640

CGTTGGAAGA GTTAGTACGG TTGTACGTGG TGTACGTTGT GGCGCTGCAA TTTGTAAGCC 2700

ATGGCGTGCT TATAAGTGCA GTATTAGTGG ATACGTTGTG CGAAGTTTCA TCTGACGTGA 2760

TAGTTACGGT GATTGTTGTG TTATAAGATG ATGTAGCGTT TGCTGTTACG TTGGTAAAAG 2820

ATAATATAGT GTTGGTATTT GTTGAAATCA ATTCTGTAGT GGCAGCCGTA TTGGATATAT 2880

TAGCATATGA TGTATTGAAT GTAGAATATA CGGTTGTGAA AGTACTCAAG TCGGAGGTAA 2940

CGTTGGTGAT GTTGCCAATG GTTGACGCTT GTGAGGTGAC AGATGTGTGT GGCGTCGTTG 3000

ATGTGTTGTT ATTCGGAGTA GAAAATACGC TGGTCACAAA GGTGGTAGAA GCAGTGTTGG 3060

GTGATGTGAT GGATGCAGTA TTGGTAGTAG TACTGTTGCA TGTAACTCTA TGCAGAATAT 3120

AGAATATTAT GATTGTATAC GCCGTATGCC TGTACGTGAG ATGGTGAGGT CTTCGGCAGG 3180

-continued

CGACACGCAT CTTTTACTGT AAATCCCCGT CCACCGTCAA CAACAAAGGT TCCGTATCTA 3240
GGTCCGTCCG CAGATGTTCA GCGTCCTGTT CCCCGATTCG TTGCGATCGC AGGAAGCAGA 3300
TGACCAGCGC GCCAACAAAG ATCATCATTC CCGAAACCCA GGCGCAATGG AGTGAGAGGC 3360
CGGACCACTG GCGTTTTAAA TCCGAGATAA TTGCCCGGTC TGCCTCTTGG GAATCCGTAA 3420
CCACAACTCT CCCTGGTCCC GGATAAAAGC ATCGACGCGT TTCCAAGGCT CGGCAGAAGC 3480
TACGTGGGTG GATGATGAGG TAGAAAGCCT CGACATCGCC GGTATACTGA TCCTGCAGGA 3540
GGTAGACTCC CGTATCTTTA ACCGTGAGAT TGTACAGCGT CAGATTTTGG CGCGTGCACG 3600
CGAACGCCGC ACCGCCCTGA CGCGTGGTTT CTTTATAGGC GTCTGTAATG ATACAAAGTG 3660
GCGGCATACG ACGCATGTAT CTGCTGTAGA TATCATAACG CTGCCAGACT ACGCTGTGAT 3720
GGCTAGTGTT AAGCCTGGTA ACCAGCGTGC GTGTACGGTC CTCGCAGGTG GCACGGTAGT 3780
TGGCGAGCTT TAGGGGTTTT TTGGTTGGTT CGACGGCGTT CGATGAACTT CCCTGAGTTG 3840
TGAACAAAAA CAGCGACGTG ACTATGACAA GCGTGAGGGG GGTGCTGTAG GTCTGCATGG 3900
TGCAAAACAC GTTCTCGCCT TCCTTATCAG ACGTTGTCGT CCTCGTCCTC TTCGTCGTCT 3960
GTGCCCGTCG GTTCGATCAA CGGGGAGTTA TCTTTCTGTC TGGAGGGTCG GTATGGAATC 4020
CGTTCGTAGA TGTTCTGCTT TTTAGCCGCG TGTTGTTCCA GCTTTTTGCG TGTCAGGCTC 4080
CGATAGGCCA GACATTGATC TACCTCGGTG CCCGTGTTGT TTTTCTCCTC CTCGCGCGCG 4140
TAAATTACAA AGAAGACCAC CAGCAGGACT ATCAGCGTAG CCACGAACGA GCCCGCGCCC 4200
CAGGCCGAGT ATGCGCCTAG CATGGTAATG GGTTCTGTGA TCCGGCATTT GCACATCGCG 4260
TGGCACTTGC TGCCATTGCC GGTATTAGAT GATGTGTTAT TCGGACTGCA CTTGCACGTC 4320
AAATGGGTAT TTTCTGATTT CACGAGACAG TTGGTGGCGA CTTTGGTTTC GGCGCAGACG 4380
GCCACATAGC TTACCAAGCT GAGTGCCAGA AAGCACACCG CGTGCATTAC ACGCGGATAC 4440
ATATTAAAAC ACCGTGTTCC ACAAGCACCG CACACGTCAA TCCTCCCCGC ACGGTCTTCA 4500
GCCCGCCCAT GACATGATCT CCCTCACGTT ACCCTTCAAC ACCCTGTAGT ACTCTGTCTC 4560
GGCTTCCGGT CCCCATGTCC TAATTATAAC AAAACACCGT GACACTGTCC ATCTCCCTGT 4620
CTTTTTGCGC CGCCGGTCCC CCCCAAATCA TGTCTCTAGA TGCCGCCGGC CACCAACCGG 4680
AGGCACGGCG GCTATTGGAT TCGGCATTGG TGCGCCGCGT CTTGGCCTGC ATGATCATCG 4740
TCATCATGAT TGCCATTAGC ATCTGGATCC TGACCTACGT GCTGTTTCTC TAATAAGAAC 4800
CCCGGCCCCT GACGGTAATT TTCCTTTCTT CTCCGTTTCT CCTCAGCTGC CGTACGTGAT 4860
GCCTCACGGC CATCTCCGAC AGGCCCTCTC CCCGACCTCC TGGACATGTG AGGGCTTGTT 4920
GCTCCTCCTG GGATTGCTGG TGCTCTTCTT TCACCACCAC AACCAGTCGG CCGTGGAGAG 4980
GCGTCGCCGC GTCTCGTTCG TCGAGGCCGA TCGACTGCCG CATGAGAGCG GGTGGTATTC 5040
TTCCGATGAC GACGGAGACC GGGACGGTGA TGAGGAAACT GGAGAGAGCC ACAACAGAAA 5100
CAGCGTGGGA CTGTCCGCTG TTTTTAGCTG ACTGGCGTGC GACCTGTAAA CCGTTACTCG 5160
GGTCTCAAGA TGGTTTGGAA GTTGTGACTC ATCTTCCTGT GGGTGATACC CAACCGGACG 5220
CGAGTGTTCC ATAAAAGCCG GGCGCTCCGG CGAGACCATG CCATCCTCGC CTTCGGACGC 5280
CCCGCTCCTC TTCTCTCTCC TCTCCTCCCC GCTGCCGCGG CCATTGCCGC CGCCGCCCAT 5340
ACCATCGGCA TGTCGGCCGA CAAATCGCAG CTGTCTTCGC CGCCGCAGCT GTAGCAGTTA 5400
ACGTCGCCGG CCTCCAGGAG GAGATGGCGC TGTGCGTCGT CTCTTCGTCC CGTCTCCCTC 5460
TGTGGTCGTG GGTGGTGCGA GAGTACACGA TGGGTGGCTC TCGTCTCGGG GGACCACAGG 5520
GGGAGGGGGG TAATTTATTA TTCGTATTAC TGTAATTTTG TATCGCTTAA TTTGTTTAGA 5580

-continued

| | | | | | | |
|---|---|---|---|---|---|---|
| GCCGCACGCT | TGACAACGCC | TTGTATAGCC | TTATTTATCC | CGATGACTTT | TTTCTCCGTA | 5640 |
| CAAGAAATGG | ACGTCACTTG | AGCAGACACA | GTTTCATCGA | CCACGACAGT | CTCATGATCT | 5700 |
| GACTACCTCT | GACCCGCCAA | CGAGAAAACC | GAAAAGTAAA | AGATGACCGC | GCCCTCGGAG | 5760 |
| TCCTTTTTTC | CTTTTCAATC | ATGAAAGCAA | GAGGCAGCCG | AGAGAATGCC | AGTAAGAGAC | 5820 |
| GACCATCGCA | GACACAGTAC | GATACTCATC | TTAGAACGAA | CCAGCGAATA | ACCATCACAC | 5880 |
| GTACAGCAGA | ATCTCATGAA | CTAGTCAACC | AACGTCATAA | AATCTTCACA | CAATCGTTTT | 5940 |
| TGCGAACTTT | TAGGAACCAG | CAAGTCAACA | AAAGACTAAC | AAAGAAAAAC | CATCTTGGAA | 6000 |
| TTAAAAAAAG | TAGCATCGTT | ACCTTATGAA | CCAGCAGCAT | TCAGTATATA | CACCAGATAT | 6060 |
| AATATATTTA | TTAATGTATC | CTCTCTTTCT | CCTGATGTAA | TTTTGTTTTT | GTAAATTCAA | 6120 |
| TTGTTGAAAG | TCTCTCCCTG | GGGGAATTGC | ATATCTTATT | GATGAAGAAG | AAATCCCTGC | 6180 |
| CATATGTGTT | GTCAAACTAT | CATTATTTCT | CTATATGGGT | ATTTTTTTTC | TAAGAAGCAA | 6240 |
| AAGACTAGCA | GCAGCCAAAA | TAAACCTGAT | GAAATCTTTA | ACTGAACTCC | CAGTGGTCTG | 6300 |
| TGTGTATATT | TCTGTTGGTG | GTCGGTTGTC | TGAACCCGGG | TGGGTTGTTC | GGAAACGGCG | 6360 |
| GGACGGGGAA | ACGGATGGAA | ACAGCGTCGC | TATATACGTG | ACTTTTGATC | TAAACGGACG | 6420 |
| TCGCTAGGCT | GACAGTTTAC | GAATTGCTAA | ACAAGATAGG | AACAAAACAA | GCGGGGCTTT | 6480 |
| GCCTGGTAGG | ATTTCCTGTG | GAAACAATAA | CCGGATGTGA | TTGTGGCTGG | TACATAAGCT | 6540 |
| GGTTCTGGCT | GCAAGCGCTT | TTCACTGCAT | TAGGTTTGGC | GTTTGCTTTT | GCCTGGGAAC | 6600 |
| GCTATGGCTA | TAACGGGAAA | GAACCGGTTT | GGCAACATTC | CATTGTGGGG | GGGGGGTACT | 6660 |
| TATAGCGTGC | CTAGCTATGA | CGTTGATATA | TGTGGATGCG | GATAATACTC | GTAATGAGCT | 6720 |
| AAAAGCGACG | ACTGGTAGTA | ATTTTACCAT | TACGCATAGG | AAAGATCCGT | TGACAACTAA | 6780 |
| GTGGAAAACC | GTTTTTGGTA | ACAATGGTGA | TCAGTGGTTG | TGCAACGTTA | CGGGTATAGG | 6840 |
| TAATGCTACT | GTGAATAGTA | ACGCAACTAT | TTGTGTGTCG | AGCTGTGGTC | ATAATACGTT | 6900 |
| GGATTTATGT | AATTTAAAGT | CGGGAGATTC | TGGCTTCTTC | GATCTGTCTC | GTTGGTTCGG | 6960 |
| TGAAAACATG | GATGAATACA | GTGGTGATGT | GTGGCACTTG | GAAGTCAGCT | AAATGTTGTA | 7020 |
| TCGCTTAGTG | AATTGGTGTT | CTTACAGTTT | TCATGTAATA | AACTACGTGT | AATTCGTTAA | 7080 |
| ATTTGTGTGT | TTTTTTGTTA | GTATTCTGCG | TAACGGTGGA | ATAAAATTGC | GTTGACCTAG | 7140 |
| TTAGATTTCC | TGTGTAGAAC | AATGACCGGA | CGTGCTTGGA | CTGGTACATA | CGCAGGGGCT | 7200 |
| GGACGTGGTT | ACCGGTCACT | GGACTCGGTT | TCGCTGTAGC | TGTGGTTCAA | CCTGAACATG | 7260 |
| GCTCCCAGAG | CTGCTAGGAA | CCGGTCCAGT | CACATTTTTT | GGTGGGTGGG | GGGTACTAAA | 7320 |
| AAAGTGTTTA | ATATTTGGGT | TTAATGATAA | AATCCAGGTT | ATGGATATGA | GGAAACTGAA | 7380 |
| TACCTCGCAG | GGTCGAAATC | TTACCACAGT | TGATGATAGA | AGACGGTTTT | CCATCGGGTG | 7440 |
| GGAAACATGG | GATAACGGTG | GTGACTAATA | ATGGTACAAC | GGTCGTCAAT | ACAACAGCCT | 7500 |
| GTGTTTCAAG | TTGTTCGCAT | ACGTCGCTTG | TGCTTTGCAA | TATGACGCAG | CAGACTGATT | 7560 |
| CGTTGTACGG | AGTGGGTCAT | CGGTTGAATG | ACGAAGAAGA | TGGTGAACTG | TGGAGAGTTT | 7620 |
| CGGTTTCTTA | ATAATCCCAT | ACGACATGTG | TTCATTTATA | TCTGAATTTT | AGGATGATGA | 7680 |
| CTATAGTATA | ACTCTGGGGA | ACAAATATCA | TACGTTAATC | ACTTTAAGTT | ACGCCGTTAG | 7740 |
| GAAAAGAAAA | TCAGTCCGAA | TGAAGCATAG | TCAGCCGAAT | GATACAGCAA | TAGCTTGTTT | 7800 |
| ACAACGTGTT | CTTTTTTACA | TTATGAACGT | GCCTTGCTTT | TTATACACAC | ATGGAGACAG | 7860 |
| AGGTCCCTCA | GCCCTTGTCA | CGACAACTCC | CTTTTTCTAA | ACCGTATGTG | CTCCAAACCG | 7920 |
| TATCTCCTCA | TCGTCACGTG | AAATACCATG | GGACCCCTTT | TCGTCACACA | CGTCTTTCCG | 7980 |

-continued

| | | | | | | |
|---|---|---|---|---|---|---|
| CTTACCCAAC | GCGTCAGCCC | GCGCTCGGCA | GAGCTACCAT | ATAAAAACGC | AGGGGTTTAG | 8040 |
| CAGCTTCCCC | AGATCGCTGC | TGCCCCGGCG | TTCTCCAGAA | GCCCCGGCGG | GCGAATCGGC | 8100 |
| CGGCTGGTCG | GTCGGCGCTC | GGACGGATGG | GGAGAACGGC | GGTGACTTAG | CCGCCCGTGG | 8160 |
| CCGGGAGAAG | ACGGAGGAGC | CGAGATGACA | ACAGCAGTCG | TGGAAGGGTC | GCCAAGCCCC | 8220 |
| GGTCCTTCTC | TTCTGTCTGG | TCGAATCTTG | TTTTCTTTTT | TCAACCGCTC | TTTTTGTCAC | 8280 |
| CTTTTTATGT | GAGTTTCTCT | TCCGCGTCTC | CCGGCCGTAC | CATCCACCCA | TGCAGCATGC | 8340 |
| ACGCGTGTAT | GTATGCATCG | CCTCTCCTCC | GTCCCGACTA | CCATCAGCAG | TACCACTGCC | 8400 |
| GCCACCCCCA | GCGCCACCAC | CGCTGCCGTC | GCCACCGCGT | TATCCGTTCC | TCGTAGGCTG | 8460 |
| GTCCTGGGGA | ACGGGTCGGC | GGCCGGTCGG | CTTCTGTTTT | ATTATTTTTT | TTTATTTTTT | 8520 |
| ATCTTCTCCT | TTCCTTAATC | TCGGATTATC | ATTTCCCTCT | CCTACCTACC | ACGAATCGCA | 8580 |
| GATGATAAAC | AAGAGGGTAA | AAAGAAAAAA | GCTACAGACA | TTTGGGTACC | TCAGCTTTCC | 8640 |
| GATAACTCGA | AGAATTCAAA | GTCGACGATT | CCCAACAAGA | GAAAACAGAA | CAAAAACAAG | 8700 |
| GTCATTTTTA | TTTATCCTCA | TCGTCAACAA | CAACTACCGA | CAACAACGAA | ACACCACCAA | 8760 |
| GAATGTCAAT | CCGCAAGGGT | GTTCCTGCCC | CCTCGACGCG | CCTGTCGCGA | TCCTCATGGC | 8820 |
| GAGGACCGCG | ATCTCCGTAT | AGGTAGATGA | AATTATCCCG | TGTCCGGTCC | TGATTCCCCG | 8880 |
| CATGCCCTGC | ACATCCTGAC | GCGTCGGTCA | GCAGCCAAAC | AATCATAGGA | AATGAACCAG | 8940 |
| AAGAACAAAA | AGATCATCTC | TCTCGGTGTA | TAGCAACACC | AACAACAACC | GCATCGCAAC | 9000 |
| ATCTTCATCC | GCAAGACGGA | AAGAAAACAA | CAATAATGAG | AATGAAATCA | CCACAACCAA | 9060 |
| GCCAGATTTC | ACGTCCATGA | GTTTTTATTA | TATTATTATC | AAAACGAAAA | ACAGAAAAAC | 9120 |
| TGTCATAGAT | AAATATAAAA | AAAAATAGAA | ACCACAAACG | ACTACTAGTA | CTCCAATCTT | 9180 |
| AGATGTATAT | GCTCCTAGAT | AAGATTTAGT | ATTACCATAA | TCATCGAAGA | ATGAAAGACG | 9240 |
| ACGATGATTC | CTTACCGCTC | CTGCCACCCG | GTCTGTATGT | AGAGAGAGAA | GAGAGAAAAC | 9300 |
| GGTGAATCCA | AGATCCCCGG | GTCGGCGTCG | GCATGCCGCT | GATCGCAGTG | GCCCCACCTC | 9360 |
| GGCATGCCGG | CGCCGGGCGA | GGAATTGCTC | ATGAAAAAAA | GTATCTTTCT | GTAAAAAAAG | 9420 |
| AAAACAATAC | ATGATTAACC | GAAAAGAAAC | CAACAAAAAG | AACCCGAGAT | CAGTCGATTT | 9480 |
| CGATCACTAC | GATAAACACA | TGGAAGATTT | CTTGAAAAAA | GAAAAGAGAA | AGAGACCACC | 9540 |
| TTCCCGGCGG | CGGACACGCT | CCTCTCCGTC | GCCGTTCTGC | ACCATGATTC | GATCAATAAC | 9600 |
| AACATCATCA | TCGGAGACCA | TCTTTTAATC | AATCAGCGTT | GCAGTAGTCG | ACTCCCTGGA | 9660 |
| CACGAAGGAG | TCATCCATTT | TTATCCTCGC | ACTTCTTCGC | TCTCAAAGCC | GCCTTTAAAG | 9720 |
| TTGAAATGAA | AGGATGGAAA | CATGGAATAC | AGTTTTAATT | GCACGTATCA | CCATTTTACT | 9780 |
| ACAAAAAGAA | AAAAAAACAA | CTTACACATA | GTATTACCTT | AGGTTTACGG | ATAAGTAGAG | 9840 |
| TGTAGGCGTT | TTTGAAACAG | TTCAGCCAAT | GCAATCTTGT | CTCGGCATAA | TCACTCTTTC | 9900 |
| TGCATATAAT | AGTAGTAGTA | GATTTATTCA | CATCAACACA | GCGAAAAACT | CCAGCATCAA | 9960 |
| AGTACACCTA | GAGACAGCCC | TTAAAATATA | GTTTGCAGCT | TTTAGATGTA | CTTACACCAA | 10020 |
| AGAAGATTAC | CGTCCTTACG | AGAAAACAGA | TACTCGGATA | TAGGAATCAA | GACAGCTCTG | 10080 |
| CACTGAAAAC | ACACTCTCCT | GTCACGACAC | CGCGCCACAC | CAGAGGCGTA | CGCGTGACTT | 10140 |
| CATCGCAACG | ATCCATCGTG | ATGTCCCTCG | CAGAACCTAA | AAAGACCAAA | AAAAAATCTT | 10200 |
| GGACCACAGT | TGTCGATACT | TGAAGACAAT | ATTCTCGTGA | GAACTTTGAG | ATTCGCACTT | 10260 |
| GAAACCTCTT | AGGATCCACA | AAAACAACAA | CCTCTGTATG | GAAAATGCGC | TATTTTATCT | 10320 |
| CAGCTTTTCT | CCCAAACCTC | GGTTTCTTCC | TATTCTTATG | TTTTCCCTAG | TATATTTGCC | 10380 |

-continued

| | | | | | | |
|---|---|---|---|---|---|---|
| TCCTTATAAG | AAAAGAAGCA | CAAGCTCGGT | CGCACGGATT | ATTCCTTCTG | CTAATCTATT | 10440 |
| ATTTTGTTCC | TTTTTTTTTT | CTTTGCCTTC | ACCCTCTTCA | CTCCCTGTAG | CAACACAGAG | 10500 |
| TAGTAGACAC | AATAAATGAG | AAGTTTGCAT | GCATTTGTCG | TGTCCGTGGT | TTGTTATGGC | 10560 |
| GTGTGGAGTG | CTCGGGATGG | GTGGACGTGG | GGACGGATTC | TTGAGGCTAC | AAAGATACGC | 10620 |
| GGAGACGTCG | TGGCGAGGGG | ATGGGTTTAT | TGGATATCGG | TGAAGCAGCG | TGGCGGCGAA | 10680 |
| AGACGCGATC | CCTGGGCTGG | TAGATCCCCC | TACCCCGTCT | ACCAGGGACG | TTTATCCTTT | 10740 |
| GGACACGTAA | ATGTCTCGGC | CGGCATCCAC | GCGCCACGTT | CACCGCGTTG | TGCCCAGCGC | 10800 |
| CATGTGCGGG | TCGTTTCGGC | GTGAAGTTGG | ACGGCGTAGT | TTCGGGGATT | GTGAACCGTG | 10860 |
| GCTGAGGGTG | TAGATGGGAC | AGGAAAAAGC | GTGTGATCTG | ACCGAGGCGA | AGCATGTGGG | 10920 |
| TGGTGCGATG | CGGTGGATGT | GGCGGGGTGC | GGCGGTTTCC | GACGTGGAGA | TGTGGAGATG | 10980 |
| GGGGTGATCC | GGATGCGTGG | CAAGAGGCCT | CGAGCTTGGG | CTTCTCCCGC | GGATGGACGT | 11040 |
| TCTAACTGTA | CACGGCGGCC | GTGGCCTCCG | AGTAAAAAAA | CCAGGTGCTG | ACGCCAGACA | 11100 |
| GAGACGCCGT | CCTCGGAATC | GTGTGCGCGA | AAGCCTGTGC | CGCGGCAGCG | TACGACGTTC | 11160 |
| CAGTCAGCGA | GGCCGTCGCG | TTGGCGCGCC | AACAGTAAGG | TGACGACAGG | TTGGCGGCCC | 11220 |
| ATGGTTCCGA | AGCGTCCCCA | CATGCACCAG | CAGTCGGCGT | CAAAGTCGCT | TGCGCTGTCG | 11280 |
| GCCCAGTCGC | CACCGCCGCG | GCGGATTTCC | GCGCGGGGGA | CGGGGTAGCC | GAGTGCTGCG | 11340 |
| CCCTCGCCAA | TGTTGTGAAG | TGGATGCGTG | AGTTGATGTT | GATTCTCTGT | GGGAAAATGA | 11400 |
| GCGCTGTCCT | GTGGGTTGGT | GTTGGGGTAT | GCGAGTAGTA | GGGGTTGTGT | TTGATCGTAG | 11460 |
| AGGTGTTGGC | GGGCCTGTGC | GCAAGCAGCG | TAGTCTGCGG | CGTCGAGCTC | CATCTGTGTG | 11520 |
| CGGTGTTCTT | CGTCGGCGTG | TTTGTCCGAG | GTTTGGACAT | GCGGTTGTGT | GTTGCTGTGG | 11580 |
| TGTAAGGGTA | ACGTGTGTTG | GGCGTCTGGG | TGAAGCGGCG | TGGTGTGGGT | GCTGTTTGTG | 11640 |
| TCTGTGGCTG | GCATGATTGT | GCGGCATGTG | TGTGTTGTAG | TGGGTGGAGG | TTAAATAGGT | 11700 |
| GAGGTGGGTT | CCCTGGTCCG | CGCCGCAAAC | TGTCCCCGTC | CCCAACGTAA | CCTCCCCTAC | 11760 |
| GCGGCGCGAA | CAGCCCCGGC | CCCAGCGCAA | CCCCCGTCCC | CGGCCCCAAC | ACCGTCCCGC | 11820 |
| ACACCCCCCG | TCTCCGCAAC | ACCCCGGCAT | CGCCGGCGGC | CAGAACGCTC | GAAAACCCCC | 11880 |
| GACAAGCGCA | GCGCCGAAAC | GACACAGGCA | AGGACCGTGG | AACGCACCGG | CAGCGCGCCG | 11940 |
| AAACACCGTC | CCGAAGCCCG | GTGCCGACAA | CAAATACCGT | GGGACGACAC | GCACCGGCAG | 12000 |
| TGCGCAGGCA | GCGTCGGACA | CAACACGCTT | ACGGCCCTCA | ACACTCCCTC | GAGGACCCAC | 12060 |
| CACGCGGCCC | CGCACCGGCG | GTGTTTTGGG | TGTGTCGGGG | CGCGGCCGGG | TGGGTGTGTG | 12120 |
| CCGGGTGTGT | CGCGGGCGTG | TGTTGGGTGT | GTCGGGGGTG | TGTTGGCAGG | GTGTGTCAGG | 12180 |
| GTGTGTCGCG | GGCGTGTGCC | GGGTGTGTCG | TGCCGGGTGT | GTCGCGGGCG | TGTGGCGGGT | 12240 |
| GTGCCGGCGG | GGTGTGGTGG | CGGGGTGTGT | CGGCGGTGTG | CGCGGCCTCG | GGGTGTGCGG | 12300 |
| CTTCGCAGGA | ACGAGTGTGT | GGCCTCGCGG | CCGTTATTTC | CCCCGCGGTC | CCCAGGGCCG | 12360 |
| TCGTCCCTCG | CCCCCGGGCG | TTGCTTTTCG | TGTGTCCCCA | GGGACCCATG | CTGCCGTCCC | 12420 |
| CCGGGAACTT | CCTCTTTTCC | CCGGGGAATC | ACACAGACAC | AGACACGCGT | CTTCTTTTCG | 12480 |
| CCGTGCGCGC | CGCACGTCGC | TTTTATTCGC | CGTCGCCGTC | CTCCGCACCA | CACGCAACTA | 12540 |
| GTCGCCGTCC | ACACACGCAA | CTCCAAGTTT | CACCCCCCCG | CTAAAAACAC | CCCCCCGCCC | 12600 |
| CTCGAGGACC | CACCACGCGG | CCCGGAATGG | ATGTCGGGCG | TCCACCTAGA | TGGGTGCGCG | 12660 |
| CCCGGGAGGC | GGCTGTGCGC | TCCAGTGGTA | CGCGCCTGCC | GCGCGTCTTC | CTTCGGGTAG | 12720 |
| CTGCCTTTCC | CAGTCCACGG | CCTTCCAGAC | TGCGTGGCGC | CAAGGCGGCG | CCAGCACGCG | 12780 |

-continued

| | | | | | | |
|---|---|---|---|---|---|---|
| CCGTGCACGT | CGCTGCCTAT | AAAAGCCAGC | TGCGTGTCGC | CCGCGGCACA | CGGGCGACGA | 12840 |
| AGGCGTCCGC | GTGTCTAAAC | CGCGTGCTCG | CTGACGCGGG | TTTGCTTCCT | ATATAGTGGA | 12900 |
| CGTCGGAGGT | GTCCGGCGCC | CATGGCCCAG | CGCAACGGCA | TGTCGCCGCG | CCCCCCGCCC | 12960 |
| CTTGGTCGCG | GCCGCGGGGC | CGGAGGGCCT | TCGGGGGTTG | GTTCCTCTCC | TCCTTCTTCT | 13020 |
| TGTGTGCCGA | TGGGAGCGCC | GTCAACAGCG | GGCACTGGTG | CGAGTGCTGC | GGCTACGACG | 13080 |
| ACGCCGGGCC | ACGGCGTCCA | CCGGGTAGAA | CCCCGCGGGC | CGCCGGGCGC | CCCTCCGAGT | 13140 |
| AGCGGCAACA | ATAGCAACTT | TTGGCACGGC | CCGGAGCGCC | TGTTGCTGTC | TCAGATTCCG | 13200 |
| GTGGAGCGCC | AGGCGCTGAC | GGAGCTGGAA | TACCAGGCCA | TGGGCGCCGT | GTGGCGCGCG | 13260 |
| GCGTTTTTGG | CCAACAGCAC | GGGCCGCGCC | ATGCGCAAGT | GGTCGCAGCG | CGACGCGGGC | 13320 |
| ACGCTGCTGC | CGCTCGGACG | GCCGTACGGA | TTCTACGCGC | GGGTGACGCC | GCGCAGCCAG | 13380 |
| ATGAACGGCG | TGGGCGCGAC | GGACCTGCGT | CAACTGTCGC | CGCGGGACGC | GTGGATCGTA | 13440 |
| CTGGTGGCTA | CCGTGGTGCA | CGAGGTGGAC | CCCGCAGCCG | ACCCGACGGT | GGGCGACAAG | 13500 |
| GCCGGCCATC | CCGAGGGTCT | GTGCGCGCAG | GACGGACTGT | ACCTGGCGCT | GGGCGCCGGG | 13560 |
| TTCCGCGTGT | TCGTGTACGA | CCTGGCAAAC | AACACGCTGA | TCCTAGCGGC | GCGCGACGCG | 13620 |
| GACGAGTGGT | TTCGGCACGG | CGCGGGCGAG | GTGGTGCGGC | TGTACCGCTG | CAACCGGCTG | 13680 |
| GGCGTGGGCA | CCCCGCGCGC | GACGCTGCTG | CCTCAGCCGG | CGCTCCGACA | GACGTTGCTG | 13740 |
| CGCGCCGAGG | AGGCGACGGC | GCTCGGACGG | GAGCTGCGCC | GGCGGTGGGC | CGGCACGACG | 13800 |
| GTGGCGCTGC | AGACGCCGGG | CAGGCGACTG | CAGCCGATGG | TACTGCTGGG | CGCGTGGCAG | 13860 |
| GAGCTGGCGC | AGTACGAGCC | GTTCGCGTCG | GCGCCGCACC | CCGCGTCGCT | GCTGACGGCC | 13920 |
| GTGCGTCGGC | ACCTGAACCA | GCGTCTGTGC | TGCGGCTGGC | TGGCGCTGGG | CGCGGTGCTG | 13980 |
| CCCGCGCGGT | GGCTGGGCTG | CGCGGCGGGG | CCGGCGACGG | GGACGGCGGC | GGGGACGACG | 14040 |
| TCGCCGCCAG | CGGCGAGCGG | CACGGAGACG | GAGGCCGCCG | GCGGGGACGC | GCCGTGCGCG | 14100 |
| ATAGCGGGAG | CCGTGGGGTC | CGCTGTACCT | GTGCCTCCGC | AGCCGTACGG | CGCCGCCGGC | 14160 |
| GGGGGCGCGA | TTTGCGTGCC | TAACGCGGAC | GCGCACGCGG | TGGTCGGGGC | GGACGCGGCA | 14220 |
| GCAGCAGCGG | CGCCGACGGT | GATGGTGGGT | TCGACAGCGA | TGGCGGGTCC | GGCGGCGTCG | 14280 |
| GGGACCGTGC | CGCGCGCCAT | GCTGGTGGTG | CTGCTGGACG | AGCTGGGCGC | CGTGTTCGGG | 14340 |
| TACTGCCCGC | TGGACGGGCA | CGTGTACCCG | CTGGCGGCGG | AGCTGTCGCA | CTTTCTGCGC | 14400 |
| GCGGGCGTGC | TGGGCGCGCT | GGCGCTGGGA | CGCGAGTCGG | CGCCCGCCGC | CGAGGCCGCG | 14460 |
| CGGCGGCTGC | TGCCCGAGCT | GGACCGCGAG | CAGTGGGAGC | GGCCGCGCTG | GGACGCGCTG | 14520 |
| CACCTGCACC | CGCGCGCCGC | GCTGTGGGCG | CGCGAGCCGC | ACGGGCAGTG | GGAGTTCATG | 14580 |
| TTTCGCGAAC | AACGCGGTGA | CCCCATAAAT | GATCCCCTCG | CATTTCGTCT | TTCGGACGCT | 14640 |
| CGAACTCTCG | GTCTCGACCT | CACCACCGTC | ATGACAGAGC | GTCAAAGTCA | ATTGCCCGAA | 14700 |
| AAGTATATCG | GTTTCTATCA | GATTAGGAAA | CCTCCTTGGC | TCATGGAACA | ACCTCCACCC | 14760 |
| CCATCTCGCC | AAACCAAACC | GGACGCTGCA | ACGATGCCCC | CACCGCTCAG | TGCTCAGGCA | 14820 |
| AGCGTCAGCT | ACGCGCTCCG | ATACGATGAC | GAGTCCTGGC | GCCCGCTCAG | CACAGTTGAC | 14880 |
| GACCACAAAG | CCTGGTTGGA | TCTCGACGAA | TCACATTGGG | TCCTCGGGGA | CAGCCGACCC | 14940 |
| GACGATATAA | AACAACGCAG | ACTGCTGAAG | GCCACTCAAC | GACGAGGCGC | CGAAATCGAC | 15000 |
| AGACCCATGC | CTGTCGTGCC | TGAAGAATGT | TACGACCAAC | GCTTCACTAC | CGAAGGCCAC | 15060 |
| CAGGTCATCC | CGTTGTGCGC | GTCCGAACCC | GAGGATGACG | ACGAAGATCC | TACCTACGAC | 15120 |
| GAATTGCCGT | CGCGCCCACC | CCAGAAACAT | AAGCCGCCAG | ACAAACCTCC | GCGCTTATGC | 15180 |

-continued

```
AAAACGGGCC CCGGCCCACC TCCGCTGCCG CCAAAGCAAC GGCACGGTTC CACCGACGGA 15240
AAAGTTTCTG CGCCCCGACA GTCGGAGCAT CATAAAAGAC AGACCCGACC GCCAAGGCCG 15300
CCACCGCCCA AATTCGGGGA TAGAACCGCG GCCCATCTCT CGCAAAATAT GCGGGACATG 15360
TACCTCGATA TGTGTACATC TTCGGGCCAC AGGCCACGGC CGCCAGCACC TCCGCGGCCG 15420
AAAAAATGTC AAACACACGC CCCTCACCAC GTTCATCATT GAAAGTCTCT CCAGTCCATA 15480
TGTTGTCAGG ACGTGCTGTC GTTCTCCGCT TGCTGCGAAG CCCGTTCTTC CGAGTCGTGT 15540
CGCTGCGTCC AGCGTCGCGC CCAAGATGGG AATTTGGGTC TTTTCACGCG TAGCCTCCTC 15600
CACCACGGCT GCTGATCGCC GTCACTAAGG ACCGACACGG AGGATGACGA GGAGCTTCTC 15660
CCCGACTCCG CGGTCCGCGA CCGGCTACGT AGCGCGTGTC CCTGCCAGTC TCCGCAGTTA 15720
CACCACACGT CGTGAGCAGC GTGCACCTGC TGCCGCCACT GGGCCTCGGC GTGCTCAGGC 15780
CACCCGCCGG AGCCCGGTCT GAGCTCCGAC GCAGGATGCG CGTACTCAAC GTGCGCCTTC 15840
CAGTCCATAC AGCAACACCA TAGGTCGTGC GAGTCGTCGG CTACCCGCCG CCAGGCCAGT 15900
TCCCGCATGG GAAGGCTGGA CACGCCGACC GAGAGGTCAC CGAGCCCGGA CGCCATCTCT 15960
TCTTCCTCTC CGTCGCTGTC ATTAAGCAGC CAGGTCACCT CCTCCGCTCC GCGTCCGCCG 16020
GTCTCGACGG ACCGCGCCGC CGTCGGCAAC ACGGAAAACA GCACGCCAGC CCGAGCCGCT 16080
AAGGCCGCAT GCCCCTGCCG CCCAACTGAA CACGCATACC CCGCTCAACT GCGTTTTGCC 16140
ACCCCTGTCA GTGCTCTCGC TCGAGCACCA CCCCGCATCT CCCAACCTTT TTCCAATAAA 16200
CGAAACCGAC ATGACACACG TAATGGGTAC TCGTGGCTAG ATTTATTGAA ATAAACCGCG 16260
ATCCCGGGCG TCTCAGCACA CGAAAAACCG CATCCACATC ATAGACAAGT TACAGTCCAC 16320
AGTCACATAC ACGATAAACA ATACCAACAG GGTAATGTTT ATGGAGTAAA ACACTATTGT 16380
CCAGGCCACA TGCGTGTATG ACTTCCGCAC CATCCCGTAC TGCATGTTCC ACATGTACGC 16440
GCTAGACGTG TAATCCACTC GCAGTTCGGG GACGCAACGC AGCCAGATCA CATCCCCTTG 16500
CAGTACCAGA CGCAGGGCTA GCGTCTCGAA GATCGGCATC ACATCTAAGT TCCGCACGTT 16560
CCACTTTAAC GACTCCCCGG GAACGAACTC CACGTCGTCG GCGTGTACGT ACAGGTTCTC 16620
TCCCACGCCG CCATAATCGG CCTTCGGATC GAAGACGAAC CGACTCATGT TGCCCACGAT 16680
GCTCCCCCGA GCAAACAACT TGCCGTTGTC AATGTAGCAC CGGTTGTCCT CGATTTGAAA 16740
CCAGGGATGC TTGGCCGTGG ACTTCCAGGG CCGGAGCGCG TCTTCCCCGG CTTTAGTGAT 16800
TCCATCGGGC AGGCGGATCA AGGGACCCAT GGAGGTCCAA AGACCCACCC AGGCTTTCCA 16860
GAGATTGTTC ATGGTGAAAC AGCGTGTGGA CTGTACGCTC TTTCCCAATT TATATCCCAG 16920
AGTAGTGACG TGAGCCCAGC CACCTCCCAG ATTCCTGACG TTTTGGTTGT CTTTCCTGCC 16980
AATTCCTCCC GTAAACTTAT GATTATCCTA GCCCATTCCC GATAAAAATA CACGGAGACA 17040
GTAGATAGAG TTACGAATAA ACCGGTTTAT TTATTCAAGT GTCTCAGGAG ATTATTGAAC 17100
GAGCGTGGAT ACCACGCCGT CGTCAGTTCA TGGTGGCATT GAGCAGCCAT AGCACCAGAG 17160
TCCCGGCGCC CGGTATCAGA CACGCTGACC TACCGGGCGC CTTCGAGTCC GTACCCCGCG 17220
GCCTGGGTGT TAGAGTCCGT ACCTTGCAGC CCAGGTAGGT TTCAGGTACC AGCTGGTTCG 17280
TACCTGTTAA ATAAATCGCA GACGGGCGCT CACCCCTACG GTCAGGAGCA CAAGAACAAC 17340
CAGAGAGAAC AGATATACGA GCAGGGTTCT GAACAGCAGA CCCCAATTGT CGTCTCTCAT 17400
GCTTCGCTGA AGGTACCAGT TGATGGTCTG AGAGCTATAG TCCATCCTCA CCTGAGGAAC 17460
ACACGCGGCA TATTTCTTGG GGTCTCCCCA CCTCGTAGAC AACGTGATGT CCACCATATC 17520
CACGGTGTGC GTCACCGGGT GCCCACCGAT GTTCCACTCG AAATAGGCTC CGCGCTCATC 17580
```

-continued

| | | | | | | |
|---|---|---|---|---|---|---|
| ATGGTGGTAC | TGCTCACCGG | ACACCTGCAG | TCTGTCCATG | TAAGATTGAG | AGACGATACC | 17640 |
| CACGTTCACA | AAGTGTTTCT | CGGTGAAGTT | GCCCGACATC | CTCCCCTTGA | AGTACAGCAT | 17700 |
| GCCCATATGG | AACCAGCATT | GGTTCTCCTC | CACTCGAAAG | TGGGCCGATC | TGATCTCCGA | 17760 |
| TACCACCACA | TCCAGGGGCC | GGGGCACCGA | GTCCGCGAGT | CTCAGGAACA | AGACGGCCAG | 17820 |
| GATCGCGAGC | ACCAACACCG | GCTTCATGGC | TCCGAAGGTC | CGCTGCTCGG | CTCCGCTCAC | 17880 |
| CGCTCCGGTC | TGGCTGCAGC | AGTGCTTCGC | TGAGAAGTAG | CGTGTGGACT | GAACGGTGTT | 17940 |
| TTTGAATATA | TAGCGTTTCT | TGGTGACGTT | GTTTCCCCTA | CGTAGTAGGC | AACTACGTGC | 18000 |
| CAAAAGAGGC | GTTACGGTAC | TTTCCGTACT | GGGATTTCCA | AACCGGGACT | TTCCACACGG | 18060 |
| CGGTTTCAAC | ACCGGGACTT | TTCACACGGT | GATTTCGGCA | CCGGGACTTT | CCGCACGGCG | 18120 |
| GTTTCGCCAC | CGCTGACGTT | CTCATCGCCG | CCCACGTCAA | CGGTGGCGAC | ACCGTACTTT | 18180 |
| CCCATGCGGT | TTATAAACGT | CAAGAGTCAC | GTCAGTCGCC | CACCCCCATT | ACACGGCGAT | 18240 |
| ATCCCGATAG | GGCATGAGGG | GACCCGGGTG | TCGCGACATG | TCGACGACAG | GTGCGGATTA | 18300 |
| GTGGTCGTGT | CGCGACATGG | ACGTGCAGGG | GGATGTCTGT | CGCGATAGAG | TTGATGTGAC | 18360 |
| AGCCCGCTAC | ACCTCTCTGT | CGCGACATGC | ATACACAACG | GGCCGGCTTG | TCGGCGATTG | 18420 |
| TCGCGACATA | TCGTTATCAG | TTAGCGACCG | GAGTTGTCTA | TCGCGACATA | TCGTCGACTA | 18480 |
| TCGCGACAGA | AAAAATACCG | TTCGTAGAGA | ATGCCGTGTT | GAAGGAACGC | GCTTTTATTG | 18540 |
| AGACGATAAA | ACAGCATCAG | GAGCCACAAC | GTCGAATCCC | ACGTCCAGTC | GATTCGTATG | 18600 |
| TTATGCTGCA | CAGCAATGCT | AGAATAACAA | CCAGCAGGGT | AATCCCGCAA | CATAAATACA | 18660 |
| AAGTCACAGC | GAAGAATCCG | TGTCGTTCTA | TCAAGCGAAA | CGCGTTCCAA | ACGGCCCCGT | 18720 |
| CACAGACGCA | GTTATTCATA | AGCGTTAACA | ACCGGTGGCT | AGGATGAATA | TCCAAATCAC | 18780 |
| AGGGCAGTAG | CCGACGGACT | CGTTGACAGG | TCAGCCTACC | CTCAAGGTTC | CTATCGTTCG | 18840 |
| GACGGGATTT | GTGCGTTTTA | GGCCTCTTTT | TCGCCGCCTG | CAAGCATTGG | TGCGCAAAGT | 18900 |
| CCTCACCCAG | CTGTTTCCAG | CTATCATCTG | CATCTGTGCA | GTCCCCTGTA | TCGTTGTAAC | 18960 |
| AAACGGGTCT | GTGCGACTTC | GTTCTCGGAA | CACA | | | 18994 |

( 2 ) INFORMATION FOR SEQ ID NO:5:

( i ) SEQUENCE CHARACTERISTICS:
( A ) LENGTH: 5020 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

| | | | | | | |
|---|---|---|---|---|---|---|
| AAGCTTGTTG | TCGCGGAGAC | AGAGAGAGAA | GGGTTTTCGG | GTCACGCGAA | GACCGCTCAC | 60 |
| CGGGGGTCGG | CAACGCACAC | ATCAACAGAA | AACCGAGACG | AATCAAGAGA | TCCATAGTGA | 120 |
| AGGAGTGATA | TCGACGTGCT | TACGAAACGG | CGATTATATA | TGTTCTCAAC | AATACCGCCC | 180 |
| TACGTTGTAT | GATGTAACGT | GTGACGTGAG | TCTGATCCAA | CACTGAACGC | TTTCGTCGTG | 240 |
| TTTTTCATGC | AGCTTTTACA | GACCATGACA | AGCCTGACGA | GAGCGTTCAT | CGGGGCATGA | 300 |
| AGTACGCATT | ACACAAACTC | CATATATTTG | TTACGATAGA | ATACGGAACG | GAGGAGGCTT | 360 |
| TCGCCACACC | TATCCTGAAA | GCGTTGCATT | CTTTATGATA | GGTGTGACGA | TGTCTTTACC | 420 |
| ATTCCCACGG | CTGCTTTGCG | TGATGATGAC | ATTCATCATG | TATTTCCATT | CACACATACC | 480 |
| TTTTGTGCAT | ACGGTTTATA | TATGACCATC | CACGCTTATA | ACGAACCTAA | CAGTTTATTA | 540 |
| GCCCTTGACA | GGATAGGTCA | AAAGATTATA | TGTAGGTTTT | CCGGTAAACC | GAATTGTGAT | 600 |

-continued

ATTTCTCTGC AGGAAATAGA ACAGCCTGGT ACCTATAAAA CGGACAATGC AGTACTGTAG 660

CAGCGTAACC AAGTAGGTCC ACATGAACAC GTACAAAATT ATGGTAAGCC ATCGTTTTTC 720

ATACCACAGC CTGTAGCTGT CGTACATGAA TGAGGACGGT CGAGGAACCC AGGGTAGTTG 780

TAATTGGGGG CGACATTCGT ACTGTCCAGA AGACAATTGC ACGGGTTTCA GTGAGATGAG 840

TACTTTAGCG ATGTCGGCGG GGGCGCTACG TTTCACCGTG ACGGTGAGAA CTTGACCGTC 900

GTTTTGTATT TCATGAGGCA CGTTATACAA GCCACTGGTA TCATGAAGGA TGACCTCTGA 960

TGCGATGTGA GGATTAAATT GTCCCTCAAA CCGCCAAACG CTGGTCATGT TTCCACCGTC 1020

AATTACGCAG CTGACGGTGT GAGATACCAC GATGTTGGAC TTAGGTTTGG GGGCTAATTG 1080

CCTTTTTACA AATTCCCTTC TGTATTGCAG GTCCTGCTGC CACTGCTTTT CCGTGCGGAA 1140

AGTCGCCATG TCTTCCACAC GTGTGGCGAC GATAGACGCC ACCAAGGTAG CTACCAGAAG 1200

CAGCTGGATC CGCATGGCAT TACCGTATGT CAATTAGAAA GTTGAGCGGA CACGGTTATC 1260

GTTCCTGGCG GATATAAGTA TATAAACGCG AGTTAGCCTT TCCCGTCCGT TTTGTACACC 1320

CGTTCCCCAC ACAAATGACG AATACGACCT TTTTTTTTAT AAAAATAAAC CACGTGTATT 1380

ATATAAAAAC ATTTACATAG AAAAGAGACA CACGGATCAA CATAAGGACT TTTCACACTT 1440

TTGGGGTACA CAGGCGTGCC ACCGCAGATA GTAAGCGCTG GATACACGGT ACACAGTCCT 1500

GGCCAGCACG TATCCCAACA GCAGCACCAT CGCCATACAG ATGGCGATCA CGACCCCGAG 1560

CTCTAAGTGT CTGTATTCAT AGTGTAGTCG CCGCAGGTTA TCCACTGAAT TCCCGTAACT 1620

GAAATAACGT ATATGGTACC GAGGCTGGCA CCACATGGGT TTGCATTTGG TGCACGGCAC 1680

CAAATGCAGA GTGAGATGGT CCAAGTCCGT GGGCACCCAC TGGCGCAAAC GGAATACGGC 1740

TTCGGTGGTC TCCACGAGGC ACTCCGGGGC GTGCAGACGG CCCCACTTTC GTCCGCGACG 1800

GCCCGACCAG CCGACCCGAG CCACTATCCC TTTCTCGGGA TAGAACGTAC CCTGTACACG 1860

CCACACAGCG TCCAACACGC CGTCCTTGAC GACGCAGCTG GCCTGATAGC TGGACACGTT 1920

GTTAAGCGGC GGAAAGCGAA ACTGACGTGC CGGCGGAGCC ACATAGTTCG GTTCACCGTG 1980

TTGTCGCGGT TCGTCCTCCC TATAGTAATA GTAGTCGTCG TCCTCATAGG GGTTGCCGGC 2040

GTGAGCCAGC GTTACCCAAC AGCAGCCCAG GCCGACGAGG AGGCGCAGCC ACCGCCTCAT 2100

GGCGGCTTCG CCAGTCAATC GTCTTTAGCC TCTTCTTCCC GTGAGGTCCT TCCGGTGGCG 2160

CGGTGCCGAC CTCGGACCCA GGGACGTATC CACCTCAGGT ACACACAGCA GGCTACCTGG 2220

ACACCGAAGC TGAACAAGGC TACGTGTTTC ACAAACTGCA CCAGTACCAC ATAGAGGAAT 2280

GTCAGGTAGC GTCTCTCCGC AAACAGCCGT TCCAAGTCTG AGGGCGTTAC CCGCAGCGGC 2340

AACCAGGGCA GCCTGGACGC CGGCCGGCAA TGGAGCACGC TCCGGTTACA GGCACTGCAG 2400

GGGTAAACGG TTAACATCAC GTAAGAGAGT CGTGCGTCCA CCTGTGGGAG CTCAGTTTCG 2460

TAACGTAGAG CCCCGTCATT TTCCAGCTGG GGTGCGCCGA CCTTGAAATG GGTCGCGCTC 2520

CGCTCGTTAC CCCAGGTGCC GTAGGCTCTC GGGGCCGTAT CGGAGAAGTT GCCACGCACA 2580

AGCCAGGCGG CCACGAGTAC CCCGTGCTGG ACGTAACATT CGGACACGGA ACTGGAGACA 2640

CGGTAGCCGG ACACGTCCCC AAACCCGCGA GGGTACTGGG GCAGACGGAC GGACTTGCTA 2700

TTTGACAACG GACAGATACG AGACGACGAG GACGCAGACG ACTCGTCGCT GGACCACGAC 2760

AACCGGAGCG ACTCCTTGGA GCGGCTCGAG AGTACACTTA CTGCGATCAG ACACCAGTGC 2820

CAGAAGAAGG AACAGGTGGA CGGGGACCAC AGGATCATAG CCGCCGGCAC CGCGGCCGGC 2880

CGCAGGAAGC CGCCCGGCGC GTCGTCTGTG TGCGGGAGCC GAAACACCGT GCCTCTTTAT 2940

ATCGTCCCGA CGTGACGCGA GTATTACGTG TCAGGGGAAA CCCCCGTCAC GACGAACGTG 3000

-continued

```
ATTTGTAAGT GACGCGGGGT GCTGACGGGG TTCGGCCCGA GAGGTGACGG AGCGCCTCAC 3060
GTCAGTATGA TGTCCGATCC GCGTCAGCCC CGACGTGGTT GTGGTCACCG AAACCCACGT 3120
TTATATGGAC GTTGAGAGCA GCGCCTGACC ACATGATTCA TCATACCATT TCTCGGAATC 3180
GGGCCCATGC CGGGAAAGCA CATTCCTTTT CAGTAAACAA CAATGACATC ATAACAAATC 3240
ATTTTATTCG CGAGGTGGAT AATAACCGCA TATCAGGAGG AGGGATCGGG TGATGACGCA 3300
GGCCCCGCAG AACAGTCCGA AATAAATTTT TAGTATTGCC CCATAGTCGC CTAGATACCA 3360
GAGGTACGTT AAGTTCATCA AAACGCCCAT CGGCGTCCCG GAATCGTATA CCGGGCACAC 3420
GAAGCGTTCA TAACAATCCC GGGAGGCGAG TGTTAGGGTA GCAGAGTAGT TTCGGGGTCG 3480
GTTTCCTTCC GGCGACGACA GTTCCGTGGG CAGCAGAATG TACAGCGCCT CGGTAGCTGT 3540
CGCGGTGCCT TCCACGAGGA TGGGCTGCCG GTGCCTTTCG TGATTTTCCC CGTCGTGTAG 3600
CCAAGCCGAG GCCCGCAAAG TCTTAGGCGA GGGGAATTGT CCATAGAGTT TCACCGCACC 3660
CTTCAGTACA TGGTTCTGAA TAACACAGCC GCACGTGAAG TAGGTAGGTT CTCTCGTCTC 3720
CTCCGTGGCT GCCGCCACCA CTCCCAGCCA CCACAACAGG CAGATCGCCA GAGGGTTCCG 3780
GAGGCTTCCC CGGCGTAGCA TGGTTTTGGG TTAAAGCAAA AAGTCTGGTG AGTCGTTTCC 3840
GAGCGACTCG AGATGCACTC CGCTTCAGTC TATATATCAC CACTGGTCCG AAAACATCCA 3900
GGGAAAATGT CGGTGCAGCC AACCTTTCAC ATACAGCCCC CAAAACACTT GAATCACTGC 3960
CACCATCATC AGCGTATACT GCGCCGACTT AATCGTGAGC GCGTAGTACG CCATTAGACG 4020
GCGATCTTCG AACAATAGTC GTTCGATGTC CTCTAACGAG CTCCACAGGG GAACCCAAGG 4080
CACGAGGCAC CGGGGTTCGC ACTCTACATA ATAAGTTTGG CATTGGTGGC AGGGGGAAAA 4140
GTAGAACAAC ACGAGTTTTG TGCGTTGGGG AACACGATAG TCCCGGAGCC AGTAGCGTTT 4200
TGCGACGAGG CTTTCGGAGA CGTCCTCCAC CGGCGTCGGC ACTCGATCCG CGTAGCCCTC 4260
CAGCGTCTGG TAGTACACCC GGGGTGTCGG CGTGGGCACG GACAGGTTCC CGCGCAGGGT 4320
CCACAGAGCC TCCAGTCGAC CGCCCGATCG GAGCACGCAG CGCGCCTCGG AATACTCTAC 4380
TCGGTACTCC GAAACATCGG ACAGAGGCGG TAACGGCTCC GTCTCCACCA AGGGCGGAGG 4440
TTCATCGAAA AGAGTCAAGG ATAATTCAGG CATACTACCC GCGACCGGGG CCCAGAGGGC 4500
TAGAATAAGC ATTACAAGGT TCATTCTGTC TTACAAGGGA AGGCTGTTAC CCTGTCTAGA 4560
CTCAAAAGCT GTAAGGCTGT CTTATAGCAT GTAGTCTTGC ACGTCACGGG GAACAGGGTG 4620
GTGATCTAGT GACGTCGGGA GAACACGGTG TTTTAGGGTG CGGGGGACAA AGGACAGTAC 4680
GACAGATTAG GTGATAGAAA CGTTTTTTTT TATTTATGAA AAAGCCAGTG TGCCGTGCGG 4740
CCTAGGGCCC CGGCGTAGTT TGGATACCAG ATGGGGGCCG TCAGGGGTAC TACCACGAGC 4800
AGAAACATAA TGACTTGGTC CATGTATAGC AGCATAGCGG TGCGCAGCAG GTCGCCGTCC 4860
GTGTAGCAAT TTGACGGTGA GCGATAAAGC ACCGTTAATG TGTCGCGGAT AAGCACGATC 4920
TTGAGGCCGT AGATGAAGCT CACAGTCAGT GCTAAAATGA TGCGTTGGTA TGGTTCCCAG 4980
GACTGCACGG CGATGAAGAG CCAGAGTATG GGAAGCATGA 5020
```

( 2 ) INFORMATION FOR SEQ ID NO:6:

( i ) SEQUENCE CHARACTERISTICS:
( A ) LENGTH: 5924 base pairs
( B ) TYPE: nucleic acid
( C ) STRANDEDNESS: single
( D ) TOPOLOGY: linear ( i i ) MOLECULE TYPE: DNA (genomic)

-continued ( x i ) SEQUENCE DESCRIPTION: SEQ ID NO:6:

TCTAGACTCA AAAGCTGTAA GGCTGTCTTA TAGCATGTAG TCTTGCACGT CACGGGGAAC 60

AGGGTGGTGA TCTAGTGACG TCGGGAGAAC ACGGTGTTTT AGGGTGCGGG GGACAAAGGA 120

CAGTACGACA GATTAGGTGA TAGAAACGTT TTTTTTTATT TATGAAAAAG CCAGTGTGCC 180

GTGCGGCCTA GGGCCCCGGC GTAGTTTGGA TACCAGATGG GGGCCGTCAG GGGTACTACC 240

ACGAGCAGAA ACATAATGAC TTGGTCCATG TATAGCAGCA TAGCGGTGCG CAGCAGGTCG 300

CCGTCCGTGT AGCAATTTGA CGGTGAGCGA TAAAGCACCG TTAATGTGTC GCGGATAAGC 360

ACGATCTTGA GGCCGTAGAT GAAGCTCACA GTCAGTGCTA AAATGATGCG TTGGTATGGT 420

TCCCAGGACT GCACGGCGAT GAAGAGCCAG AGTATGGGAA GCATGAAGCT TAGCAAACAG 480

AGGATGGCTA ACCGTCGTTG CATGTTCCAG GCCATGAGCC AGGCTAGGCC CGTACACCAG 540

ACGCAGAGCA TGGATGACAG GACATAGGCC TGGATTACCA CGGTGCGATC GAAACACAGC 600

CCGATGGTGG ACACGGATAT CGTAGTGAGG GTGGTATATA CCATGACCAG CATCAGGGTC 660

CCGGGTCGGC GCCGACGTTC CAGCCAGTAC GCGTGGCAAC GCAGAGCGCA GGGTAGCAGT 720

GTGCTCCAGA AGGGCAATGT ATCGCGCAGG TAGGGGGCCG TCACGCGCCA CGGTATGAGC 780

ATGAAAAGGA TGGTAGTGGC TATGGTGGCG CTGGTCTGGA ACACGACAGT GCCGTAGAGA 840

CGTACCATCC AGAGAAAGTG TTGAACGCTC CGCAGGGTGT CTTCATCTTT GGTGATTACG 900

GTGACTCGAC GGATCGGCGG TGGTGACGGC GGCGACACGG GTGGGGGTTT CTCTTTCTTA 960

TGGCCGAGTG GCTCGCCTTG GTGAAACTGG ATCTGTACCA TGACGGGTGC TCGACGAACA 1020

GTCGTGGGGG CTTTAGGTAC CCGGCAAGTT TTATAGAGAA AGGGGGACGA TGGGTGGTGG 1080

CTACGAGCCA CCGCCACCTT CGCAATACGA GGATCTGAAG GCGGCAAAGA CGGTCGTCCA 1140

GGGCAGGCGC CAGAGGTTGG GACTGAGCAC GATCAGCGTG ATTTTAAACA TGGTCACCAG 1200

TCCTACGTAG ATCAGCAGCG AGCCGCGTAA CGTCTGAGCA GCCGGCAGTT CGTCGCGGAT 1260

GTAACGCGTG CCGTAGAAAG TCACGGTCAT CATAAGGAAG ACGATGGCGC CGTAGCCGTA 1320

GAGTAGAATA CGCTGATGAT GGAACACGGT CTGGTCGCCG ATAACCCAGA GCGTGATGAA 1380

AAAAACGCTG GTGAGTACCC GTGAGCATAT GAGCTCCCAA CGCTTAGCGC GAAAGCTGTC 1440

CCCAACCATG ACAGCGCCGG TGCAAGCTAT CCACAGCGTG AGGACCAGTG TGTAGTCGAT 1500

GAGGATGGCG GGCAGGTCGG AGCACCAGGT GTAGAAAACC GTGGTAACGG AGAGGAGGCC 1560

TACGTAGCCC ATGGTCAATA CCACGTCGTC GGGGTGCCTT TCGCCCTGTA TCAAGACCAA 1620

ACACCAGAGA AGGGAGGGGG CAAAAACCAG CAGCAGAGGG GAAGATTCAT GTTGACATAT 1680

GTTGTGGGAA TCGGGGATAC CCAGCCAAAT CATTCCGCAG AAAGCCGTAC TGATGGCGAT 1740

GTGAAAGACC ACTAGGGCGT AGACCCGGAC GAGGACAGCA AAACGGCGCA GCCACATAAG 1800

GCCGTGGTGC AGCTGCAGGA GGGAAGCCCA TTGCGGCGAA TGTAGCGACG GTAGCGGCGG 1860

GTCCATGAGG CGGGTGATGC GCCCGAGTGA ACGGGTGAGC GTCTCGGTGG AGTCTTCTTA 1920

TAAACCAGCG GAGCTCAGGC AGCCTTGCTC TGGAACGTCG CAGTGGTGGT GTTGAGGATG 1980

ACGCTGAGCG TGCCGTTGTC AATCAGGTAA TGATGATAGG TGCCGAGCTT GGCCAGGTAG 2040

CTGAACATTT GGTCCCAGCG TGCCGACCAC ACCACGGGCG TGAGCATCAG GAGTGTGGTG 2100

TGATAGATTA GTGTTTCGGT GGCGTAAAGT ATCAGCGAGC TGCGGATGAC GTGGCTCACG 2160

GGCATTTTGG TGGCGATGTA GCGCACGTCT TGGAAAAGGA CGGCCAGGAT GCAGCCCACG 2220

AACACGGTGT AGAGACACAG CAAAGTCTTA TGTAACCAGG TGTAAGTAGA AGCCAGGACG 2280

CTGACCATCA CCGTCAAAAG TGTGGAGGTA AAAAGCGCGT CACGCCACAC GGAGCTGAGA 2340

-continued

```
CGGTGCTCCC AAGCCACGCC GTTGCAGGCC ACGAACAACG TCCACGTTAG GATGAGGCTA 2400
GAAATGCCGA TGGGCGCTGT GGCGCACAGG TTGAGCCCGG CGGTGGTGAA CGAGAGAAGC 2460
GCCACATACA GCGCAAACAC CAGGCCGTTG CTGGGGTGTC TGTGATCGGT GAGCTCCAGC 2520
GCGCCCAGAA CCAATACTGG TGTGCAGCTA AGCAATAGCG GCGAGGGATC GTCGCTGCAC 2580
TTGTAGCCCA GCGAGGGGTA ACCCAGCCAA ACCAGCGCGC TAATGAGTAC GCTGAAAGCG 2640
GTTTCCAGCG TCAGCAATCC GTAGACACGC ATGACAATCG CGGTCCGCCG TAGCCAACAC 2700
ACGGCATCTT CGGAAACTGT GGACGCTGTT TCCGAATACC GGGAGGAGAT CGTGCTTCCC 2760
TCTTCCAAGG ATCGGAAAGT AGCGTCCGTC GTTTCCGCGG ACGCGGCTTC CCTGGTACGC 2820
TCCGTTTCCG ACGACGCGGT TTCCCGCTGC GTGGAAACTG TCTCCATGTC GGGACCGCAG 2880
CGCCCGGCGG CGTATCCGCA AGGTCTCGAA GCTACAGCTT GTCAGAGGAA AAGTAGGTTT 2940
GCAAAAAGGT GCGCAGGGTC ATGATTCTCA GCACCATCAG CAGAGTGAAA ACCAGACTGA 3000
GAAACACCTT GACGGCCGCC AAAAGCGCGC GTTCCAGCGG CGTCTCGTAG CGTACAGCCA 3060
GGGCCGCTTC GTGGAAATGC GAGACGGCTA GACAGGTAAT GAGCACGCTG AAGGACAAGA 3120
CGATCTTAAA GCACCAGGAC CAACCACGCC TCAAGATGAC CACCACGATT GCCGTGAAGG 3180
TCAACGTGAT CAAAGCATGG ACGACCACGA TCTGACGGCG GACGGTACGT TCGGGAGCCA 3240
ACAACGCTAC GCCGGTGCAG CTGAGAAAGG CCAGTAAGGT GAACAACGCG GCCGAGATGA 3300
CCAACGTACC GTCCAGGCAG AGACATATCA CGATCAACGG CGGCACGTGA AGCAGCGTGT 3360
AAAAGAGCAG AACGCCGATA TTGCTGGGAT GCGATGTTTC GTAACAGTGA ATGAAGATCA 3420
CTGACGTGAC GGGTATGACA AAGACGAGGC TGGGCGAGGA CTCCGTGAGA CACAGACGAG 3480
AATGGTGAAA CCACGTCGCG GGCGCCGCGT AGCAGAAGGC GCTCAACAAC GCGGTCAAGC 3540
CGGCCAGCTG CCAACCCACG GCGCCATAGG TGTGCAGCGC CACGCGGCAA CAGTCGACCC 3600
AAGCCAGACT GCGGGTCGCC AGCCGGGTCT CTTGGATCCC GGGGGGCACG TAGATGACCG 3660
TGCCATCGGT GGGTACTTGA AACCCTTTTT CTCTTCTCAT GGTGCGCTGC GTTCTCTGGA 3720
AACGGCTGCT CTGTCCGAAA ACCAGTTCCG AACGAAAATC TAGGGCGAGA GGGTGGACAA 3780
CGGCGTCGAC GACGAAGCAT GGGACAGGTC GTTCGGCGTT AACGTCATCG CGTCGGACGA 3840
CGGTAGTTCT AAGAGACGTA GATCGCTCAG CAGGTCCTGA CAGTTGCGGA TTCGCAAGAT 3900
CAGAAAAAAA AGGGAAATGA ACGTAATAAA GAGCTGTAGC GACGTATGCG CCACATCGCG 3960
TGGCATAAGA ACGTGACGGA CGAAAAGGAC CTGCTGCGAA AAGTGACCGG CGAAGATAAG 4020
GCCCACCGTG CTGTAGAAGC CCAAAAGCAG CCGCAGGGGC CAAGTCCAGG GCCGCGTGAA 4080
GACGATGAGA ACGTTGACCA GAAAGACCAC GACCCAGACG CCGTTGATGA GGGTAAATTG 4140
ATCGGACAGG GTGCAGTTGT CGCGACAGAT GAAGACTACT TCCGCGCAGA GCAAGGTGAT 4200
GACCAACGTG AGCACAAACG ACGTCAACAC CTCGCGGGGC TCCTGGCAGG CACACGTGAC 4260
ACCTAGCGCC GGGATGTGCG CCAGGAGGCC GGCGAGTAAT AGCACCAGCT GTCGGAACGG 4320
ACGACGGCAG CGCGGGTGCC GGTTTCGCTG AGCGAGAACC GGTCGCTCAT AGCGGAAATA 4380
CACGAAGAGC GCGGAGGCCA CAGGCACCAG GAGGAGCACC TCGGGCGCCC AGACAACGTG 4440
ACAAGGAAAG CCCGGACGCG ACTTGAGAGT CGCTGTAGGG AAGACCAGAG AGAAGCTACC 4500
CAAGACGGCC ACCGCCGCGG AGATTTGGAA GAGGAGCAAG CCGGCGATTC GGACGACAAC 4560
CTCGAAGCGA TGCACCCAGC CCAGCACGGC CACCACGGCC GCTTCATCAT AGTCGTCGTT 4620
GTTGCCGCTG TCGAACAGCC GCCGAAACAC GATCTGTCGC TGGGTCGCGG TGGGAAAGCG 4680
CAGACCCATG ACAGCCGGAG GCTATATGAC CGCGCGTCTA AGACGCGAGA TCCGTGGGGG 4740
```

-continued

GACTTTTAGA TGTTTGGGCG GCCCGCGGTT CTAACAGGCT TGATTGGTGG AGACGGCCGG 4800

CGCGGCGGGT GGGGGAAACG ACGAGTTTTT CCGTTACGCC ATGGTTCGCG TGAGGTTTCT 4860

CTGTACCTCC CGCAAAAGGT CACAGCCCGA AATGGAGGCC GCGTTGGTGG CCCCGGTGGC 4920

GCGTGACGAT AACCAGGTCA TCCAAGCGAT GAGTTTGTCT AATGAGTCCT CGGTGGTGAA 4980

GAGGATGAGA ATGAGCAGGT ACAGGTACAC CAGGTTCTCA TAGAGACACA AGGTGAGCAG 5040

GTCAGCCTCG GACCACGCGA TCTCAAACAG GCGCGTGGTG TCAAAGACCG TGACGACCAG 5100

CATGAAGCTG AGCGCCATGG CGTAATAGCC CAAAAAAAGT TTGTGCCCCA ACGGTACGGG 5160

CTGCAGGTAA AGTGCGATCA AGAACGCGAT AACGCCGATC ACAAACAGCG TGACGATGAC 5220

CTGCCATCGA CGGTGATTAT GGCCGGCTAG ACCCGTGACG CAGCTGCAGA GGCTAAAAAG 5280

CACGCAAGCC AAGAGGCCCG AGAAGGTCAC TAGCGTAGAG GAGGAGCAGG CGCTGGCCAC 5340

GATCACCGAA AGCGTCGTGA GCACGCTATA AATGGTGAGC AGGCCAGGGC TCGGTGGCGA 5400

CGTGAACGAT CCTTCATCGC GTTTGCCGTG CAGCAGGGCC AAACAGATGG TGGGCACCAT 5460

CAAACTTAAG GGCGGCATAA AGCCGGTGCA ACAGAGAAAG ACGGTGCCTT TAAGATGCGG 5520

AAAAGCCAGC ACCAGGCCCA GACAGAGCAA GAAGGTGCAG GTGCCCTGCA CGGCCACGGT 5580

GCTGTAGACC CGCATACAAA GTAAAAAGCG ACGTACGTCG TTCGTCGACA CGGAGGAAAT 5640

CATAATGACT CCGCGCGAGG GTCGCGGGGG TGGGGGCGCC CAGGCCGTCC CGGTGGCCTC 5700

TGAGTTCGGA GACATGACGG CGGTGGCGAT CAAAAGGCGC GTATGAGAAA CCGTTTATAG 5760

AGTGTAATAG AATCACCGTC ATTCCCACAC GGCGTTCCCC CATAAAGTCA CGTAACACTC 5820

GAGTAAGCGT GAAAAAGCTT TATTGTTGAA TAAAAAACAC GAGTACAACA CCGAGTTGCG 5880

GTGTCCTGTC TGTCTACTGG GTGGGGAAGG TTCATCGTCT GTCT 5924

( 2 ) INFORMATION FOR SEQ ID NO:7:

( i ) SEQUENCE CHARACTERISTICS:
( A ) LENGTH: 1707 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

AGCAGTGCTT CGCTGAGAAG TAGCGTGTGG ACTGAACGGT GTTTTTGAAT ATATAGCGTT 60

TCTTGGTGAC GTTGTTTCCC CTACGTAGTA GGCAACTACG TGCCAAAAGA GGCGTTACGG 120

TACTTTCCGT ACTGGGATTT CCAAACCGGG ACTTTCCACA CGGCGGTTTC AACACCGGGA 180

CTTTTCACAC GGTGATTTCG GCACCGGGAC TTTCCGCACG GCGGTTTCGC CACCGCTGAC 240

GTTCTCATCG CCGCCCACGT CAACGGTGGC GACACCGTAC TTTCCCATGC GGTTTATAAA 300

CGTCAAGAGT CACGTCAGTC GCCCACCCCC ATTACACGGC GATATCCCGA TAGGGCATGA 360

GGGGACCCGG GTGTCGCGAC ATGTCGACGA CAGGTGCGGA TTAGTGGTCG TGTCGCGACA 420

TGGACGTGCA GGGGGATGTC TGTCGCGATA GAGTTGATGT GACAGCCCGC TACACCTCTC 480

TGTCGCGACA TGCATACACA ACGGGCCGGC TTGTCGGCGA TTGTCGCGAC ATATCGTTAT 540

CAGTTAGCGA CCGGAGTTGT CTATCGCGAC ATATCGTCGA CTATCGCGAC AGAAAAAATA 600

CCGTTCGTAG AGAATGCCGT GTTGAAGGAA CGCGCTTTTA TTGAGACGAT AAAACAGCAT 660

CAGGAGCCAC AACGTCGAAT CCCACGTCCA GTCGATTCGT ATGTTATGCT GCACAGCAAT 720

GCTAGAATAA CAACCAGCAG GGTAATCCCG CAACATAAAT ACAAAGTCAC AGCGAAGAAT 780

CCGTGTCGTT CTATCAAGCG AAACGCGTTC CAAACGGCCC CGTCACAGAC GCAGTTATTC 840

-continued

ATAAGCGTTA ACAACCGGTG GCTAGGATGA ATATCCAAAT CACAGGGCAG TAGCCGACGG 900

ACTCGTTGAC AGGTCAGCCT ACCCTCAAGG TTCCTATCGT TCGGACGGGA TTTGTGCGTT 960

TTAGGCCTCT TTTTCGCCGC CTGCAAGCAT TGGTGCGCAA AGTCCTCACC CAGCTGTTTC 1020

CAGCTATCAT CTGCATCTGT GCAGTCCCCT GTATCGTTGT AACAAACGGG TCTGTGCGAC 1080

TTCGTTCTCG GAACACAAGC TTGTTGTCGC GGAGACAGAG AGAGAAGGGT TTTCGGGTCA 1140

CGCGAAGACC GCTCACCGGG GGTCGGCAAC GCACACATCA ACAGAAAACC GAGACGAATC 1200

AAGAGATCCA TAGTGAAGGA GTGATATCGA CGTGCTTACG AAACGGCGAT TATATATGTT 1260

CTCAACAATA CCGCCCTACG TTGTATGATG TAACGTGTGA CGTGAGTCTG ATCCAACACT 1320

GAACGCTTTC GTCGTGTTTT TCATGCAGCT TTTACAGACC ATGACAAGCC TGACGAGAGC 1380

GTTCATCGGG GCATGAAGTA CGCATTACAC AAACTCCATA TATTTGTTAC GATAGAATAC 1440

GGAACGGAGG AGGCTTTCGC CACACCTATC CTGAAAGCGT TGCATTCTTT ATGATAGGTG 1500

TGACGATGTC TTTACCATTC CCACGGCTGC TTTGCGTGAT GATGACATTC ATCATGTATT 1560

TCCATTCACA CATACCTTTT GTGCATACGG TTTATATATG ACCATCCACG CTTATAACGA 1620

ACCTAACAGT TTATTAGCCC TTGACAGGAT AGGTCAAAAG ATTATATGTA GGTTTTCCGG 1680

TAAACCGAAT TGTGATATTT CTCTGCA 1707

( 2 ) INFORMATION FOR SEQ ID NO:8:

( i ) SEQUENCE CHARACTERISTICS:
( A ) LENGTH: 1817 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

TCTAGACTCA AAAGCTGTAA GGCTGTCTTA TAGCATGTAG TCTTGCACGT CACGGGGAAC 60

AGGGTGGTGA TCTAGTGACG TCGGGAGAAC ACGGTGTTTT AGGGTGCGGG GGACAAAGGA 120

CAGTACGACA GATTAGGTGA TAGAAACGTT TTTTTTTATT TATGAAAAAG CCAGTGTGCC 180

GTGCGGCCTA GGGCCCCGGC GTAGTTTGGA TACCAGATGG GGGCCGTCAG GGGTACTACC 240

ACGAGCAGAA ACATAATGAC TTGGTCCATG TATAGCAGCA TAGCGGTGCG CAGCAGGTCG 300

CCGTCCGTGT AGCAATTTGA CGGTGAGCGA TAAAGCACCG TTAATGTGTC GCGGATAAGC 360

ACGATCTTGA GGCCGTAGAT GAAGCTCACA GTCAGTGCTA AAATGATGCG TTGGTATGGT 420

TCCCAGGACT GCACGGCGAT GAAGAGCCAG AGTATGGGAA GCATGAAGCT TAGCAAACAG 480

AGGATGGCTA ACCGTCGTTG CATGTTCCAG GCCATGAGCC AGGCTAGGCC CGTACACCAG 540

ACGCAGAGCA TGGATGACAG GACATAGGCC TGGATTACCA CGGTGCGATC GAAACACAGC 600

CCGATGGTGG ACACGGATAT CGTAGTGAGG GTGGTATATA CCATGACCAG CATCAGGGTC 660

CCGGGTCGGC GCCGACGTTC CAGCCAGTAC GCGTGGCAAC GCAGAGCGCA GGGTAGCAGT 720

GTGCTCCAGA AGGGCAATGT ATCGCGCAGG TAGGGGGCCG TCACGCGCCA CGGTATGAGC 780

ATGAAAAGGA TGGTAGTGGC TATGGTGGCG CTGGTCTGGA ACACGACAGT GCCGTAGAGA 840

CGTACCATCC AGAGAAAGTG TTGAACGCTC CGCAGGGTGT CTTCATCTTT GGTGATTACG 900

GTGACTCGAC GGATCGGCGG TGGTGACGGC GGCGACACGG GTGGGGGTTT CTCTTTCTTA 960

TGGCCGAGTG GCTCGCCTTG GTGAAACTGG ATCTGTACCA TGACGGGTGC TCGACGAACA 1020

GTCGTGGGGG CTTTAGGTAC CCGGCAAGTT TTATAGAGAA AGGGGGACGA TGGGTGGTGG 1080

-continued

CTACGAGCCA CCGCCACCTT CGCAATACGA GGATCTGAAG GCGGCAAAGA CGGTCGTCCA 1140

GGGCAGGCGC CAGAGGTTGG GACTGAGCAC GATCAGCGTG ATTTTAAACA TGGTCACCAG 1200

TCCTACGTAG ATCAGCAGCG AGCCGCGTAA CGTCTGAGCA GCCGGCAGTT CGTCGCGGAT 1260

GTAACGCGTG CCGTAGAAAG TCACGGTCAT CATAAGGAAG ACGATGGCGC CGTAGCCGTA 1320

GAGTAGAATA CGCTGATGAT GGAACACGGT CTGGTCGCCG ATAACCCAGA GCGTGATGAA 1380

AAAAACGCTG GTGAGTACCC GTGAGCATAT GAGCTCCCAA CGCTTAGCGC GAAAGCTGTC 1440

CCCAACCATG ACAGCGCCGG TGCAAGCTAT CCACAGCGTG AGGACCAGTG TGTAGTCGAT 1500

GAGGATGGCG GGCAGGTCGG AGCACCAGGT GTAGAAAACC GTGGTAACGG AGAGGAGGCC 1560

TACGTAGCCC ATGGTCAATA CCACGTCGTC GGGGTGCCTT TCGCCCTGTA TCAAGACCAA 1620

ACACCAGAGA AGGGAGGGGG CAAAAACCAG CAGCAGAGGG GAAGATTCAT GTTGACATAT 1680

GTTGTGGGAA TCGGGGATAC CCAGCCAAAT CATTCCGCAG AAAGCCGTAC TGATGGCGAT 1740

GTGAAAGACC ACTAGGGCGT AGACCCGGAC GAGGACAGCA AAACGGCGCA GCCACATAAG 1800

GCCGTGGTGC AGCTGCA 1817

( 2 ) INFORMATION FOR SEQ ID NO:9:

( i ) SEQUENCE CHARACTERISTICS:
( A ) LENGTH: 1702 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

CCATGGTTCC GAAGCGTCCC CACATGCACC AGCAGTCGGC GTCAAAGTCG CTTGCGCTGT 60

CGGCCCAGTC GCCACCGCCG CGGCGGATTT CCGCGCGGGG GACGGGGTAG CCGAGTGCTG 120

CGCCCTCGCC AATGTTGTGA AGTGGATGCG TGAGTTGATG TTGATTCTCT GTGGGAAAAT 180

GAGCGCTGTC CTGTGGGTTG GTGTTGGGGT ATGCGAGTAG TAGGGGTTGT GTTTGATCGT 240

AGAGGTGTTG GCGGGCCTGT GCGCAAGCAG CGTAGTCTGC GGCGTCGAGC TCCATCTGTG 300

TGCGGTGTTC TTCGTCGGCG TGTTTGTCCG AGGTTTGGAC ATGCGGTTGT GTGTTGCTGT 360

GGTGTAAGGG TAACGTGTGT TGGGCGTCTG GGTGAAGCGG CGTGGTGTGG GTGCTGTTTG 420

TGTCTGTGGC TGGCATGATT GTGCGGCATG TGTGTGTTGT AGTGGGTGGA GGTTAAATAG 480

GTGAGGTGGG TTCCCTGGTC CGCGCCGCAA ACTGTCCCCG TCCCCAACGT AACCTCCCCT 540

ACGCGGCGCG AACAGCCCCG GCCCCAGCGC AACCCCCGTC CCCGGCCCCA ACACCGTCCC 600

GCACACCCCC CGTCTCCGCA ACACCCCGGC ATCGCCGGCG GCCAGAACGC TCGAAAACCC 660

CCGACAAGCG CAGCGCCGAA ACGACACAGG CAAGGACCGT GGAACGCACC GGCAGCGCGC 720

CGAAACACCG TCCCGAAGCC CGGTGCCGAC AACAAATACC GTGGGACGAC ACGCACCGGC 780

AGTGCGCAGG CAGCGTCGGA CACAACACGC TTACGGCCCT CAACACTCCC TCGAGGACCC 840

ACCACGCGGC CCCGCACCGG CGGTGTTTTG GGTGTGTCGG GGCGCGGCCG GGTGGGTGTG 900

TGCCGGGTGT GTCGCGGGCG TGTGTTGGGT GTGTCGGGGG TGTGTTGGCA GGGTGTGTCA 960

GGGTGTGTCG CGGGCGTGTG CCGGGTGTGT CGTGCCGGGT GTGTCGCGGG CGTGTGGCGG 1020

GTGTGCCGGC GGGGTGTGGT GGCGGGGTGT GTCGGCGGTG TGCGCGGCCT CGGGGTGTGC 1080

GGCTTCGCAG GAACGAGTGT GTGGCCTCGC GGCCGTTATT TCCCCCGCGG TCCCCAGGGC 1140

CGTCGTCCCT CGCCCCCGGG CGTTGCTTTT CGTGTGTCCC CAGGGACCCA TGCTGCCGTC 1200

CCCCGGGAAC TTCCTCTTTT CCCCGGGGAA TCACACAGAC ACAGACACGC GTCTTCTTTT 1260

-continued

CGCCGTGCGC GCCGCACGTC GCTTTTATTC GCCGTCGCCG TCCTCCGCAC CACACGCAAC 1320

TAGTCGCCGT CCACACACGC AACTCCAAGT TTCACCCCCC CGCTAAAAAC ACCCCCCCGC 1380

CCCTCGAGGA CCCACCACGC GGCCCGGAAT GGATGTCGGG CGTCCACCTA GATGGGTGCG 1440

CGCCCGGGAG GCGGCTGTGC GCTCCAGTGG TACGCGCCTG CCGCGCGTCT TCCTTCGGGT 1500

AGCTGCCTTT CCCAGTCCAC GGCCTTCCAG ACTGCGTGGC GCCAAGGCGG CGCCAGCACG 1560

CGCCGTGCAC GTCGCTGCCT ATAAAAGCCA GCTGCGTGTC GCCCGCGGCA CACGGGCGAC 1620

GAAGGCGTCC GCGTGTCTAA ACCGCGTGCT CGCTGACGCG GGTTTGCTTC CTATATAGTG 1680

GACGTCGGAG GTGTCCGGCG CC 1702

( 2 ) INFORMATION FOR SEQ ID NO:10:

( i ) SEQUENCE CHARACTERISTICS:
( A ) LENGTH: 256 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

CCATGCCGGG AAAGCACATT CCTTTTCAGT AAACAACAAT GACATCATAA CAAATCATTT 60

TATTCGCGAG GTGGATAATA ACCGCATATC AGGAGGAGGG ATCGGGTGAT GACGCAGGCC 120

CCGCAGAACA GTCCGAAATA AATTTTTAGT ATTGCCCCAT AGTCGCCTAG ATACCAGAGG 180

TACGTTAAGT TCATCAAAAC GCCCATCGGC GTCCCGGAAT CGTATACCGG GCACACGAAG 240

CGTTCATAAC AATCCC 256

( 2 ) INFORMATION FOR SEQ ID NO:11:

( i ) SEQUENCE CHARACTERISTICS:
( A ) LENGTH: 1328 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

CCCGGCCCAC CTCCGCTGCC GCCAAAGCAA CGGCACGGTT CCACCGACGG AAAAGTTTCT 60

GCGCCCCGAC AGTCGGAGCA TCATAAAAGA CAGACCCGAC CGCCAAGGCC GCCACCGCCC 120

AAATTCGGGG ATAGAACCGC GGCCCATCTC TCGCAAAATA TGCGGGACAT GTACCTCGAT 180

ATGTGTACAT CTTCGGGCCA CAGGCCACGG CCGCCAGCAC CTCCGCGGCC GAAAAAATGT 240

CAAACACACG CCCCTCACCA CGTTCATCAT TGAAAGTCTC TCCAGTCCAT ATGTTGTCAG 300

GACGTGCTGT CGTTCTCCGC TTGCTGCGAA GCCCGTTCTT CCGAGTCGTG TCGCTGCGTC 360

CAGCGTCGCG CCCAAGATGG GAATTTGGGT CTTTTCACGC GTAGCCTCCT CCACCACGGC 420

TGCTGATCGC CGTCACTAAG GACCGACACG GAGGATGACG AGGAGCTTCT CCCCGACTCC 480

GCGGTCCGCG ACCGGCTACG TAGCGCGTGT CCCTGCCAGT CTCCGCAGTT ACACCACACG 540

TCGTGAGCAG CGTGCACCTG CTGCCGCCAC TGGGCCTCGG CGTGCTCAGG CCACCCGCCG 600

GAGCCCGGTC TGAGCTCCGA CGCAGGATGC GCGTACTCAA CGTGCGCCTT CCAGTCCATA 660

CAGCAACACC ATAGGTCGTG CGAGTCGTCG GCTACCCGCC GCCAGGCCAG TTCCCGCATG 720

GGAAGGCTGG ACACGCCGAC CGAGAGGTCA CCGAGCCCGG ACGCCATCTC TTCTTCCTCT 780

CCGTCGCTGT CATTAAGCAG CCAGGTCACC TCCTCCGCTC CGCGTCCGCC GGTCTCGACG 840

GACCGCGCCG CCGTCGGCAA CACGGAAAAC AGCACGCCAG CCCGAGCCGC TAAGGCCGCA 900

TGCCCCTGCC GCCCAACTGA ACACGCATAC CCCGCTCAAC TGCGTTTTGC CACCCCTGTC 960

AGTGCTCTCG CTCGAGCACC ACCCCGCATC TCCCAACCTT TTTCCAATAA ACGAAACCGA 1020

CATGACACAC GTAATGGGTA CTCGTGGCTA GATTTATTGA AATAAACCGC GATCCCGGGC 1080

GTCTCAGCAC ACGAAAAACC GCATCCACAT CATAGACAAG TTACAGTCCA CAGTCACATA 1140

CACGATAAAC AATACCAACA GGGTAATGTT TATGGAGTAA AACACTATTG TCCAGGCCAC 1200

ATGCGTGTAT GACTTCCGCA CCATCCCGTA CTGCATGTTC CACATGTACG CGCTAGACGT 1260

GTAATCCACT CGCAGTTCGG GGACGCAACG CAGCCAGATC ACATCCCCTT GCAGTACCAG 1320

ACGCAGGG 1328

( 2 ) INFORMATION FOR SEQ ID NO:12:

( i ) SEQUENCE CHARACTERISTICS:
( A ) LENGTH: 1528 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

CGGCCTGGGT GTTAGAGTCC GTACCTTGCA GCCCAGGTAG GTTTCAGGTA CCAGCTGGTT 60

CGTACCTGTT AAATAAATCG CAGACGGGCG CTCACCCCTA CGGTCAGGAG CACAAGAACA 120

ACCAGAGAGA ACAGATATAC GAGCAGGGTT CTGAACAGCA GACCCCAATT GTCGTCTCTC 180

ATGCTTCGCT GAAGGTACCA GTTGATGGTC TGAGAGCTAT AGTCCATCCT CACCTGAGGA 240

ACACACGCGG CATATTTCTT GGGGTCTCCC CACCTCGTAG ACAACGTGAT GTCCACCATA 300

TCCACGGTGT GCGTCACCGG GTGCCCACCG ATGTTCCACT CGAAATAGGC TCCGCGCTCA 360

TCATGGTGGT ACTGCTCACC GGACACCTGC AGTCTGTCCA TGTAAGATTG AGAGACGATA 420

CCCACGTTCA CAAAGTGTTT CTCGGTGAAG TTGCCCGACA TCCTCCCCTT GAAGTACAGC 480

ATGCCCATAT GGAACCAGCA TTGGTTCTCC TCCACTCGAA AGTGGGCCGA TCTGATCTCC 540

GATACCACCA CATCCAGGGG CCGGGGCACC GAGTCCGCGA GTCTCAGGAA CAAGACGGCC 600

AGGATCGCGA GCACCAACAC CGGCTTCATG GCTCCGAAGG TCCGCTGCTC GGCTCCGCTC 660

ACCGCTCCGG TCTGGCTGCA GCAGTGCTTC GCTGAGAAGT AGCGTGTGGA CTGAACGGTG 720

TTTTTGAATA TATAGCGTTT CTTGGTGACG TTGTTTCCCC TACGTAGTAG GCAACTACGT 780

GCCAAAAGAG GCGTTACGGT ACTTTCCGTA CTGGGATTTC CAAACCGGGA CTTTCCACAC 840

GGCGGTTTCA ACACCGGGAC TTTTCACACG GTGATTTCGG CACCGGGACT TTCCGCACGG 900

CGGTTTCGCC ACCGCTGACG TTCTCATCGC CGCCCACGTC AACGGTGGCG ACACCGTACT 960

TTCCCATGCG GTTTATAAAC GTCAAGAGTC ACGTCAGTCG CCCACCCCCA TTACACGGCG 1020

ATATCCCGAT AGGGCATGAG GGGACCCGGG TGTCGCGACA TGTCGACGAC AGGTGCGGAT 1080

TAGTGGTCGT GTCGCGACAT GGACGTGCAG GGGGATGTCT GTCGCGATAG AGTTGATGTG 1140

ACAGCCCGCT ACACCTCTCT GTCGCGACAT GCATACACAA CGGGCCGGCT TGTCGGCGAT 1200

TGTCGCGACA TATCGTTATC AGTTAGCGAC CGGAGTTGTC TATCGCGACA TATCGTCGAC 1260

TATCGCGACA GAAAAAATAC CGTTCGTAGA GAATGCCGTG TTGAAGGAAC GCGCTTTTAT 1320

TGAGACGATA AAACAGCATC AGGAGCCACA ACGTCGAATC CCACGTCCAG TCGATTCGTA 1380

TGTTATGCTG CACAGCAATG CTAGAATAAC AACCAGCAGG GTAATCCCGC AACATAAATA 1440

-continued

```
CAAAGTCACA GCGAAGAATC CGTGTCGTTC TATCAAGCGA AACGCGTTCC AAACGGCCCC 1500
GTCACAGACG CAGTTATTCA TAAGCGTT 1528
```

(2) INFORMATION FOR SEQ ID NO:13:

(i) SEQUENCE CHARACTERISTICS:
(A) LENGTH: 1151 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

```
CCATGCCGGG AAAGCACATT CCTTTTCAGT AAACAACAAT GACATCATAA CAAATCATTT 60
TATTCGCGAG GTGGATAATA ACCGCATATC AGGAGGAGGG ATCGGGTGAT GACGCAGGCC 120
CCGCAGAACA GTCCGAAATA AATTTTTAGT ATTGCCCCAT AGTCGCCTAG ATACCAGAGG 180
TACGTTAAGT TCATCAAAAC GCCCATCGGC GTCCCGGAAT CGTATACCGG GCACACGAAG 240
CGTTCATAAC AATCCCGGGA GGCGAGTGTT AGGGTAGCAG AGTAGTTTCG GGGTCGGTTT 300
CCTTCCGGCG ACGACAGTTC CGTGGGCAGC AGAATGTACA GCGCCTCGGT AGCTGTCGCG 360
GTGCCTTCCA CGAGGATGGG CTGCCGGTGC CTTTCGTGAT TTTCCCCGTC GTGTAGCCAA 420
GCCGAGGCCC GCAAAGTCTT AGGCGAGGGG AATTGTCCAT AGAGTTTCAC CGCACCCTTC 480
AGTACATGGT TCTGAATAAC ACAGCCGCAC GTGAAGTAGG TAGGTTCTCT CGTCTCCTCC 540
GTGGCTGCCG CCACCACTCC CAGCCACCAC AACAGGCAGA TCGCCAGAGG GTTCCGGAGG 600
CTTCCCCGGC GTAGCATGGT TTTGGGTTAA AGCAAAAAGT CTGGTGAGTC GTTTCCGAGC 660
GACTCGAGAT GCACTCCGCT TCAGTCTATA TATCACCACT GGTCCGAAAA CATCCAGGGA 720
AAATGTCGGT GCAGCCAACC TTTCACATAC AGCCCCCAAA ACACTTGAAT CACTGCCACC 780
ATCATCAGCG TATACTGCGC CGACTTAATC GTGAGCGCGT AGTACGCCAT TAGACGGCGA 840
TCTTCGAACA ATAGTCGTTC GATGTCCTCT AACGAGCTCC ACAGGGGAAC CCAAGGCACG 900
AGGCACCGGG GTTCGCACTC TACATAATAA GTTTGGCATT GGTGGCAGGG GGAAAAGTAG 960
AACAACACGA GTTTTGTGCG TTGGGGAACA CGATAGTCCC GGAGCCAGTA GCGTTTTGCG 1020
ACGAGGCTTT CGGAGACGTC CTCCACCGGC GTCGGCACTC GATCCGCGTA GCCCTCCAGC 1080
GTCTGGTAGT ACACCCGGGG TGTCGGCGTG GGCACGGACA GGTTCCCGCG CAGGGTCCAC 1140
AGAGCCTCCA G 1151
```

(2) INFORMATION FOR SEQ ID NO:14:

(i) SEQUENCE CHARACTERISTICS:
(A) LENGTH: 1809 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

```
GCATTCTTTA TGATAGGTGT GACGATGTCT TTACCATTCC CACGGCTGCT TTGCGTGATG 60
ATGACATTCA TCATGTATTT CCATTCACAC ATACCTTTTG TGCATACGGT TTATATATGA 120
CCATCCACGC TTATAACGAA CCTAACAGTT TATTAGCCCT TGACAGGATA GGTCAAAAGA 180
TTATATGTAG GTTTTCCGGT AAACCGAATT GTGATATTTC TCTGCAGGAA ATAGAACAGC 240
CTGGTACCTA TAAAACGGAC AATGCAGTAC TGTAGCAGCG TAACCAAGTA GGTCCACATG 300
```

-continued

```
AACACGTACA AAATTATGGT AAGCCATCGT TTTTCATACC ACAGCCTGTA GCTGTCGTAC    360
ATGAATGAGG ACGGTCGAGG AACCCAGGGT AGTTGTAATT GGGGGCGACA TTCGTACTGT    420
CCAGAAGACA ATTGCACGGG TTTCAGTGAG ATGAGTACTT TAGCGATGTC GGCGGGGGCG    480
CTACGTTTCA CCGTGACGGT GAGAACTTGA CCGTCGTTTT GTATTTCATG AGGCACGTTA    540
TACAAGCCAC TGGTATCATG AAGGATGACC TCTGATGCGA TGTGAGGATT AAATTGTCCC    600
TCAAACCGCC AAACGCTGGT CATGTTTCCA CCGTCAATTA CGCAGCTGAC GGTGTGAGAT    660
ACCACGATGT TGGACTTAGG TTTGGGGGCT AATTGCCTTT TTACAAATTC CCTTCTGTAT    720
TGCAGGTCCT GCTGCCACTG CTTTTCCGTG CGGAAAGTCG CCATGTCTTC CACACGTGTG    780
GCGACGATAG ACGCCACCAA GGTAGCTACC AGAAGCAGCT GGATCCGCAT GGCATTACCG    840
TATGTCAATT AGAAAGTTGA GCGGACACGG TTATCGTTCC TGGCGGATAT AAGTATATAA    900
ACGCGAGTTA GCCTTTCCCG TCCGTTTTGT ACACCCGTTC CCCACACAAA TGACGAATAC    960
GACCTTTTTT TTTATAAAAA TAAACCACGT GTATTATATA AAAACATTTA CATAGAAAAG   1020
AGACACACGG ATCAACATAA GGACTTTTCA CACTTTTGGG GTACACAGGC GTGCCACCGC   1080
AGATAGTAAG CGCTGGATAC ACGGTACACA GTCCTGGCCA GCACGTATCC CAACAGCAGC   1140
ACCATCGCCA TACAGATGGC GATCACGACC CCGAGCTCTA AGTGTCTGTA TTCATAGTGT   1200
AGTCGCCGCA GGTTATCCAC TGAATTCCCG TAACTGAAAT AACGTATATG GTACCGAGGC   1260
TGGCACCACA TGGGTTTGCA TTTGGTGCAC GGCACCAAAT GCAGAGTGAG ATGGTCCAAG   1320
TCCGTGGGCA CCCACTGGCG CAAACGGAAT ACGGCTTCGG TGGTCTCCAC GAGGCACTCC   1380
GGGGCGTGCA GACGGCCCCA CTTTCGTCCG CGACGGCCCG ACCAGCCGAC CCGAGCCACT   1440
ATCCCTTTCT CGGGATAGAA CGTACCCTGT ACACGCCACA CAGCGTCCAA CACGCCGTCC   1500
TTGACGACGC AGCTGGCCTG ATAGCTGGAC ACGTTGTTAA GCGGCGGAAA GCGAAACTGA   1560
CGTGCCGGCG GAGCCACATA GTTCGGTTCA CCGTGTTGTC GCGGTTCGTC CTCCCTATAG   1620
TAATAGTAGT CGTCGTCCTC ATAGGGGTTG CCGGCGTGAG CCAGCGTTAC CCAACAGCAG   1680
CCCAGGCCGA CGAGGAGGCG CAGCCACCGC CTCATGGCGG CTTCGCCAGT CAATCGTCTT   1740
TAGCCTCTTC TTCCCGTGAG GTCCTTCCGG TGGCGCGGTG CCGACCTCGG ACCCAGGGAC   1800
GTATCCACC                                                           1809
```

( 2 ) INFORMATION FOR SEQ ID NO:15:

( i ) SEQUENCE CHARACTERISTICS:
( A ) LENGTH: 1765 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

```
TCGCCGCCAG CGGCGAGCGG CACGGAGACG GAGGCCGCCG GCGGGGACGC GCCGTGCGCG     60
ATAGCGGGAG CCGTGGGGTC CGCTGTACCT GTGCCTCCGC AGCCGTACGG CGCCGCCGGC    120
GGGGGCGCGA TTTGCGTGCC TAACGCGGAC GCGCACGCGG TGGTCGGGGC GGACGCGGCA    180
GCAGCAGCGG CGCCGACGGT GATGGTGGGT TCGACAGCGA TGGCGGGTCC GGCGGCGTCG    240
GGGACCGTGC CGCGCGCCAT GCTGGTGGTG CTGCTGGACG AGCTGGGCGC CGTGTTCGGG    300
TACTGCCCGC TGGACGGGCA CGTGTACCCG CTGGCGGCGG AGCTGTCGCA CTTTCTGCGC    360
GCGGGCGTGC TGGGCGCGCT GGCGCTGGGA CGCGAGTCGG CGCCCGCCGC CGAGGCCGCG    420
CGGCGGCTGC TGCCCGAGCT GGACCGCGAG CAGTGGGAGC GGCCGCGCTG GGACGCGCTG    480
```

-continued

CACCTGCACC CGCGCGCCGC GCTGTGGGCG CGCGAGCCGC ACGGGCAGTG GGAGTTCATG 540

TTTCGCGAAC AACGCGGTGA CCCCATAAAT GATCCCCTCG CATTTCGTCT TTCGGACGCT 600

CGAACTCTCG GTCTCGACCT CACCACCGTC ATGACAGAGC GTCAAAGTCA ATTGCCCGAA 660

AAGTATATCG GTTTCTATCA GATTAGGAAA CCTCCTTGGC TCATGGAACA ACCTCCACCC 720

CCATCTCGCC AAACCAAACC GGACGCTGCA ACGATGCCCC CACCGCTCAG TGCTCAGGCA 780

AGCGTCAGCT ACGCGCTCCG ATACGATGAC GAGTCCTGGC GCCCGCTCAG CACAGTTGAC 840

GACCACAAAG CCTGGTTGGA TCTCGACGAA TCACATTGGG TCCTCGGGGA CAGCCGACCC 900

GACGATATAA AACAACGCAG ACTGCTGAAG GCCACTCAAC GACGAGGCGC CGAAATCGAC 960

AGACCCATGC CTGTCGTGCC TGAAGAATGT TACGACCAAC GCTTCACTAC CGAAGGCCAC 1020

CAGGTCATCC CGTTGTGCGC GTCCGAACCC GAGGATGACG ACGAAGATCC TACCTACGAC 1080

GAATTGCCGT CGCGCCCACC CCAGAAACAT AAGCCGCCAG ACAAACCTCC GCGCTTATGC 1140

AAAACGGGCC CCGGCCCACC TCCGCTGCCG CCAAAGCAAC GGCACGGTTC CACCGACGGA 1200

AAAGTTTCTG CGCCCCGACA GTCGGAGCAT CATAAAAGAC AGACCCGACC GCCAAGGCCG 1260

CCACCGCCCA AATTCGGGGA TAGAACCGCG GCCCATCTCT CGCAAAATAT GCGGGACATG 1320

TACCTCGATA TGTGTACATC TTCGGGCCAC AGGCCACGGC CGCCAGCACC TCCGCGGCCG 1380

AAAAAATGTC AAACACACGC CCCTCACCAC GTTCATCATT GAAAGTCTCT CCAGTCCATA 1440

TGTTGTCAGG ACGTGCTGTC GTTCTCCGCT TGCTGCGAAG CCCGTTCTTC CGAGTCGTGT 1500

CGCTGCGTCC AGCGTCGCGC CCAAGATGGG AATTTGGGTC TTTTCACGCG TAGCCTCCTC 1560

CACCACGGCT GCTGATCGCC GTCACTAAGG ACCGACACGG AGGATGACGA GGAGCTTCTC 1620

CCCGACTCCG CGGTCCGCGA CCGGCTACGT AGCGCGTGTC CCTGCCAGTC TCCGCAGTTA 1680

CACCACACGT CGTGAGCAGC GTGCACCTGC TGCCGCCACT GGGCCTCGGC GTGCTCAGGC 1740

CACCCGCCGG AGCCCGGTCT GAGCT 1765

( 2 ) INFORMATION FOR SEQ ID NO:16:

( i ) SEQUENCE CHARACTERISTICS:
( A ) LENGTH: 1611 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GCCCCTGCCG CCCAACTGAA CACGCATACC CCGCTCAACT GCGTTTTGCC ACCCCTGTCA 60

GTGCTCTCGC TCGAGCACCA CCCCGCATCT CCCAACCTTT TTCCAATAAA CGAAACCGAC 120

ATGACACACG TAATGGGTAC TCGTGGCTAG ATTTATTGAA ATAAACCGCG ATCCCGGGCG 180

TCTCAGCACA CGAAAAACCG CATCCACATC ATAGACAAGT TACAGTCCAC AGTCACATAC 240

ACGATAAACA ATACCAACAG GGTAATGTTT ATGGAGTAAA ACACTATTGT CCAGGCCACA 300

TGCGTGTATG ACTTCCGCAC CATCCCGTAC TGCATGTTCC ACATGTACGC GCTAGACGTG 360

TAATCCACTC GCAGTTCGGG GACGCAACGC AGCCAGATCA CATCCCCTTG CAGTACCAGA 420

CGCAGGGCTA GCGTCTCGAA GATCGGCATC ACATCTAAGT TCCGCACGTT CCACTTTAAC 480

GACTCCCCGG GAACGAACTC CACGTCGTCG GCGTGTACGT ACAGGTTCTC TCCCACGCCG 540

CCATAATCGG CCTTCGGATC GAAGACGAAC CGACTCATGT TGCCCACGAT GCTCCCCCGA 600

GCAAACAACT TGCCGTTGTC AATGTAGCAC CGGTTGTCCT CGATTTGAAA CCAGGGATGC 660

-continued

| | | | | | | |
|---|---|---|---|---|---|---|
| TTGGCCGTGG | ACTTCCAGGG | CCGGAGCGCG | TCTTCCCCGG | CTTTAGTGAT | TCCATCGGGC | 720 |
| AGGCGGATCA | AGGGACCCAT | GGAGGTCCAA | AGACCCACCC | AGGCTTTCCA | GAGATTGTTC | 780 |
| ATGGTGAAAC | AGCGTGTGGA | CTGTACGCTC | TTTCCCAATT | TATATCCCAG | AGTAGTGACG | 840 |
| TGAGCCCAGC | CACCTCCCAG | ATTCCTGACG | TTTTGGTTGT | CTTTCCTGCC | AATTCCTCCC | 900 |
| GTAAACTTAT | GATTATCCTA | GCCCATTCCC | GATAAAAATA | CACGGAGACA | GTAGATAGAG | 960 |
| TTACGAATAA | ACCGGTTTAT | TTATTCAAGT | GTCTCAGGAG | ATTATTGAAC | GAGCGTGGAT | 1020 |
| ACCACGCCGT | CGTCAGTTCA | TGGTGGCATT | GAGCAGCCAT | AGCACCAGAG | TCCCGGCGCC | 1080 |
| CGGTATCAGA | CACGCTGACC | TACCGGGCGC | CTTCGAGTCC | GTACCCCGCG | GCCTGGGTGT | 1140 |
| TAGAGTCCGT | ACCTTGCAGC | CCAGGTAGGT | TTCAGGTACC | AGCTGGTTCG | TACCTGTTAA | 1200 |
| ATAAATCGCA | GACGGGCGCT | CACCCCTACG | GTCAGGAGCA | CAAGAACAAC | CAGAGAGAAC | 1260 |
| AGATATACGA | GCAGGGTTCT | GAACAGCAGA | CCCCAATTGT | CGTCTCTCAT | GCTTCGCTGA | 1320 |
| AGGTACCAGT | TGATGGTCTG | AGAGCTATAG | TCCATCCTCA | CCTGAGGAAC | ACACGCGGCA | 1380 |
| TATTTCTTGG | GGTCTCCCCA | CCTCGTAGAC | AACGTGATGT | CCACCATATC | CACGGTGTGC | 1440 |
| GTCACCGGGT | GCCCACCGAT | GTTCCACTCG | AAATAGGCTC | CGCGCTCATC | ATGGTGGTAC | 1500 |
| TGCTCACCGG | ACACCTGCAG | TCTGTCCATG | TAAGATTGAG | AGACGATACC | CACGTTCACA | 1560 |
| AAGTGTTTCT | CGGTGAAGTT | GCCCGACATC | CTCCCCTTGA | AGTACAGCAT | G | 1611 |

( 2 ) INFORMATION FOR SEQ ID NO:17:

( i ) SEQUENCE CHARACTERISTICS:
( A ) LENGTH: 1174 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

| | | | | | | |
|---|---|---|---|---|---|---|
| GCGCCGAAAT | CGACAGACCC | ATGCCTGTCG | TGCCTGAAGA | ATGTTACGAC | CAACGCTTCA | 60 |
| CTACCGAAGG | CCACCAGGTC | ATCCCGTTGT | GCGCGTCCGA | ACCCGAGGAT | GACGACGAAG | 120 |
| ATCCTACCTA | CGACGAATTG | CCGTCGCGCC | CACCCCAGAA | ACATAAGCCG | CCAGACAAAC | 180 |
| CTCCGCGCTT | ATGCAAAACG | GGCCCCGGCC | CACCTCCGCT | GCCGCCAAAG | CAACGGCACG | 240 |
| GTTCCACCGA | CGGAAAAGTT | TCTGCGCCCC | GACAGTCGGA | GCATCATAAA | AGACAGACCC | 300 |
| GACCGCCAAG | GCCGCCACCG | CCCAAATTCG | GGGATAGAAC | CGCGGCCCAT | CTCTCGCAAA | 360 |
| ATATGCGGGA | CATGTACCTC | GATATGTGTA | CATCTTCGGG | CCACAGGCCA | CGGCCGCCAG | 420 |
| CACCTCCGCG | GCCGAAAAAA | TGTCAAACAC | ACGCCCCTCA | CCACGTTCAT | CATTGAAAGT | 480 |
| CTCTCCAGTC | CATATGTTGT | CAGGACGTGC | TGTCGTTCTC | CGCTTGCTGC | GAAGCCCGTT | 540 |
| CTTCCGAGTC | GTGTCGCTGC | GTCCAGCGTC | GCGCCCAAGA | TGGGAATTTG | GGTCTTTTCA | 600 |
| CGCGTAGCCT | CCTCCACCAC | GGCTGCTGAT | CGCCGTCACT | AAGGACCGAC | ACGGAGGATG | 660 |
| ACGAGGAGCT | TCTCCCCGAC | TCCGCGGTCC | GCGACCGGCT | ACGTAGCGCG | TGTCCCTGCC | 720 |
| AGTCTCCGCA | GTTACACCAC | ACGTCGTGAG | CAGCGTGCAC | CTGCTGCCGC | CACTGGGCCT | 780 |
| CGGCGTGCTC | AGGCCACCCG | CCGGAGCCCG | GTCTGAGCTC | CGACGCAGGA | TGCGCGTACT | 840 |
| CAACGTGCGC | CTTCCAGTCC | ATACAGCAAC | ACCATAGGTC | GTGCGAGTCG | TCGGCTACCC | 900 |
| GCCGCCAGGC | CAGTTCCCGC | ATGGGAAGGC | TGGACACGCC | GACCGAGAGG | TCACCGAGCC | 960 |
| CGGACGCCAT | CTCTTCTTCC | TCTCCGTCGC | TGTCATTAAG | CAGCCAGGTC | ACCTCCTCCG | 1020 |
| CTCCGCGTCC | GCCGGTCTCG | ACGGACCGCG | CCGCCGTCGG | CAACACGGAA | AACAGCACGC | 1080 |

-continued

CAGCCCGAGC CGCTAAGGCC GCATGCCCCT GCCGCCCAAC TGAACACGCA TACCCCGCTC 1140

AACTGCGTTT TGCCACCCCT GTCAGTGCTC TCGC 1174

( 2 ) INFORMATION FOR SEQ ID NO:18:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

CCATGCCGGG AAAGCACATT CCTTTTCAGT AAACAACAAT GACATCATAA CAAATCATTT 60

TATTCG 66

( 2 ) INFORMATION FOR SEQ ID NO:19:

( i ) SEQUENCE CHARACTERISTICS:
( A ) LENGTH: 645 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CCACTGGTCC GAAAACATCC AGGGAAAATG TCGGTGCAGC CAACCTTTCA CATACAGCCC 60

CCAAAACACT TGAATCACTG CCACCATCAT CAGCGTATAC TGCGCCGACT TAATCGTGAG 120

CGCGTAGTAC GCCATTAGAC GGCGATCTTC GAACAATAGT CGTTCGATGT CCTCTAACGA 180

GCTCCACAGG GGAACCCAAG GCACGAGGCA CCGGGGTTCG CACTCTACAT AATAAGTTTG 240

GCATTGGTGG CAGGGGGAAA AGTAGAACAA CACGAGTTTT GTGCGTTGGG GAACACGATA 300

GTCCCGGAGC CAGTAGCGTT TTGCGACGAG GCTTTCGGAG ACGTCCTCCA CCGGCGTCGG 360

CACTCGATCC GCGTAGCCCT CCAGCGTCTG GTAGTACACC CGGGGTGTCG GCGTGGGCAC 420

GGACAGGTTC CCGCGCAGGG TCCACAGAGC CTCCAGTCGA CCGCCCGATC GGAGCACGCA 480

GCGCGCCTCG GAATACTCTA CTCGGTACTC CGAAACATCG GACAGAGGCG GTAACGGCTC 540

CGTCTCCACC AAGGGCGGAG GTTCATCGAA AAGAGTCAAG GATAATTCAG GCATACTACC 600

CGCGACCGGG GCCCAGAGGG CTAGAATAAG CATTACAAGG TTCAT 645

( 2 ) INFORMATION FOR SEQ ID NO:20:

( i ) SEQUENCE CHARACTERISTICS:
( A ) LENGTH: 709 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

CTCGAGATGC ACTCCGCTTC AGTCTATATA TCACCACTGG TCCGAAAACA TCCAGGGAAA 60

ATGTCGGTGC AGCCAACCTT TCACATACAG CCCCCAAAAC ACTTGAATCA CTGCCACCAT 120

CATCAGCGTA TACTGCGCCG ACTTAATCGT GAGCGCGTAG TACGCCATTA GACGGCGATC 180

TTCGAACAAT AGTCGTTCGA TGTCCTCTAA CGAGCTCCAC AGGGGAACCC AAGGCACGAG 240

GCACCGGGGT TCGCACTCTA CATAATAAGT TTGGCATTGG TGGCAGGGGG AAAAGTAGAA 300

-continued

| | | | | | | |
|---|---|---|---|---|---|---|
| CAACACGAGT | TTTGTGCGTT | GGGGAACACG | ATAGTCCCGG | AGCCAGTAGC | GTTTTGCGAC | 360 |
| GAGGCTTTCG | GAGACGTCCT | CCACCGGCGT | CGGCACTCGA | TCCGCGTAGC | CCTCCAGCGT | 420 |
| CTGGTAGTAC | ACCCGGGGTG | TCGGCGTGGG | CACGGACAGG | TTCCCGCGCA | GGGTCCACAG | 480 |
| AGCCTCCAGT | CGACCGCCCG | ATCGGAGCAC | GCAGCGCGCC | TCGGAATACT | CTACTCGGTA | 540 |
| CTCCGAAACA | TCGGACAGAG | GCGGTAACGG | CTCCGTCTCC | ACCAAGGGCG | GAGGTTCATC | 600 |
| GAAAAGAGTC | AAGGATAATT | CAGGCATACT | ACCCGCGACC | GGGGCCCAGA | GGGCTAGAAT | 660 |
| AAGCATTACA | AGGTTCATTC | TGTCTTACAA | GGGAAGGCTG | TTACCCTGT | | 709 |